(12) United States Patent
Duncan

(10) Patent No.: US 10,626,092 B2
(45) Date of Patent: Apr. 21, 2020

(54) POLYMORPHIC FORMS OF 3-[(2-BUTYL-1-(2-DIETHYLAMINO-ETHYL)-1H-BENZOIM-IDAZOL-5-YL]-N-HYDROXY-ACRYLAMIDE AND USES THEREOF

(71) Applicant: MEI PHARMA, INC., San Diego, CA (US)

(72) Inventor: David Duncan, San Diego, CA (US)

(73) Assignee: MEI PHARMA, INC., San Diego, CA (US)

( * ) Notice: Subject to any disclaimer, the term of this patent is extended or adjusted under 35 U.S.C. 154(b) by 0 days.

(21) Appl. No.: 16/098,435

(22) PCT Filed: May 1, 2017

(86) PCT No.: PCT/US2017/030414
§ 371 (c)(1),
(2) Date: Nov. 1, 2018

(87) PCT Pub. No.: WO2017/192451
PCT Pub. Date: Nov. 9, 2017

(65) Prior Publication Data
US 2019/0152923 A1 May 23, 2019

Related U.S. Application Data

(60) Provisional application No. 62/330,673, filed on May 2, 2016.

(51) Int. Cl.
| C07D 235/08 | (2006.01) |
| A61K 31/4184 | (2006.01) |
| C07D 235/14 | (2006.01) |
| A61P 35/02 | (2006.01) |

(52) U.S. Cl.
CPC ........ *C07D 235/14* (2013.01); *A61K 31/4184* (2013.01); *A61P 35/02* (2018.01); *C07D 235/08* (2013.01); *C07B 2200/13* (2013.01)

(58) Field of Classification Search
CPC .............. C07D 235/08; A61K 31/4184; C07B 2200/13
See application file for complete search history.

(56) References Cited

U.S. PATENT DOCUMENTS

| 6,552,065 | B2 | 4/2003 | Remiszewski et al. |
| 7,112,600 | B1 | 9/2006 | Hashimoto et al. |
| 7,517,875 | B2 | 4/2009 | Matsumoto et al. |
| 7,781,595 | B2 | 8/2010 | Chen et al. |
| 8,143,282 | B2 * | 3/2012 | Chen .................... C07D 235/06 514/322 |
| 8,551,988 | B2 | 10/2013 | Chen et al. |
| 9,024,029 | B2 | 5/2015 | Chen et al. |
| 9,402,829 | B2 | 8/2016 | Chen et al. |
| 9,717,713 | B2 | 8/2017 | Chen et al. |
| 10,201,527 | B2 | 2/2019 | Chen et al. |
| 2003/0018062 | A1 | 1/2003 | Remiszewski et al. |
| 2003/0050320 | A1 | 3/2003 | Hashimoto et al. |
| 2004/0082635 | A1 | 4/2004 | Hashimoto et al. |
| 2004/0209895 | A1 | 10/2004 | Luecking et al. |
| 2004/0254220 | A1 | 12/2004 | Bressi et al. |
| 2004/0266769 | A1 | 12/2004 | Bressi et al. |
| 2005/0137232 | A1 | 6/2005 | Bressi et al. |
| 2005/0137234 | A1 | 6/2005 | Bressi et al. |
| 2005/0159470 | A1 | 7/2005 | Bressi et al. |
| 2007/0043043 | A1 | 2/2007 | Chen et al. |
| 2009/0048300 | A1 | 2/2009 | Chen et al. |
| 2010/0256138 | A1 | 10/2010 | Chen et al. |
| 2015/0157608 | A1 | 6/2015 | Chen et al. |
| 2015/0258068 | A1 | 9/2015 | Gold et al. |
| 2016/0279102 | A1 | 9/2016 | Chen et al. |
| 2017/0360757 | A1 | 12/2017 | Chen et al. |

FOREIGN PATENT DOCUMENTS

| CA | 2363274 A1 | 7/2001 |
| FR | 2291749 A1 | 6/1976 |
| WO | WO-9323041 A1 | 11/1993 |
| WO | WO-0034254 A1 | 6/2000 |
| WO | WO-0042022 A1 | 7/2000 |
| WO | WO-0100207 A1 | 1/2001 |
| WO | WO-0100213 A1 | 1/2001 |
| WO | WO-0105390 A2 | 1/2001 |
| WO | WO-0105393 A2 | 1/2001 |
| WO | WO-0112604 A1 | 2/2001 |
| WO | WO-0138322 A1 | 5/2001 |
| WO | WO-0147883 A1 | 7/2001 |
| WO | WO-0210137 A2 | 2/2002 |
| WO | WO-0242273 A2 | 5/2002 |
| WO | WO-0250062 A2 | 6/2002 |
| WO | WO-03000254 A1 | 1/2003 |
| WO | WO-03000682 A1 | 1/2003 |

(Continued)

OTHER PUBLICATIONS

Alzheimer's Disease Treatment Phases(downloaded Mar. 10, 2008), http:www.alzheimerstreatment.org/treatment/disease-treatment.htm.
Alzheimer's Drugs, Consumer Reports best Buy Drugs (p. 1-16, 2006).
Bare, et al., Synthesis and structure-activity relationships of a series of anxioselective pyrazolopyridine ester and amide anxiolytic agents. Journal of Medicinal Chemistry, 32:2561-2573, 1989.
Baudy et al, "Design, Synthesis, SAR, and Biological Evaluation of Highly Potent Benzimidazole-Spaced Phosphono-a-Amino Acid Colmpetitive NMDA Antagonists of the AP-6 Type" J. Med. Chem. 44:1516-1529, 2001.
Bitterman et al, "Inhibition of Silencing and Accelerated Aging by Nicotinamide, a Putative Negative Regulator of Yeast Sir2 and Human SIRT1" J. Biol. Chem. 277(47):45099-45107, 2002.
Bouchain, G. et al, "Development of Potential Antitumor Agents. Synthesis and Biological Evaluation of a New Set of Sulfonamide Derivatives as Histone Deacetylase Inhibitors" J. Med. Chem., 46 (5), 820-830 (2003).

(Continued)

*Primary Examiner* — Laura L Stockton
(74) *Attorney, Agent, or Firm* — Wilson Sonsini Goodrich & Rosati

(57) ABSTRACT

Crystalline polymorph forms of 3-[2-butyl-1-(2-diethyl-amino-ethyl)-1H-benzoimidazol-5-yl]-N-hydroxy-acrylamide are described. Pharmaceutical compositions and the uses of such compounds, compound forms, and compositions for the treatment of diseases and conditions are also presented.

13 Claims, 54 Drawing Sheets

(56) References Cited

FOREIGN PATENT DOCUMENTS

| WO | WO-03066579 A2 | 8/2003 |
|---|---|---|
| WO | WO-03077855 A2 | 9/2003 |
| WO | WO-03077914 A1 | 9/2003 |
| WO | WO-03087089 A1 | 10/2003 |
| WO | WO-2004078682 A2 | 9/2004 |
| WO | WO-2005028447 A1 | 3/2005 |
| WO | WO-2006101456 A1 | 9/2006 |
| WO | WO-2007030080 A1 | 3/2007 |
| WO | WO-2008108741 A1 | 9/2008 |

OTHER PUBLICATIONS

Butler, L.M. et al, "Suberoylanilide hydroxamic acid, an inhibitor of histone deacetylase, suppresses the growth of prostate cancer cells in vitro and in vivo", Cancer Res. 60:5165-5170, 2000.
Carballo et al, "Feedback Inhibition of Macrophage Tumor Necrosis Factor-a Production by Tristetraprolin" Science, 281:1001-1005, 1998.
Collins, Discontinued drugs in 2006: central and peripheral nervous system drugs. Expert Opinion Investig. Drugs, 16:(110):1743-1751, 2007.
Cumming, et al., Controlled release solid oral dosage form containing a histone deacetylase inhibitor and a medium chain fatty acid derivative as an absorption enhancer. Caplus 2007: 705011, 3 pages.
De Ruijter, A.J.M. et al, "Histone deacetylases (HDACs): characterization of the classical HDAC family" Biochem. J., 370:737-749, 2003.
Dinarello, C.A. and Moldawer L.L. "Proinflammatory and anti-inflammatory cytokines in rheumatoid arthritis. A primer for clinicians." 3rd Edition, Amgen Inc., 2002, pp. 1-352.
Dostert et al., Benzimidazoleacetic acid derivatives. CAPLUS, 1977:171447, 2 pages
European Patent Application No. 04775628 Partial European Search Report dated Oct. 24, 2007, Cover Page Only.
European Patent Application No. 04775628 Supplementary European Search Report dated Dec. 21, 2007, Cover Page Only.
European Patent Application No. 06769700 European Search Report dated Jan. 22, 2010, Cover Page Only.
Fenaux et al., Efficacy of azacitidine compared with that of conventional care regimens in the treatment of higher-risk myelodysplastic syndromes: a randomized, open-label, phase III study. Lancet Oncol. 10(3):223-232, 2009.
Garcia-Manero et al., A randomized, placebo-controlled, phase II study of pracinostat in combination with azacitidine (AZA) in patients with previously untreated myelodysplastic syndrome (MDS). Blood. 126:911-916, 2015.
Garcia-Manero et al., Phase 2 study of pracinostat and azacitidine in older patients with acute myeloid leukemia (AML) not eligible for induction chemotherapy: response and long-term survival benefit. Blood. 128: Abstract 100, 2016.
Garcia-Manero et al., Phase I study of the oral histone deacetylase inhibitor SB939 in patients with advanced hematologic malignancies. Blood. 116:Abstract 3292, 5 pages, 2010.
Garcia-Manero et al., Updated results from a phase 2 study of pracinostat in combination with azacitidine in elderly patients with acute myeloid leukemia. 20th Congress of the European Hematology Association. Vienna, Austria. 1 page. Jun. 11-14, 2015.
"Goodman & Gilman's The Pharmacological Basis of Therapeutics, 9th edition, Section X, Chemotherapy of Neoplastic Diseases, p. 1225-1232(1996)".
Gupta and Kumaran, Quantitative structure-activity relationship studies on Matrix Metalloproteinase inhibitors: Bicyclic heteroaryl hydroxamic acid analogue. Letters in Drug Design & Discovery, 2:522-528, 2005.
Heltweg and Jung, "A Microplate Reader-Based Nonisotopic Histone Deacetylase Activity Assay" Anal. Biochem. 302:175-183, 2002, Abstract Only.

Inoue and D. Fujimoto, "Enzymatic Deacetylation of Histone" Biochemical Biophysical Research Communications, 36(1):146-150, 1969.
Ito et al, "A Molecular Mechanism of Action of Theophylline: Induction of Histone Deacetylase Activity to Decrease Inflammatory Gene Expression" Proc. Natl. Acad. Sci. USA 99(13):8921-8926, 2002.
Ito et al, "p300/CBP-mediated p53 acetylation is commonly induced by p53-activating agents and inhibited by MDM2" EMBO Journal. 20(6):1331-1340, 2001.
Kijima, M. et al, "Trapoxin, an Antitumor Cyclic Tetrapeptide, Is an Irreversible Inhibitor of Mammalian Histone Deacetylase" J. Biol. Chem., vol. 268, No. 30, pp. 22429-22435 (1993).
Milutinovic et al, "Proliferating Cell Nuclear Antigen Associates with Histone Deacetylase Activity, Integrating DNA Replication and Chromatin Modification" J. Biol. Chem. 277(23):20974-20978, 2003.
PCT/SG2004/000307 International Search Report dated Oct. 29, 2004.
PCT/SG2004/000307 Written Opinion dated Oct. 29, 2004.
PCT/SG2006/000217 International Search Report dated Oct. 19, 2006.
PCT/SG2006/00217 Written Opinion dated Oct. 19, 2006.
PCT/US2017/030414 International Search Report and Written Opinion dated Aug. 3, 2017.
Quintás-Cardama et al., Therapy with the histone deacetylase inhibitor, pracinostat, for patients with myelofibrosis. Leuk Res. 36(9):1124-1127, 2012, Abstract Only.
Quintás-Cardama et al., Very high rates of clinical and cytogenetic response with the combination of the histone deacetylase inhibitor pracinostat (SB939) and 5-azacitidine in high-risk myelodysplastic syndrome. 54th ASH Annual Meeting, Dec. 2012, Abstract 3821, Blood, 120:3821-3825, 2012, Abstract Only.
Remiszewski et al, "Inhibitors of Human Histone Deacetylase: Synthesis and Enzyme and Cellular Activity of Straight Chain Hydroxamates" J. Med. Chem., 45(4):753-757, 2002.
Richon, V.M. et al, "A class of hybrid polar inducers of transformed cell differentiation inhibits histone deacetylases" Proc. Natl. Acad. Sci. USA, vol. 95: pp. 3003-3007 (1998).
Richon, V.M. et al, "Second generation hybrid polar compounds are potent inducers of transformed cell differentiation" Proc. Natl. Acad. Sci. USA, 93:5705-5708, 1996.
Schindler et al., "Dissociation between Interleukin-1l1 mRNA and Protein Synthesis in Human Peripheral Blood Mononuclear Cells" J. Biol. Chem., 265(18):10232-10237, 1990.
Cayman Chemical: Safety Data Sheet SB 939; 20150301, p. 1, 3; URL: https://www.caymanchem.com/msdss/10443m.pdf, XP055436898; (2015).
Jayaraman et al.: Preclinical Metabolism and Disposition of SB939 (Pracinostat), an Orally Active Histone Deacetylase Inhibitor, and Prediction of Human Pharmacokinetics; Drug Metabolism & Disposition, (Aug. 26, 2011), vol. 39, pp. 2219-2232, XP055436899 (2011).
Steffan, J.S. et al, "Histone deacetylase inhibitors arrest polyglutamine-dependent neurodegeneration in *Dropsophila*" Nature, 413:739-743, 2001.
Still et al, "Rapid Chromatographic Technique for Preparative Separations with Moderate Resolution" J. Org. Chem., 43(14):2923-2925, 1978.
Strahl et al. The language of covalent histone modifications. Nature 403:41-45 (2000).
Taunton et al, "A Mammalian Histone Deacetylase Related to the Yeast Transcriptional Regulator Rpd3p" Science, 272:408-411, 1996.
U.S. Appl. No. 10/572,958 Office Action dated Oct. 16, 2009.
U.S. Appl. No. 12/065,989 Office Action dated Jun. 29, 2011.
U.S. Appl. No. 12/065,989 Office Action dated Nov. 15, 2010.
U.S. Appl. No. 10/572,958 Office Action dated Dec. 24, 2008.
U.S. Appl. No. 12/814,964 Office Action dated Apr. 10, 2013.
U.S. Appl. No. 12/814,964 Office Action dated Nov. 30, 2012.
U.S. Appl. No. 14/016,990 Office Action dated Jul. 15, 2014.
U.S. Appl. No. 14/627,418 Office Action dated Oct. 22, 2015.
U.S. Appl. No. 15/178,742 Office Action dated Nov. 4, 2016.
U.S. Appl. No. 15/612,670 Office Action dated May 29, 2018.

(56) References Cited

OTHER PUBLICATIONS

U.S. Appl. No. 15/612,670 Office Action dated Oct. 6, 2017.
U.S. Appl. No. 14/016,990 Notice of Allowance dated Nov. 20, 2014.
Wade et al, "Purification of a Histone Deacetylase Complex from Xenopus Laevis: Preparation of Substrates and Assay Procedures" Methods in Enzymology, 304:715-725, 1999.
Wade, P.A. "Transcriptional control at regulatory checkpoints by histone deacetylases: molecular connections between cancer and chromatin" Hum. Mol. Genet. 10(7):693-698, 2001.
Witty, et al. Synthesis of conformationally restricted analogues of the tryptophanyl tRNA synthetase inhibitor indolmycin. Tetrahedron Letters, 37(17):3067-3070, 1996.
Yoshida, M. et al, "Potent and Specific Inhibition of Mammalian Histone Deacetylase Both in Vivo and in Vitro by Trichostatin A" J. Biol. Chem., 265(28):17174-17179, 1990.
Yu-Hua Ji et al, "Tris-benzimidazole derivatives: design, synthesis and DNA sequence recognition" Bioorganic & Medical Chemistry 9:2905-2919, 2001.
Byrn et al.: Pharmaceutical Solids: A Strategic Approach to Regulatory Considerations. Pharmaceutical Research. vol. 12, No. 7, 945-954 (1995).
U.S. Appl. No. 16/221,186 Office Action dated Sep. 3, 2019.

\* cited by examiner

POLYMORPHIC FORMS OF 3-[(2-BUTYL-1-(2-DIETHYLAMINO-ETHYL)-1H-BENZOIMIDAZOL-5-YL]-N-HYDROXY-ACRYLAMIDE AND USES THEREOF

CROSS-REFERENCE

This application is a U.S. National Stage entry of International Application No. PCT/US2017/030414, filed May 1, 2017, which claims the benefit of U.S. Application Ser. No. 62/330,673, filed May 2, 2016, each of which are hereby incorporated by reference in their entirety.

BACKGROUND OF THE INVENTION

Cancer is the leading cause of death worldwide.

SUMMARY OF THE INVENTION

Provided herein are polymorphic forms of 3-[2-butyl-1-(2-diethylamino-ethyl)-1H-benzoimidazol-5-yl]-N-hydroxy-acrylamide:

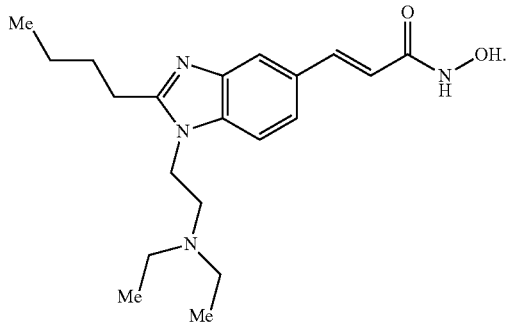 [SMILES: CCCCc1nc2cc(/C=C/C(=O)NO)ccc2n1CCN(CC)CC]

In one aspect described here is a crystalline polymorph of 3-[2-butyl-1-(2-diethylamino-ethyl)-1H-benzoimidazol-5-yl]-N-hydroxy-acrylamide dihydrochloride 2.5 hydrate characterized by a powder X-ray diffraction pattern having peaks at 6.46, 20.26, and 26.68°2θ±0.1°2θ. In further embodiments, such a crystalline polymorph is further characterized by a peak at 22.27°2θ±0.1°2θ. In yet further embodiments, such a crystalline polymorph is further characterized by at least two peaks at 9.78, 16.57, or 19.58°2θ±0.1°2θ. In some embodiments, the crystalline polymorph exhibits an X-ray powder diffraction pattern substantially the same as the X-ray powder diffraction pattern shown in FIG. 1. In some embodiments, the crystalline polymorph exhibits an X-ray powder diffraction pattern substantially similar to the X-ray powder diffraction pattern shown in FIG. 1. In a related aspect described herein is a crystalline polymorph Form 3 of 3-[2-butyl-1-(2-diethylamino-ethyl)-1H-benzoimidazol-5-yl]-N-hydroxy-acrylamide dihydrochloride 2.5 hydrate.

In some embodiments, a crystalline polymorphic form of 3-[2-butyl-1-(2-diethylamino-ethyl)-1H-benzoimidazol-5-yl]-N-hydroxy-acrylamide dihydrochloride prepared by a method comprising the step of crystallizing 3-[2-butyl-1-(2-diethylamino-ethyl)-1H-benzoimidazol-5-yl]-N-hydroxy-acrylamide dihydrochloride from a mixture of ethanol and water. In other embodiments, a crystalline polymorphic form of 3-[2-butyl-1-(2-diethylamino-ethyl)-1H-benzoimidazol-5-yl]-N-hydroxy-acrylamide dihydrochloride prepared by a method comprising the step of crystallizing 3-[2-butyl-1-(2-diethylamino-ethyl)-1H-benzoimidazol-5-yl]-N-hydroxy-acrylamide dihydrochloride 2.5 hydrate from a mixture of acetonitrile and water.

Also described herein in some embodiments, is a crystalline polymorphic form of 3-[2-butyl-1-(2-diethylamino-ethyl)-1H-benzoimidazol-5-yl]-N-hydroxy-acrylamide dihydrochloride 2.5 hydrate having an X-ray powder diffraction pattern having at least the major peaks shown in FIG. 1.

Other embodiments provided herein describe a solid pharmaceutical composition comprising an effective amount of the aforementioned crystalline polymorph form of 3-[2-butyl-1-(2-diethylamino-ethyl)-1H-benzoimidazol-5-yl]-N-hydroxy-acrylamide dihydrochloride 2.5 hydrate and at least one pharmaceutically acceptable excipient. In some embodiments, the solid pharmaceutical composition comprises an effective amount of 3-[2-butyl-1-(2-diethylamino-ethyl)-1H-benzoimidazol-5-yl]-N-hydroxy-acrylamide dihydrochloride 2.5 hydrate Form 3 as an active ingredient and at least one pharmaceutically acceptable excipient. In some embodiments, the solid pharmaceutical composition contains one or more excipients, such as one or more carriers, one or more diluents, one or more binders, one or more dispersants, one or more glidants, one or more lubricants, etc. In some embodiments, the pharmaceutical composition is for treatment of a disease, as described herein. In some embodiments, the pharmaceutical composition is for treatment of a cancer.

Also provided herein in some embodiments is a method of inhibiting histone deacetylase comprising administering an effective amount of the aforementioned crystalline polymorph form of 3-[2-butyl-1-(2-diethylamino-ethyl)-1H-benzoimidazol-5-yl]-N-hydroxy-acrylamide dihydrochloride 2.5 hydrate. In some embodiments, the method is for the treatment of cancer. In some embodiments, the cancer is chemoresistant, refractory or non-responsive to chemotherapy with an agent other than the polymorph form of 3-[2-butyl-1-(2-diethylamino-ethyl)-1H-benzoimidazol-5-yl]-N-hydroxy-acrylamide dihydrochloride 2.5 hydrate. In some embodiments, the cancer is resistant to azacitidine, decitabine, lenalidomide, TXA-127, or combinations thereof. In some embodiments, the cancer is breast cancer, colon cancer, prostate cancer, pancreatic cancer, leukemia, lymphoma, ovarian cancer, neuroblastoma, melanoma, or a hematologic malignancy. In certain embodiments, the cancer is myelodysplastic syndrome (MDS). In other embodiments, the cancer is acute myeloid leukemia (AML).

Some embodiments provided herein describe a process for the preparation of a crystalline polymorph of 3-[2-butyl-1-(2-diethylamino-ethyl)-1H-benzoimidazol-5-yl]-N-hydroxy-acrylamide dihydrochloride, the process comprising crystallizing 3-[2-butyl-1-(2-diethylamino-ethyl)-1H-benzoimidazol-5-yl]-N-hydroxy-acrylamide dihydrochloride 2.5 hydrate from a mixture of acetonitrile and water. In some embodiments, the crystalline polymorph obtained by the process is characterized by X-ray powder diffraction peaks at least at 6.46, 20.26, and 26.68°2θ±0.1°20.

Other embodiments provided herein describe a process for the preparation of a crystalline polymorph of 3-[2-butyl-1-(2-diethylamino-ethyl)-1H-benzoimidazol-5-yl]-N-hydroxy-acrylamide dihydrochloride 2.5 hydrate, the process comprising crystallizing 3-[2-butyl-1-(2-diethylamino-ethyl)-1H-benzoimidazol-5-yl]-N-hydroxy-acrylamide dihydrochloride 2.5 hydrate from a mixture of ethanol and water. In some embodiments, the crystalline polymorph obtained by the process is characterized by X-ray powder diffraction having peaks at least at 6.46, 20.26, and 26.68°2θ±0.1°2θ.

Also described herein in some embodiments, is a process for the preparation of a crystalline polymorph of 3-[2-butyl-1-(2-diethylamino-ethyl)-1H-benzoimidazol-5-yl]-N-hydroxy-acrylamide dihydrochloride 2.5 hydrate, the process comprising: suspending 3-[2-butyl-1-(2-diethylamino-ethyl)-1H-benzoimidazol-5-yl]-N-hydroxy-acrylamide dihydrochloride in acetonitrile; heating the suspension to reflux; adding water until the mixture is homogenous; and precipitating the crystalline polymorph from the solution (e.g., by cooling and/or reducing the volume of the solution). In one embodiment, the crystalline polymorph obtained by the process is characterized by X-ray powder diffraction having peaks at least at 6.46, 20.26, and 26.68°2θ±0.1°2θ. In one embodiment, the crystalline polymorph obtained by the process is characterized by at least the major X-ray powder diffraction peaks of FIG. 1.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 31A:
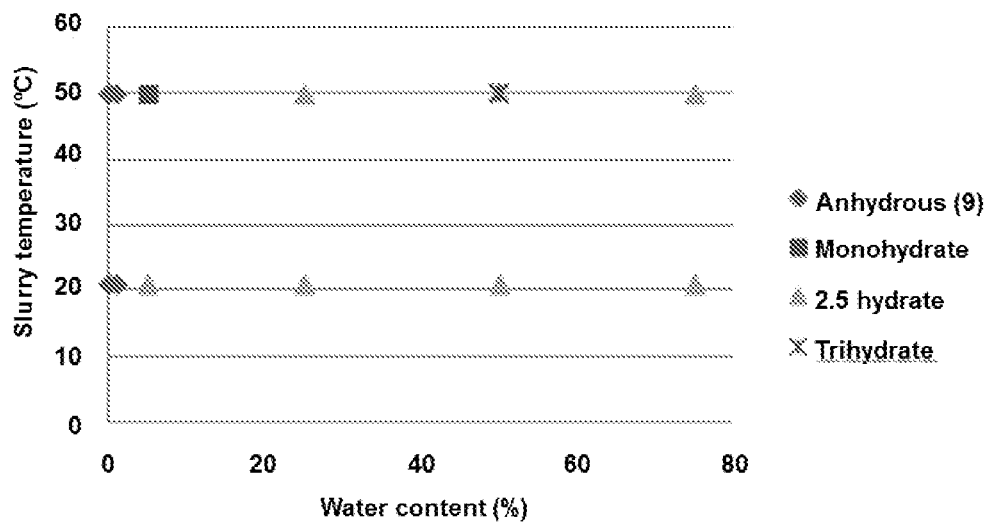
FIG. 31A depicts the results of the slurry conversion experiments on 3-[2-butyl-1-(2-diethylamino-ethyl)-1H- benzoimidazol-5-yl]-N-hydroxy-acrylamide dihydrochloride monohydrate (Form 1) under ambient conditions in ethanol/water mixtures.
Figure 31B:
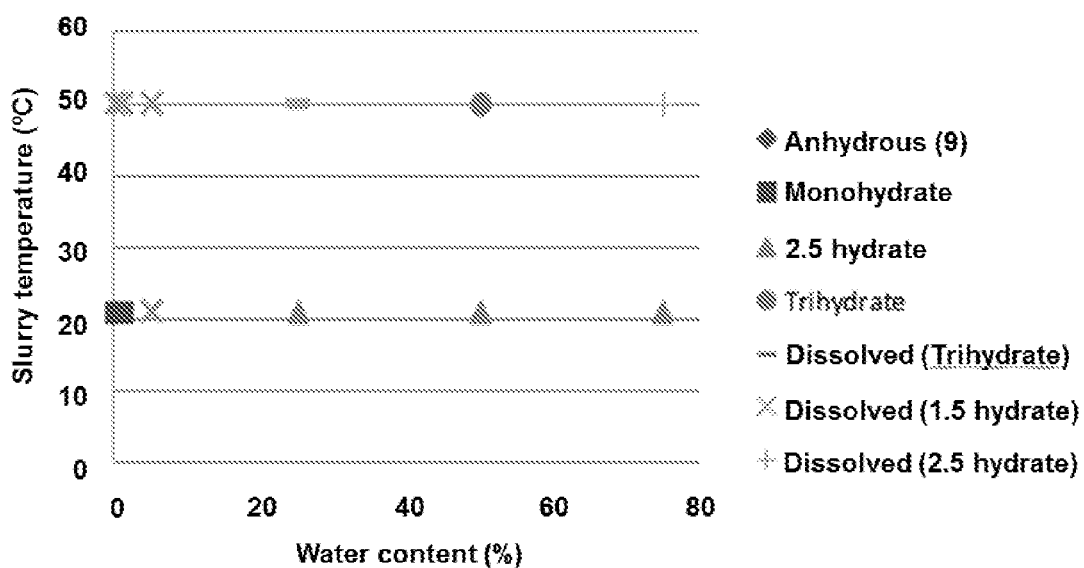

FIG. 31B depicts the results of the slurry conversion experiments on 3-[2-butyl-1-(2-diethylamino-ethyl)-1H-benzoimidazol-5-yl]-N-hydroxy-acrylamide dihydrochloride monohydrate (Form 1) under ambient conditions in methanol/water mixtures.

Figure 31C:
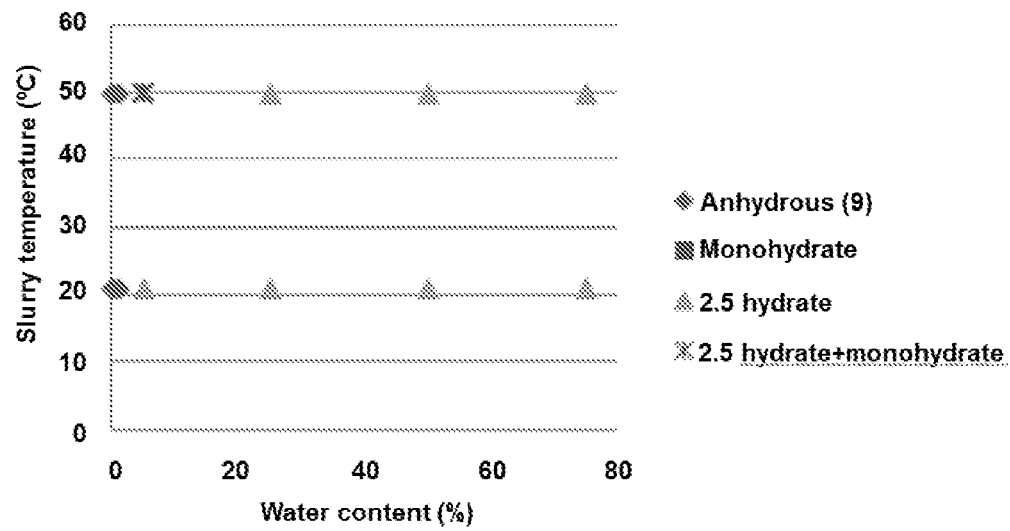

FIG. 31C depicts the results of the slurry conversion experiments on 3-[2-butyl-1-(2-diethylamino-ethyl)-1H-benzoimidazol-5-yl]-N-hydroxy-acrylamide dihydrochloride monohydrate (Form 1) under vacuum in ethanol/water mixtures.

Figure 31D:
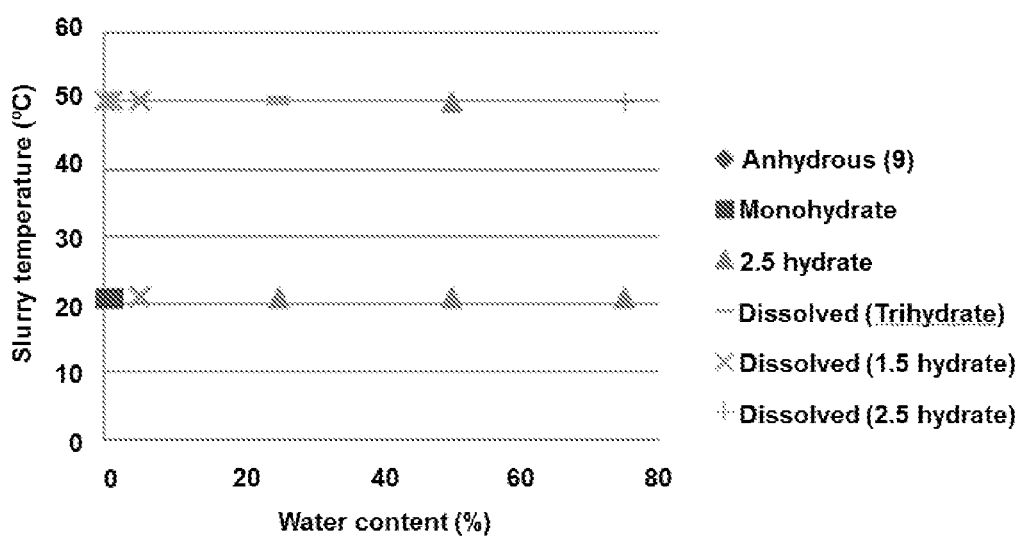

FIG. 31D depicts the results of the slurry conversion experiments on 3-[2-butyl-1-(2-diethylamino-ethyl)-1H-benzoimidazol-5-yl]-N-hydroxy-acrylamide dihydrochloride monohydrate (Form 1) under vacuum in methanol/water mixtures.

Figure 32:
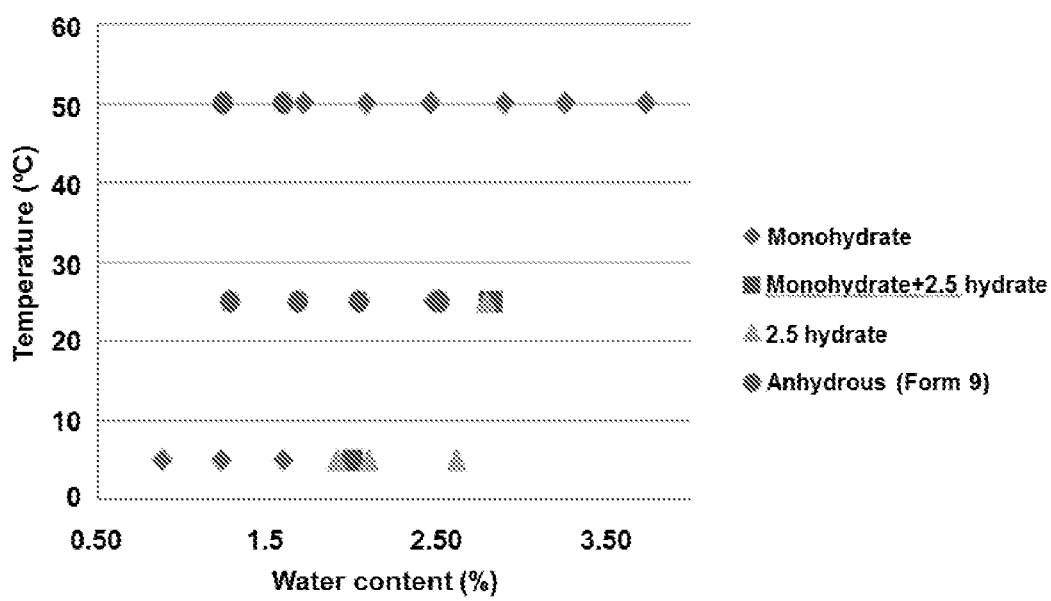

FIG. 32 depicts the solid form assignation (solids dried under ambient conditions) for the competitive slurry conversion experiments performed on 3-[2-butyl-1-(2-diethylamino-ethyl)-1H-benzoimidazol-5-yl]-N-hydroxy-acrylamide dihydrochloride monohydrate (Form 1) and 2.5 hydrate (Form 3) in ethanol/water mixtures after one week slurry, per temperature and per water content as determined by Karl Fischer analysis.

Figure 33:
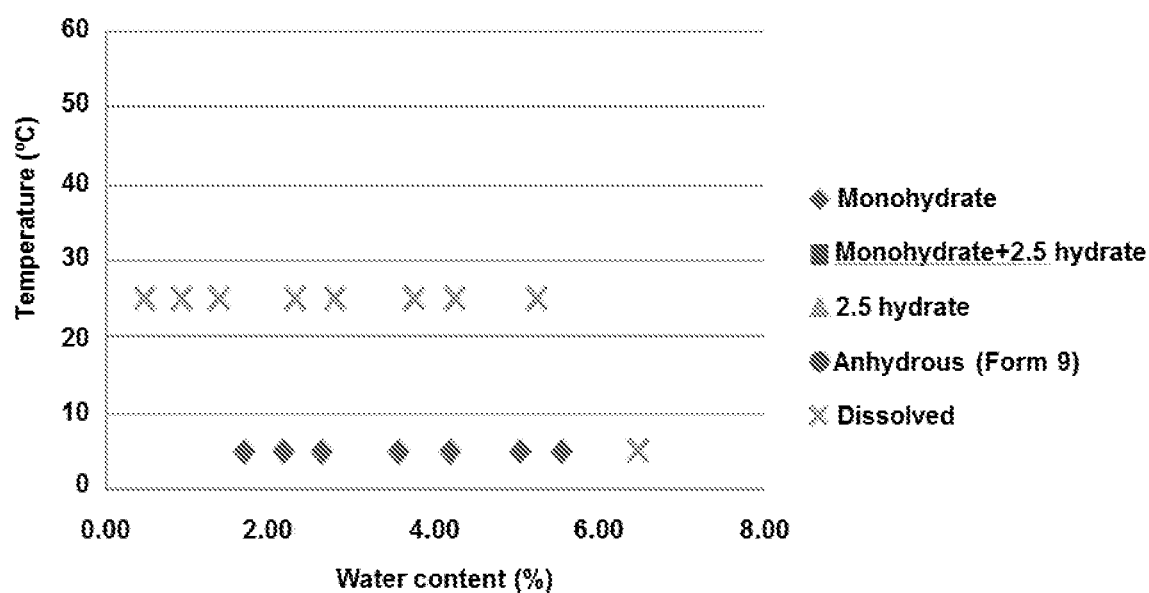

FIG. 33 depicts the solid form assignation for the competitive slurry conversion experiments performed on 3-[2-butyl-1-(2-diethylamino-ethyl)-1H-benzoimidazol-5-yl]-N-hydroxy-acrylamide dihydrochloride monohydrate (Form 1) and 2.5 hydrate (Form 3) in methanol/water mixtures after one week slurry, per temperature and per water content as determined by Karl Fischer analysis. The experiments performed at ambient conditions led to clear solution in all cases.

Figure 34:
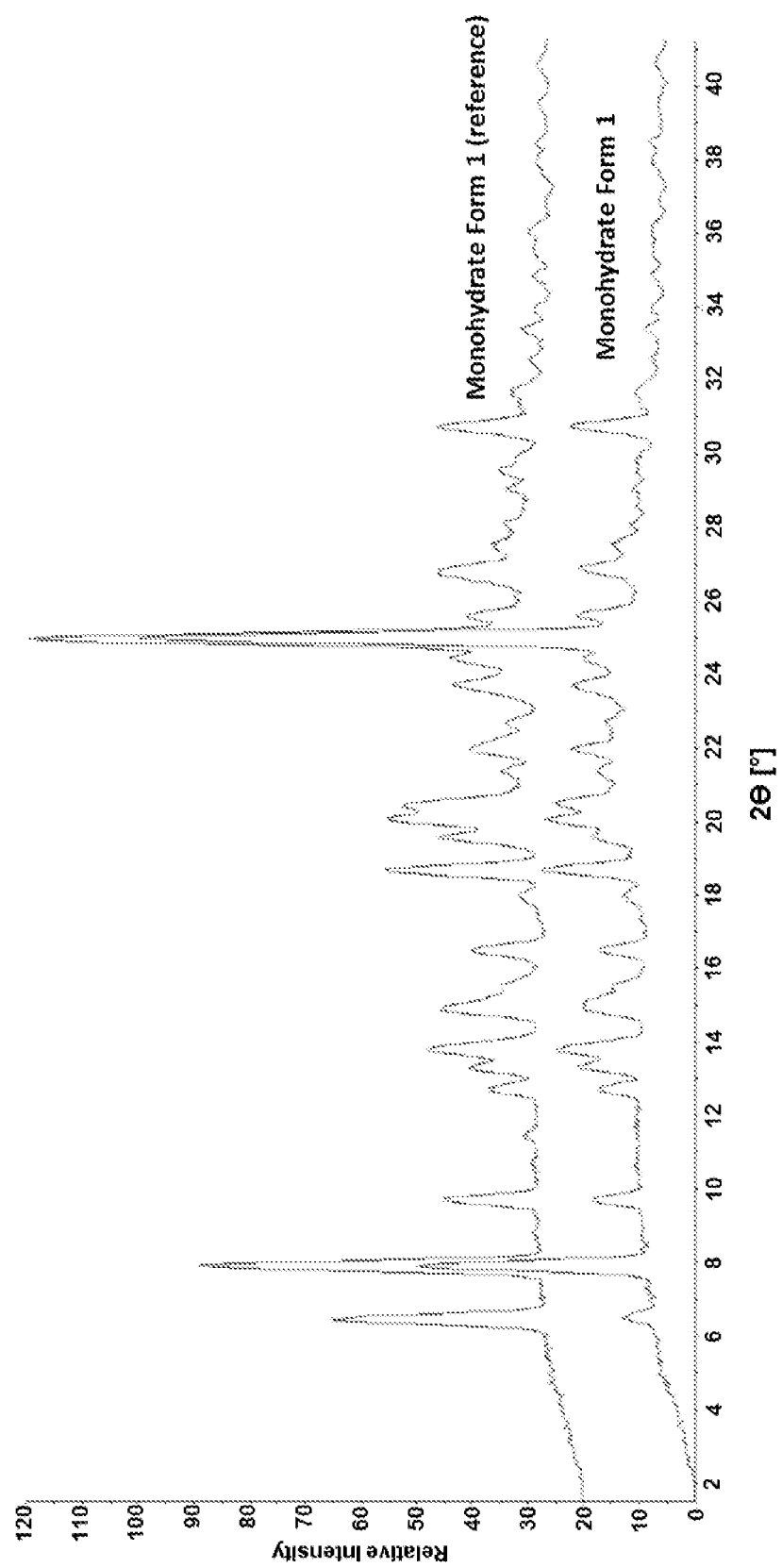

FIG. 34 depicts the overlay of HT-XRPD patterns (from bottom to top): 3-[2-butyl-1-(2-diethylamino-ethyl)-1H-benzoimidazol-5-yl]-N-hydroxy-acrylamide dihydrochloride monohydrate (Form 1) as produced by slurry conversion experiment in ethanol/water (86.4/1.6, v/v) at 50° C. and Form 1 reference material (batch DBDE8002).

Figure 35:
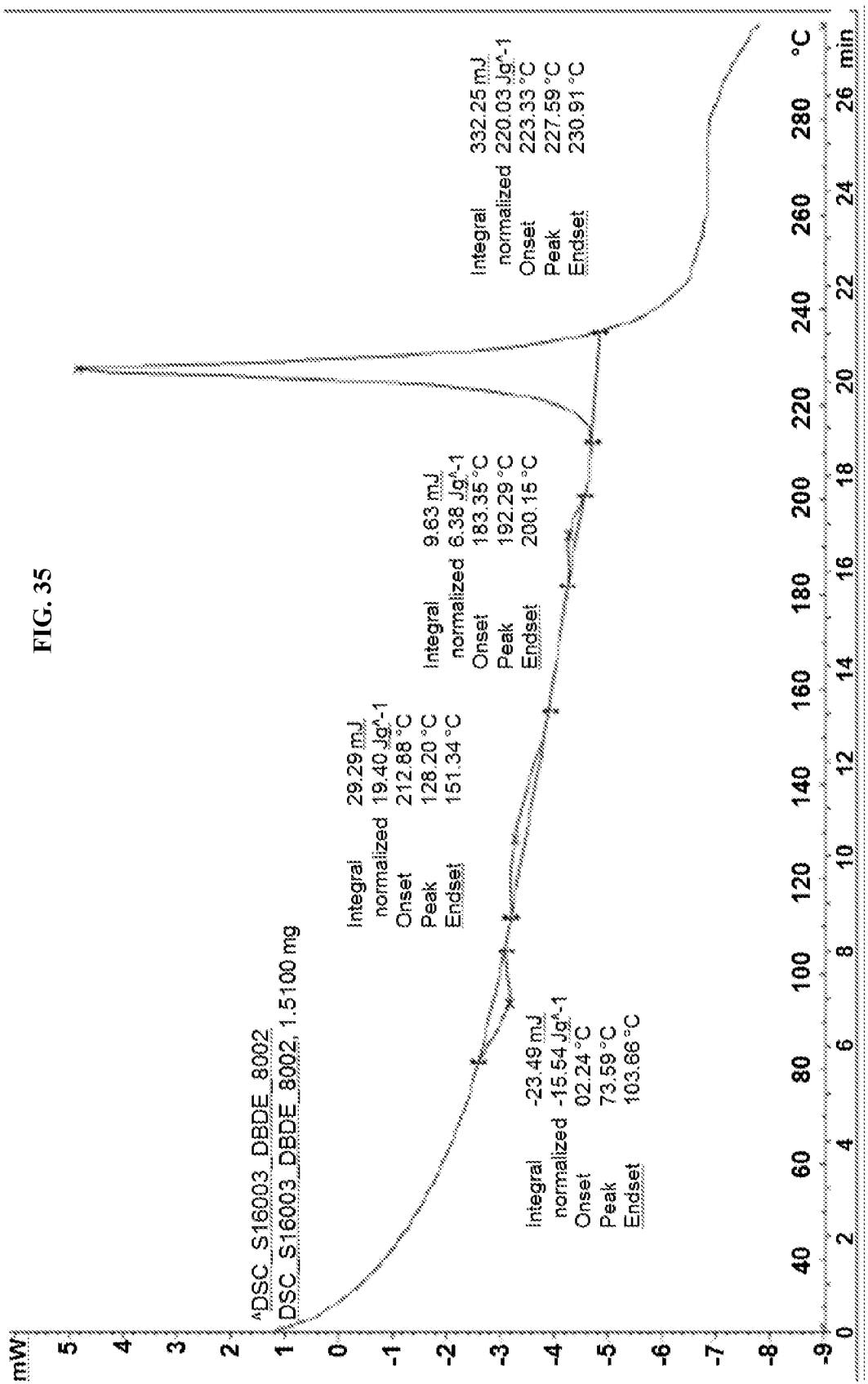

FIG. 35 depicts DSC analysis (with a heating rate of 10° C./min) of 3-[2-butyl-1-(2-diethylamino-ethyl)-1H-benzoimidazol-5-yl]-N-hydroxy-acrylamide dihydrochloride monohydrate (Form 1) reference material (batch DBDE8002). A first broad endotherm is observed at 93.9° C. followed by two broad exothermic events at 128.2° C. and 192.3° C. The sharp exothermic event observed at 227.6° C. is attributed to the thermal decomposition of the hydrochloride salt.

Figure 36A:
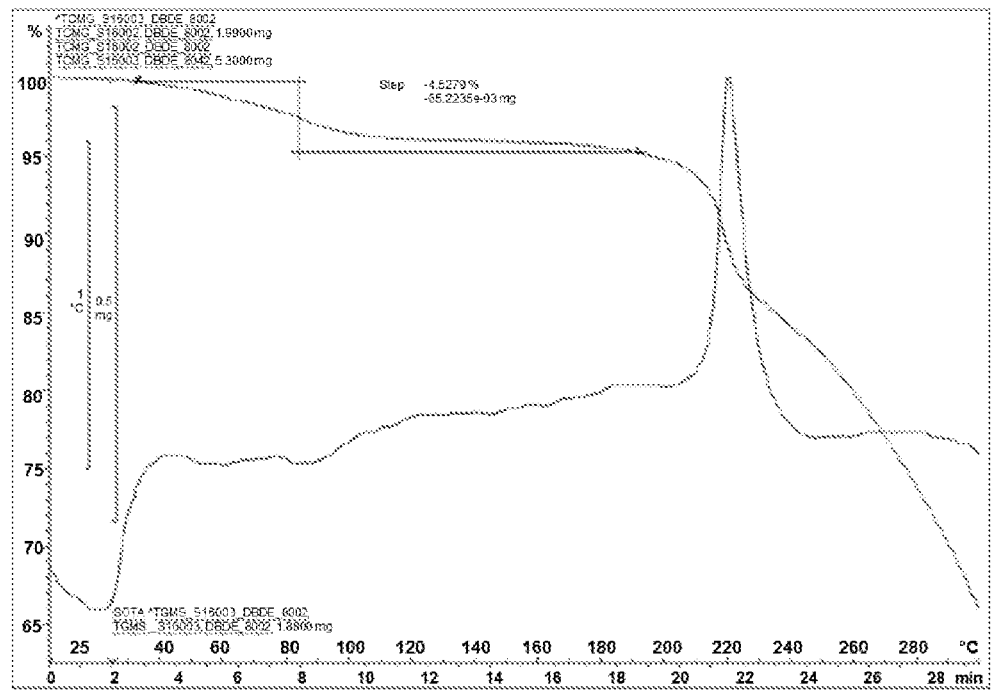

FIG. 36A depicts the TGA/SDTA analysis of 3-[2-butyl-1-(2-diethylamino-ethyl)-1H-benzoimidazol-5-yl]-N-hydroxy-acrylamide dihydrochloride monohydrate (Form 1) reference material (batch DBDE8002). The TGA signal shows a mass loss of 4.5% which based on the MS signal corresponds to water (4.5% of water corresponds to 1.1 molecules of water per molecule of API).

Figure 36B:
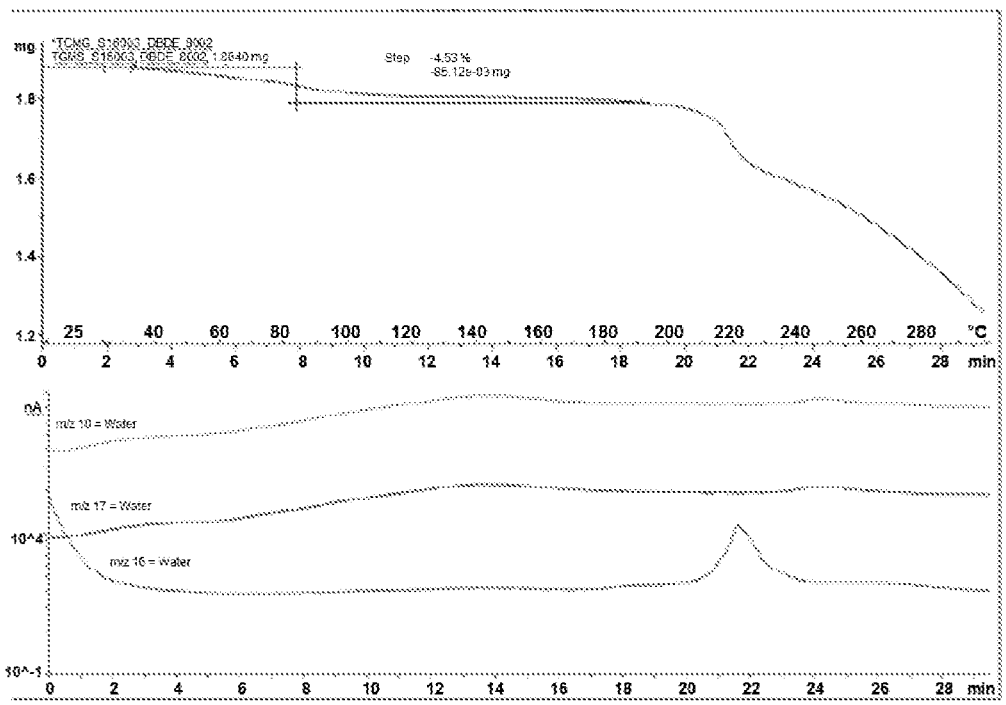

FIG. 36B depicts the TGMS analysis of 3-[2-butyl-1-(2-diethylamino-ethyl)-1H-benzoimidazol-5-yl]-N-hydroxy-acrylamide dihydrochloride monohydrate (Form 1) reference material (batch DBDE8002).

Figure 37:
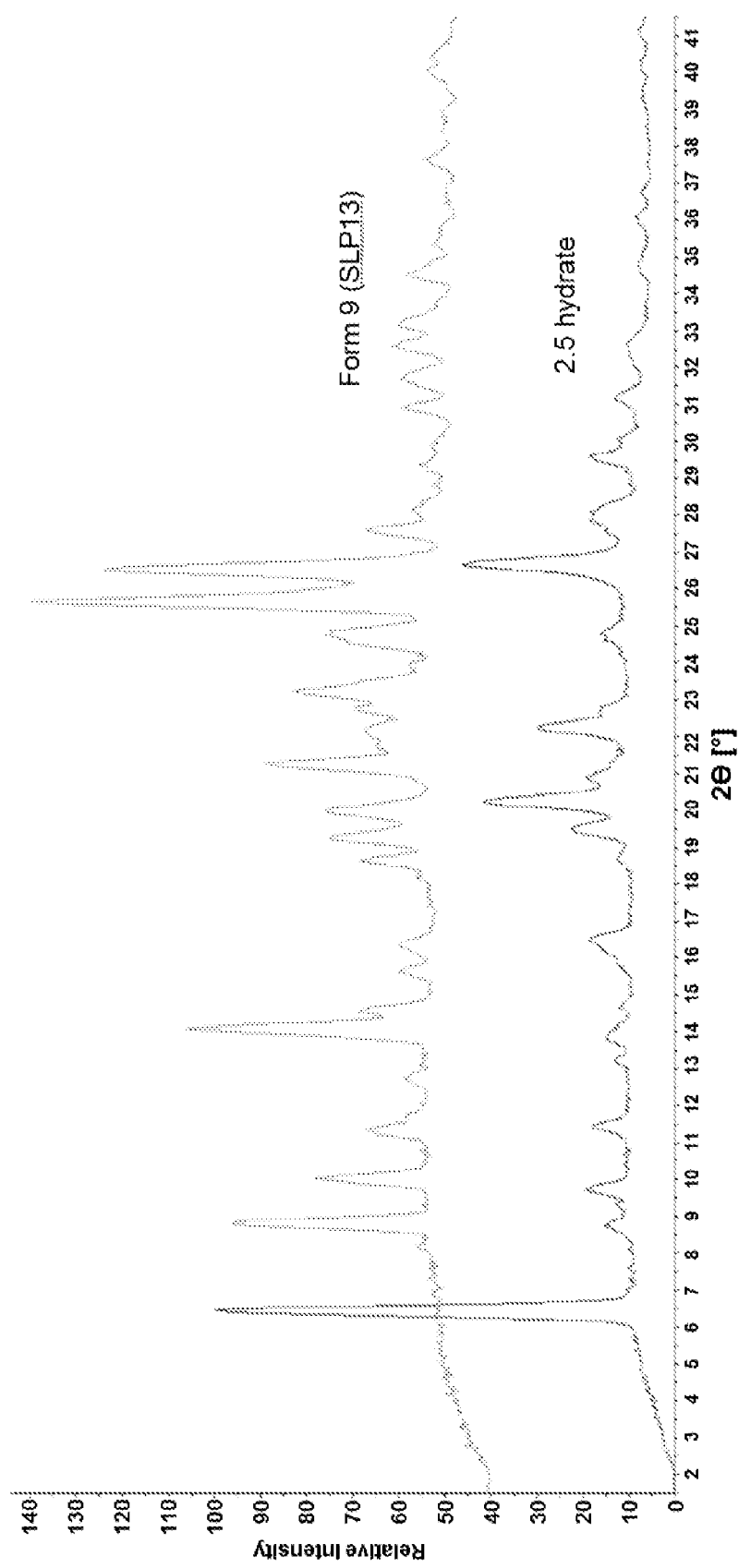

FIG. 37 depicts an overlay of HT-XRPD patterns (from bottom to top) 3-[2-butyl-1-(2-diethylamino-ethyl)-1H-benzoimidazol-5-yl]-N-hydroxy-acrylamide dihydrochloride 2.5 hydrate Form 3 and 3-[2-butyl-1-(2-diethylamino-ethyl)-1H-benzoimidazol-5-yl]-N-hydroxy-acrylamide dihydrochloride anhydrous Form 9. Form 9 was identified in several experiments performed on Form 1 and Form 3 in ethanol absolute or extra dry.

Figure 38:
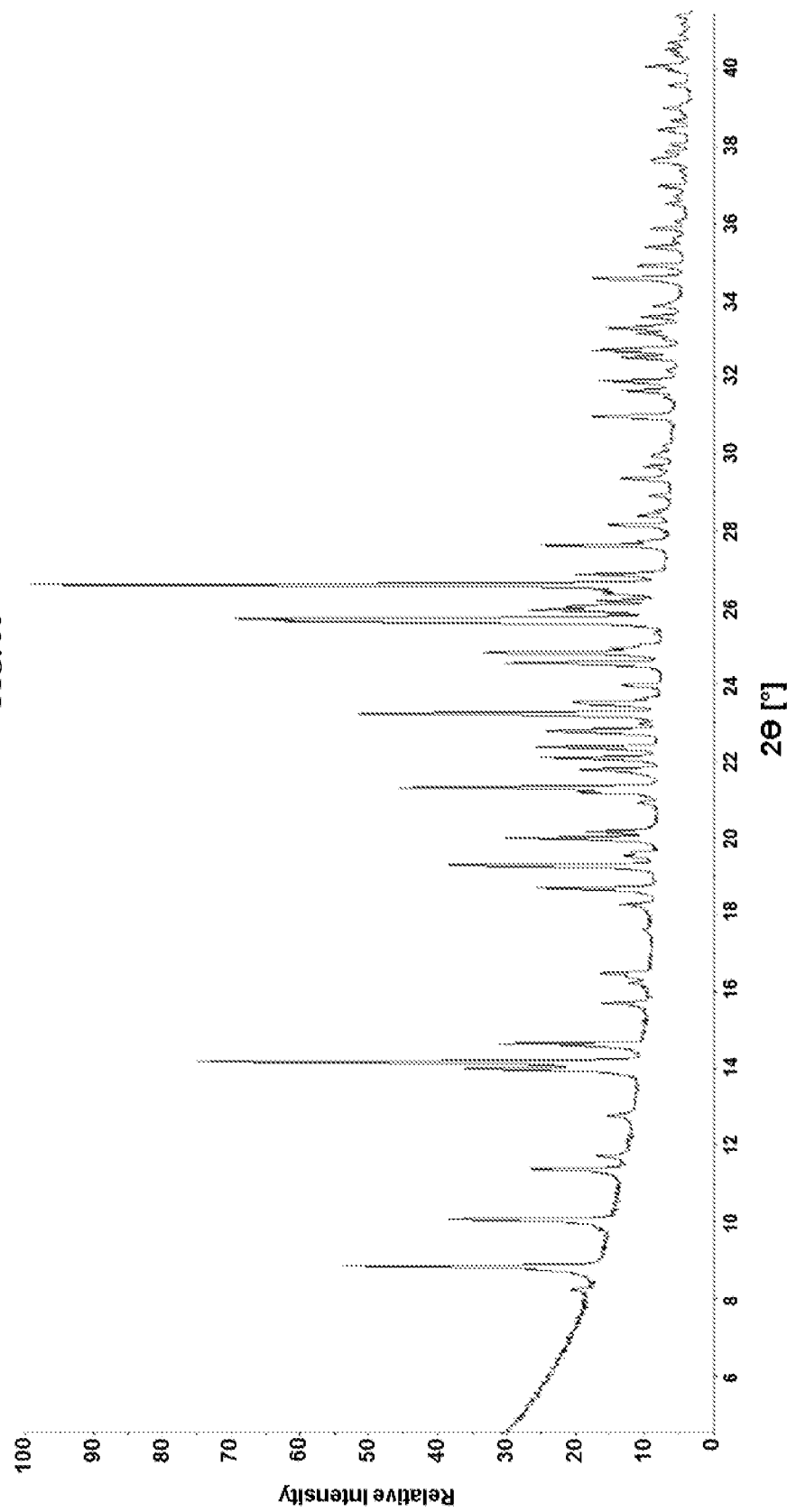

FIG. 38 depicts the high resolution XRPD pattern of the anhydrous Form 9 as obtained in the slurry conversion experiment in ethanol extra dry.

Figure 39:
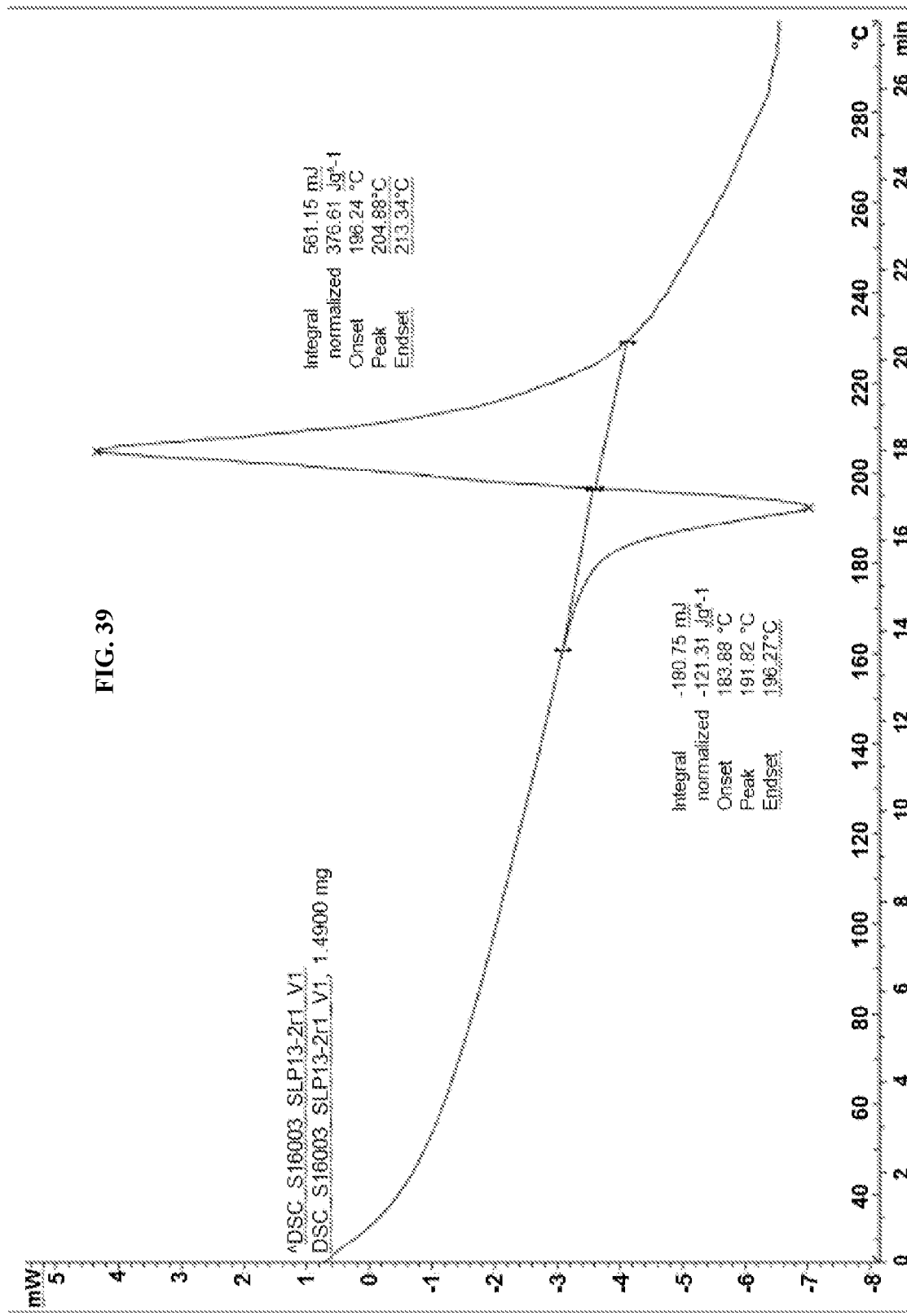

FIG. 39 depicts DSC analysis (with a heating rate of 10° C./min) of 3-[2-butyl-1-(2-diethylamino-ethyl)-1H-benzoimidazol-5-yl]-N-hydroxy-acrylamide dihydrochloride anhydrous Form 9. One single endotherm was observed at 191.8° C. followed by an exothermic event follows at 204.9° C. attributed to the thermal decomposition of the hydrochloride salt.

Figure 40A:
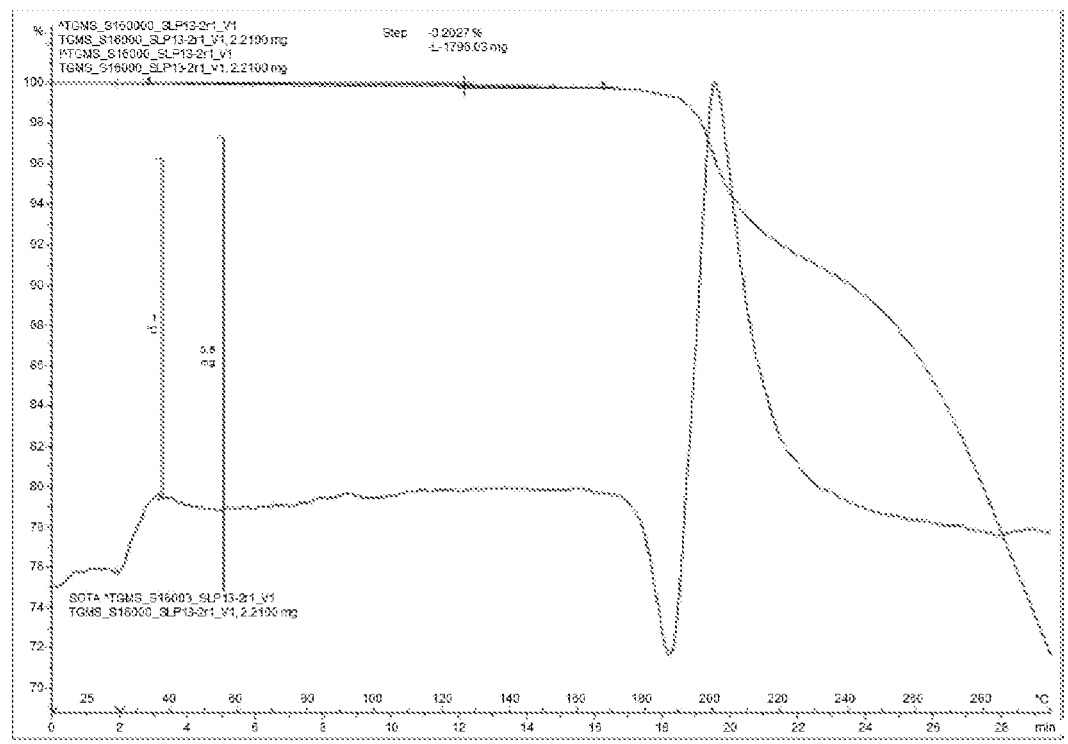

FIG. 40A depicts the TGA/SDTA analysis of 3-[2-butyl-1-(2-diethylamino-ethyl)-1H-benzoimidazol-5-yl]-N-hydroxy-acrylamide dihydrochloride anhydrous Form 9.

Figure 40B:
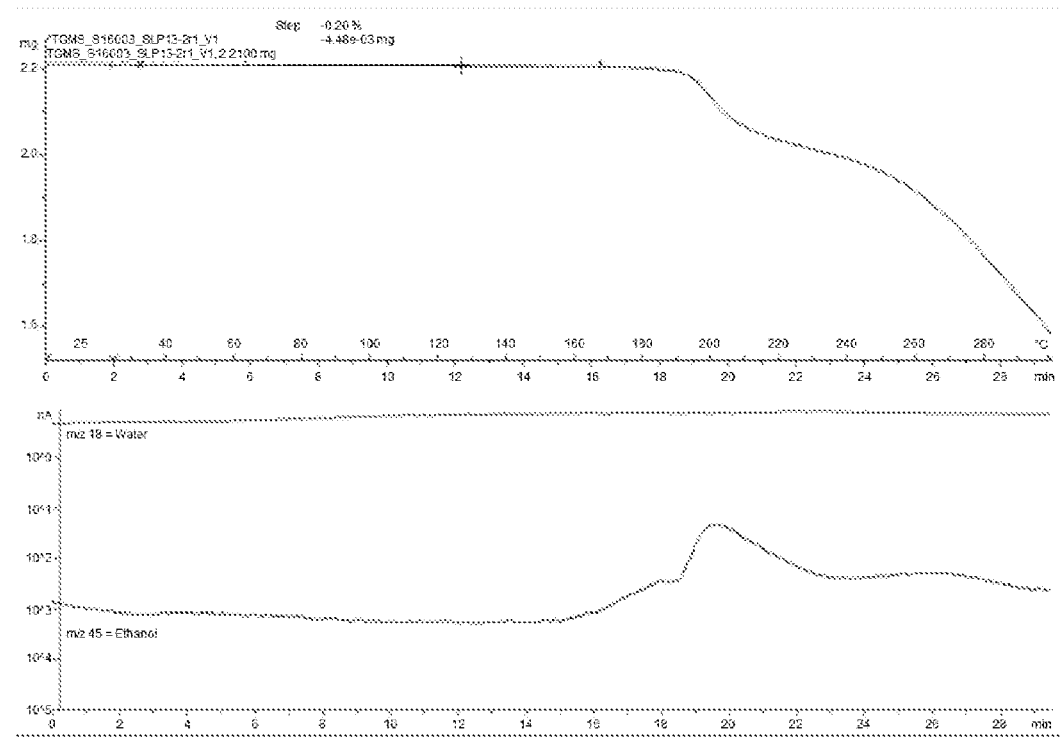

FIG. 40B depicts the TGMS analysis of 3-[2-butyl-1-(2-diethylamino-ethyl)-1H-benzoimidazol-5-yl]-N-hydroxy-acrylamide dihydrochloride anhydrous Form 9.

Figure 41:
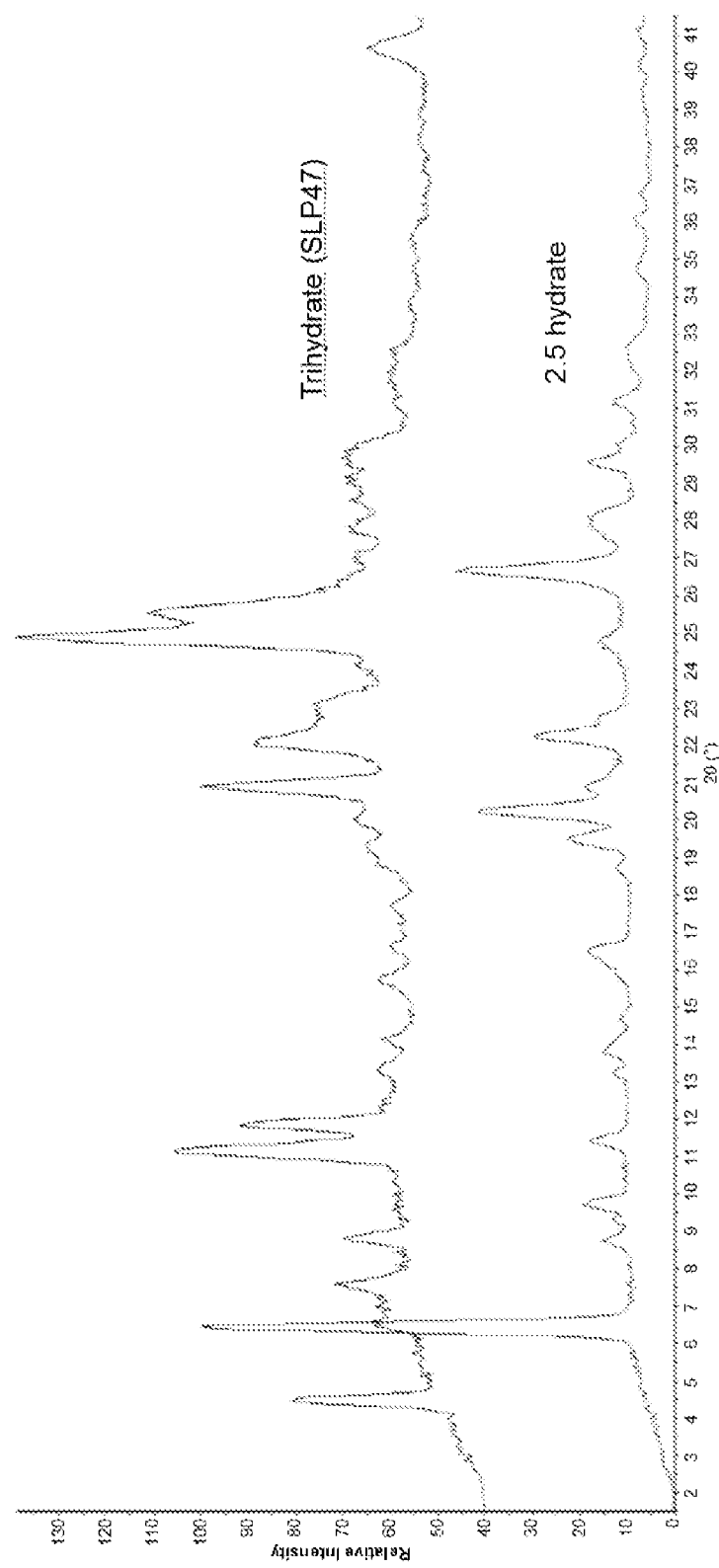

FIG. 41 depicts an overlay of HT-XRPD patterns (from bottom to top): Form 3 and Form 2 as obtained after slurry conversion experiment on Form 1 in methanol/water (75/25) at 50° C.

Figure 42:
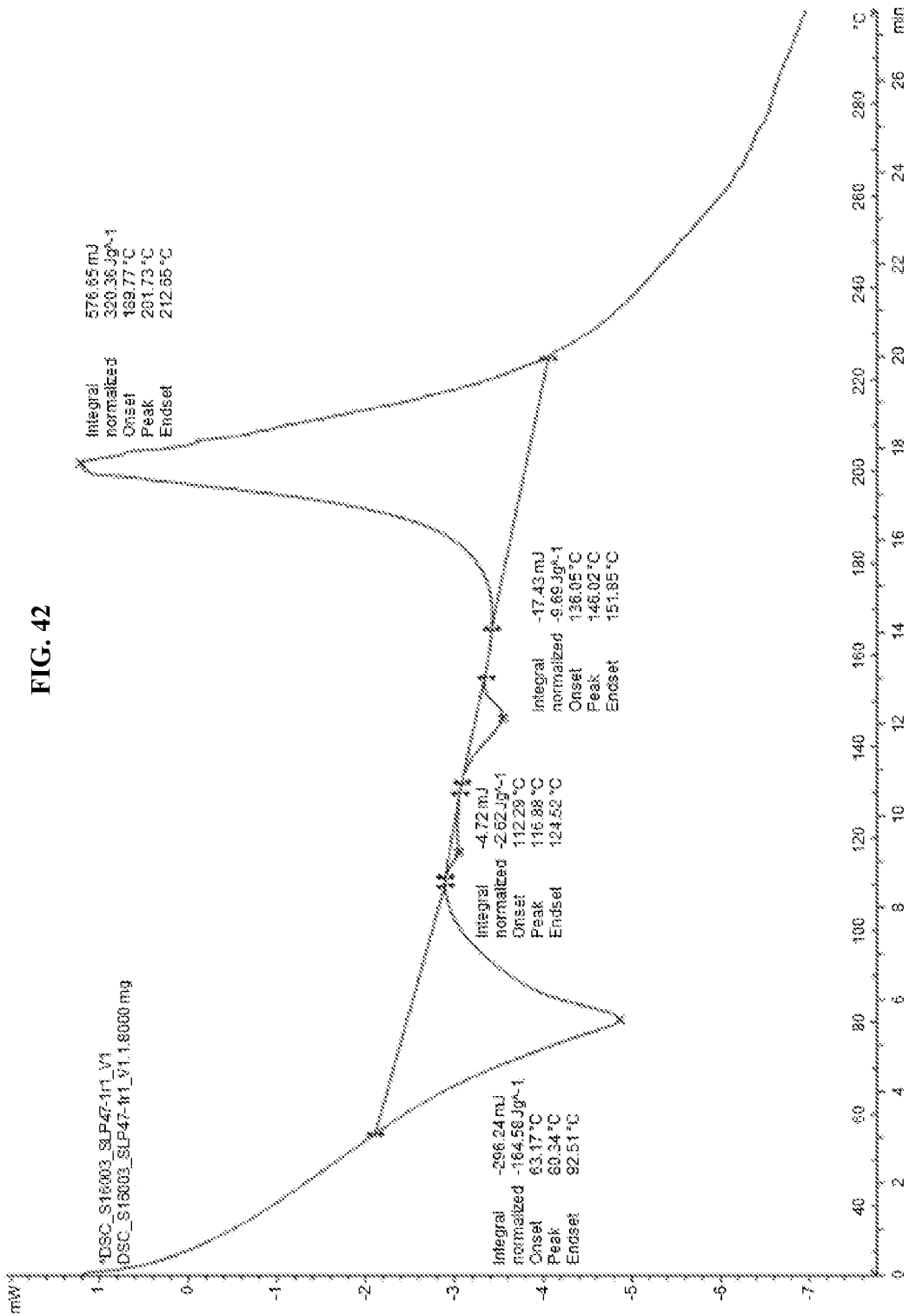

FIG. 42 depicts DSC analysis (with a heating rate of 10° C./min) of Form 2.

Figure 43A:
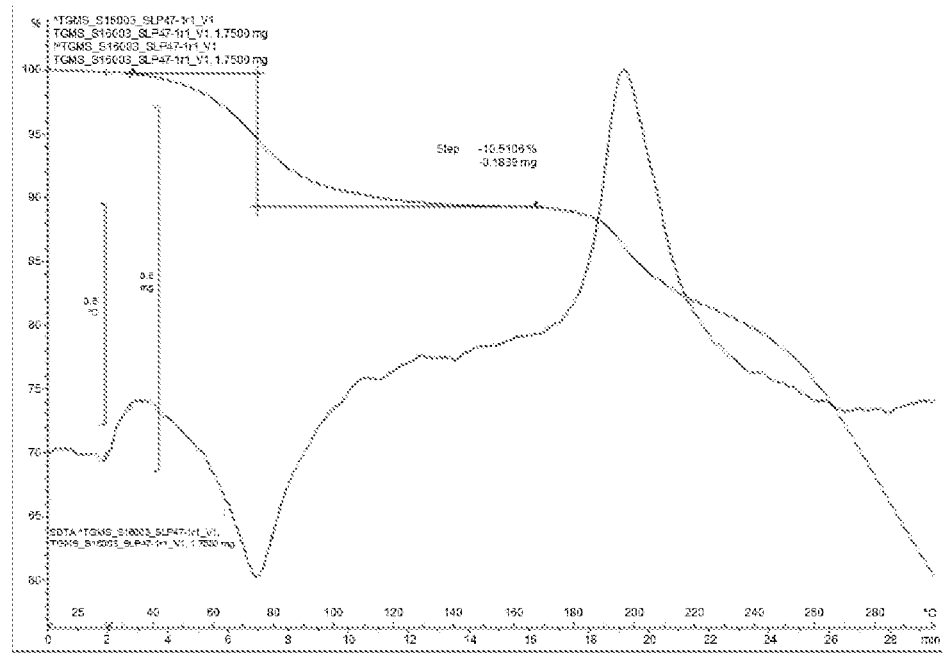

FIG. 43A depicts the TGA/SDTA analysis of 3-[2-butyl-1-(2-diethylamino-ethyl)-1H-benzoimidazol-5-yl]-N-hydroxy-acrylamide dihydrochloride trihydrate Form 2.

Figure 43B:
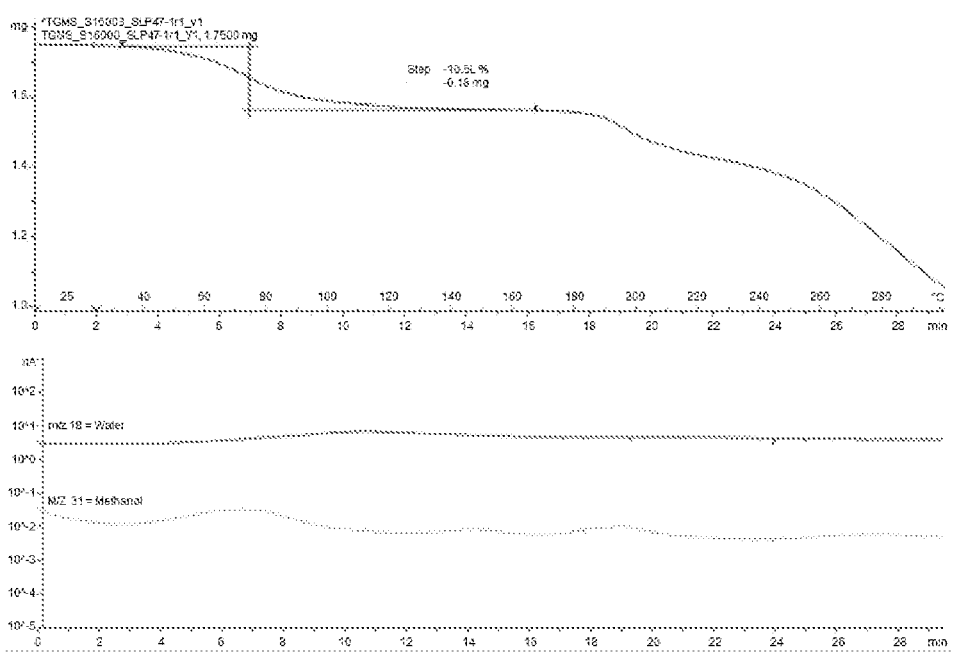

FIG. 43B depicts the TGMS analysis of 3-[2-butyl-1-(2-diethylamino-ethyl)-1H-benzoimidazol-5-yl]-N-hydroxy-acrylamide dihydrochloride trihydrate Form 2.

Figure 44:
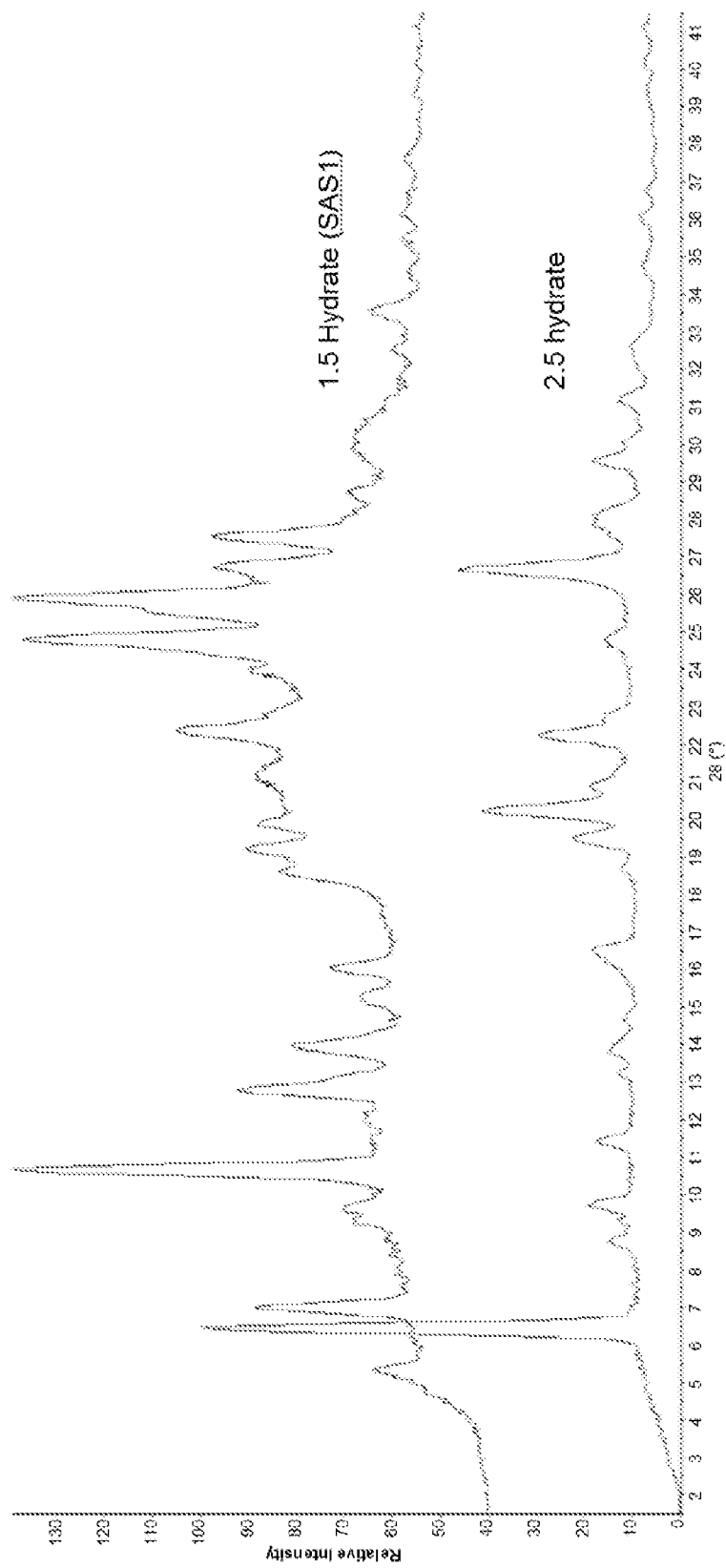

FIG. 44 depicts an overlay of HT-XRPD patterns (from bottom to top): Form 3 and Form 4 as obtained upon slurry Form 3 in ethanol at ambient conditions for 2 hours.

Figure 45:
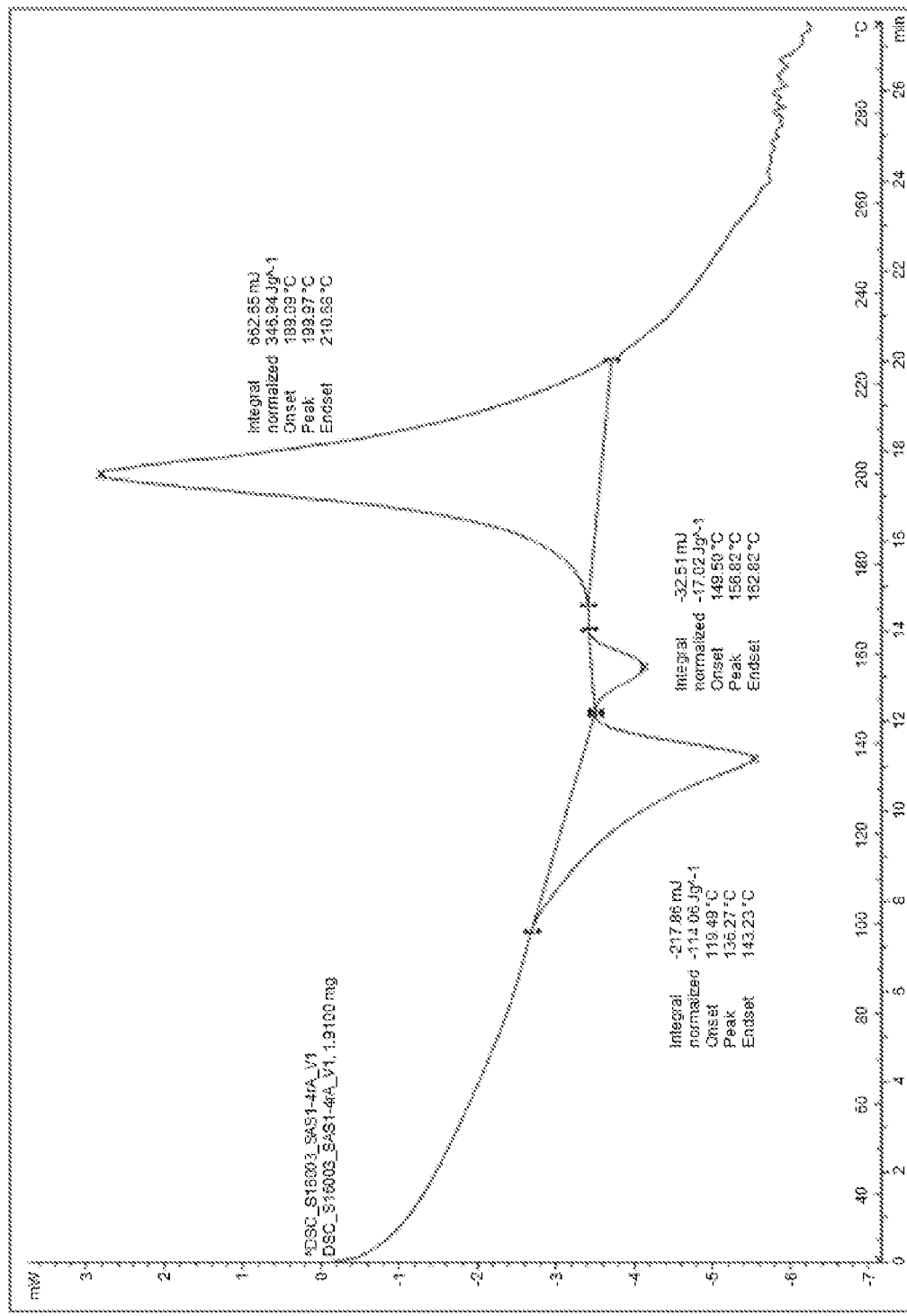

FIG. 45 depicts DSC analysis (with a heating rate of 10° C./min) of 3-[2-butyl-1-(2-diethylamino-ethyl)-1H-benzoimidazol-5-yl]-N-hydroxy-acrylamide dihydrochloride 1.5 hydrate Form 4.

Figure 46A:
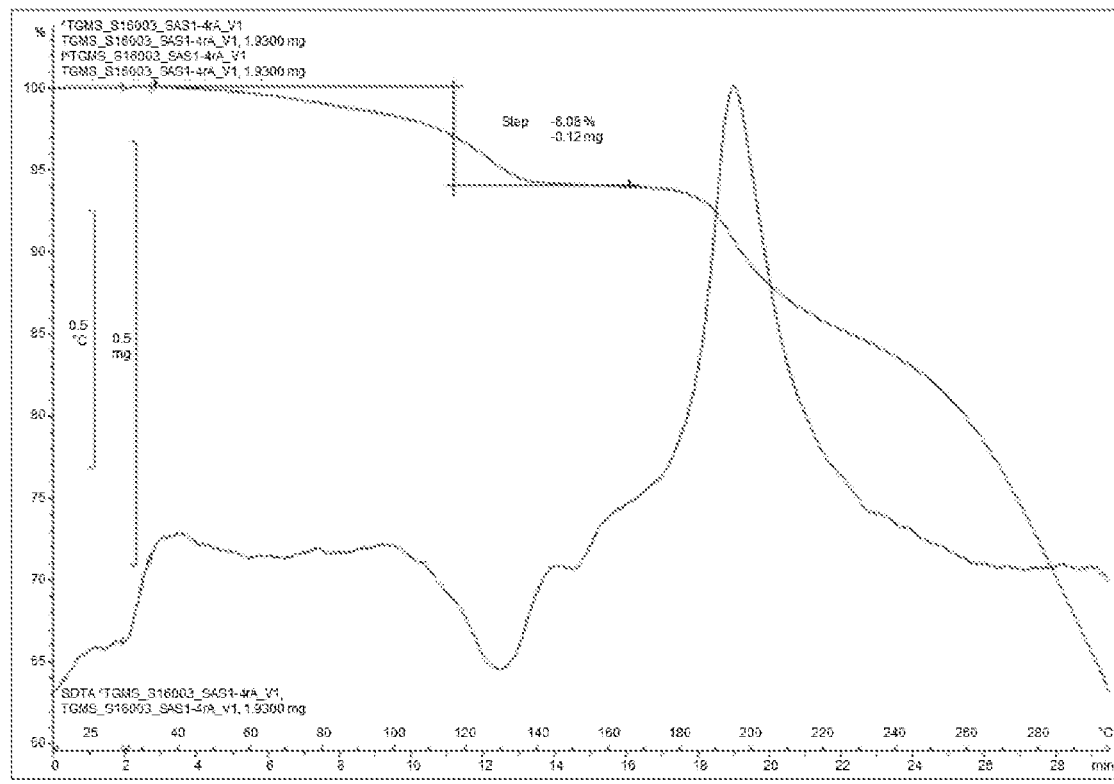

FIG. 46A depicts the TGA/SDTA analysis of 3-[2-butyl-1-(2-diethylamino-ethyl)-1H-benzoimidazol-5-yl]-N-hydroxy-acrylamide dihydrochloride 1.5 hydrate Form 4.

Figure 46B:
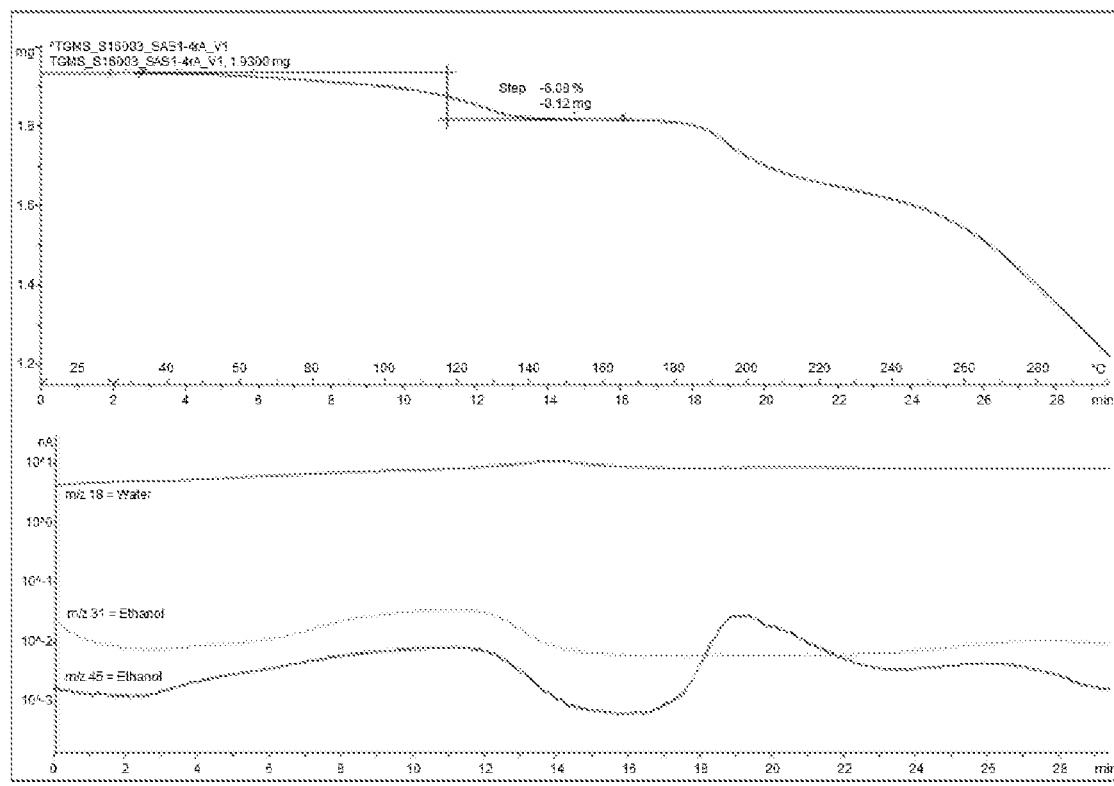

FIG. 46B depicts the TGMS analysis of 3-[2-butyl-1-(2-diethylamino-ethyl)-1H-benzoimidazol-5-yl]-N-hydroxy-acrylamide dihydrochloride 1.5 hydrate Form 4.

Figure 47:
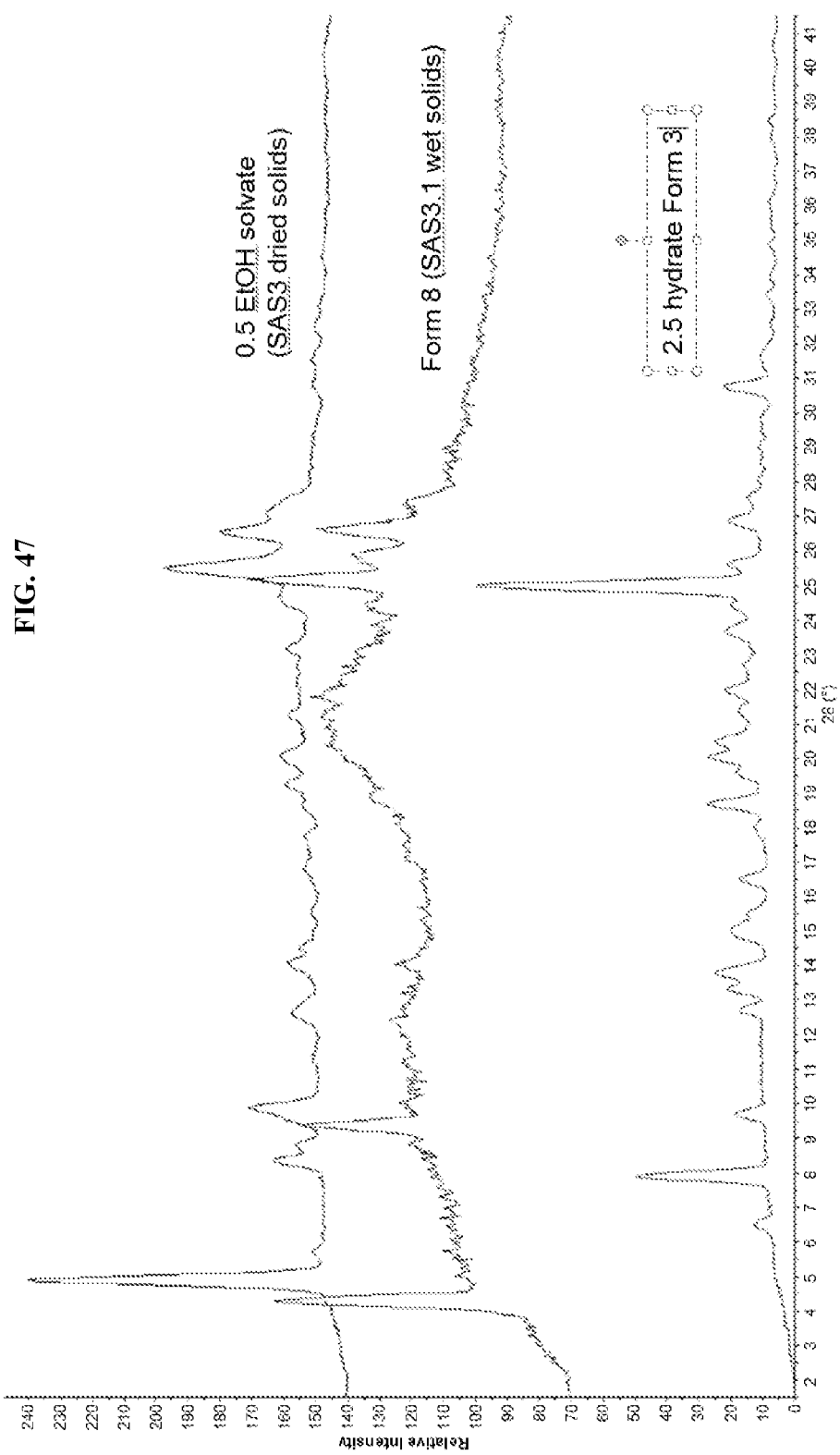

FIG. 47 depicts an overlay of HT-XRPD patterns (from bottom to top) Form 3, Form 8 as obtained in the wet solid after 20 hours slurry of 2.5 hydrate Form 3 in ethanol absolute at ambient conditions and 0.5 EtOH solvate (Form 7) after drying the wet solids for 2 hours at 10 mbar.

Figure 48A:
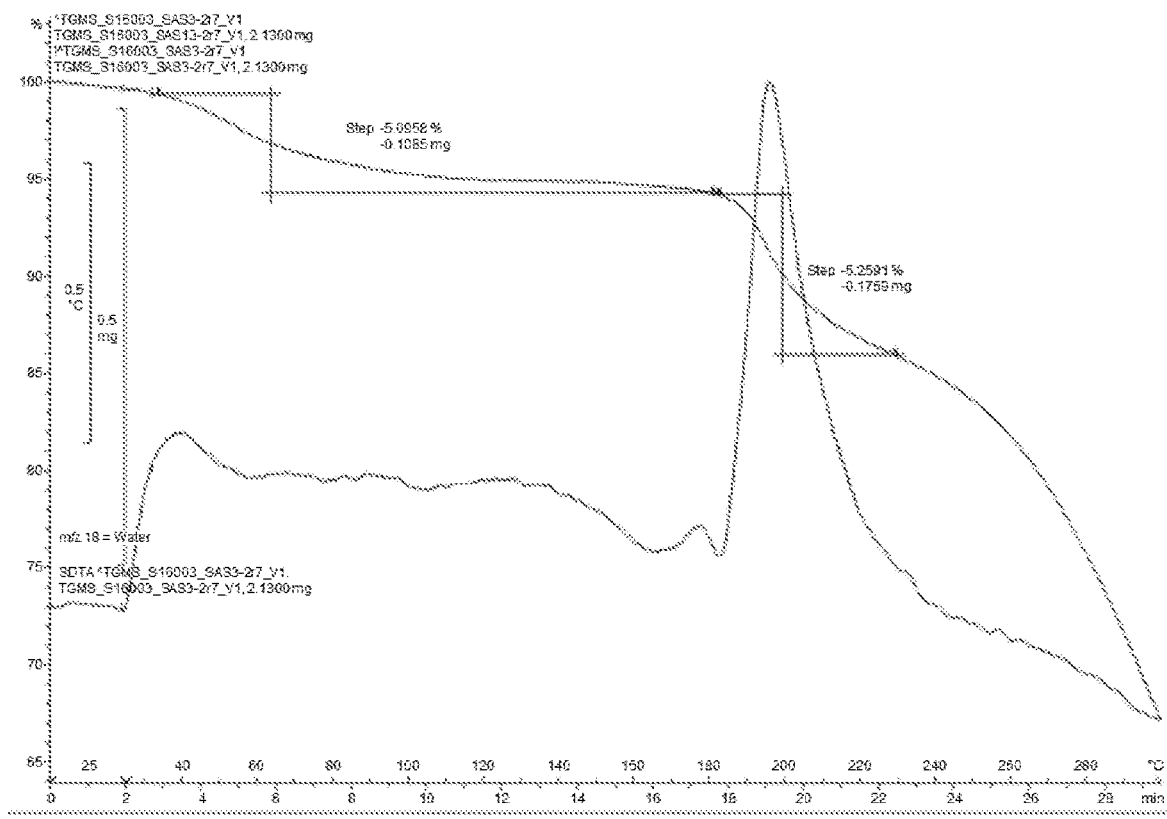

FIG. 48A depicts the TGA/SDTA analysis of 3-[2-butyl-1-(2-diethylamino-ethyl)-1H-benzoimidazol-5-yl]-N-hydroxy-acrylamide dihydrochloride 0.5 EtOH solvate (Form 7).

Figure 48B:
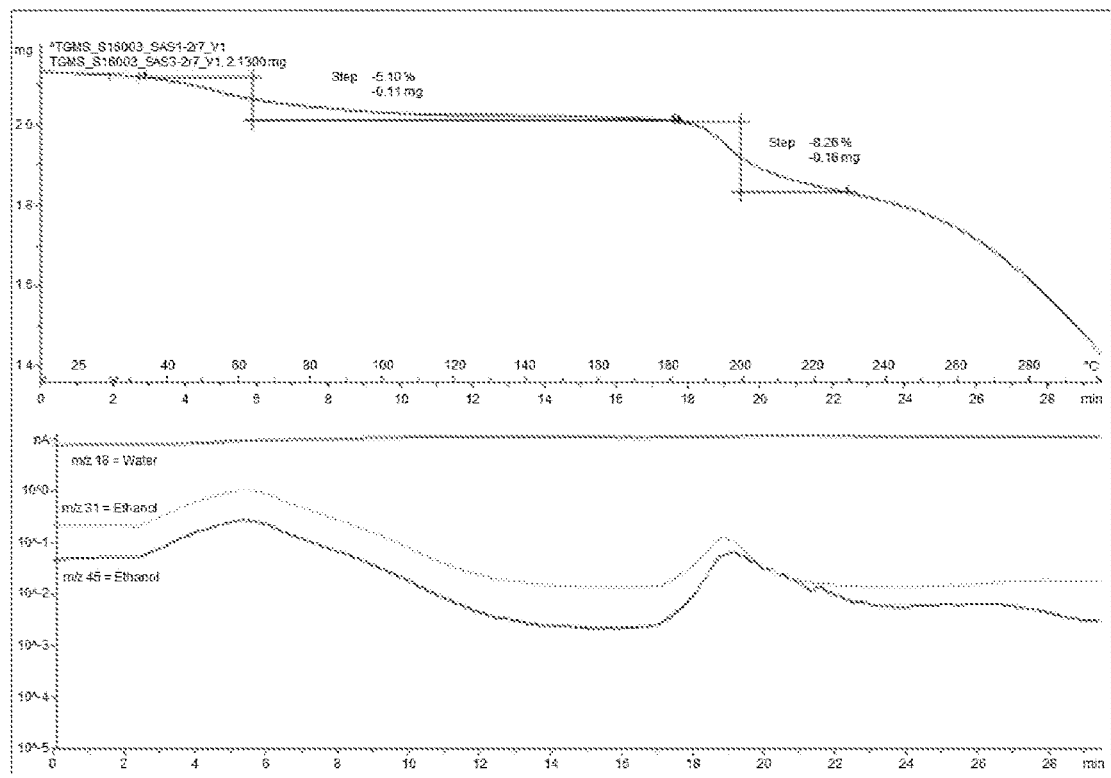

FIG. 48B depicts the TGMS analysis of 3-[2-butyl-1-(2-diethylamino-ethyl)-1H-benzoimidazol-5-yl]-N-hydroxy-acrylamide dihydrochloride 0.5 EtOH solvate (Form 7).

Figure 49:
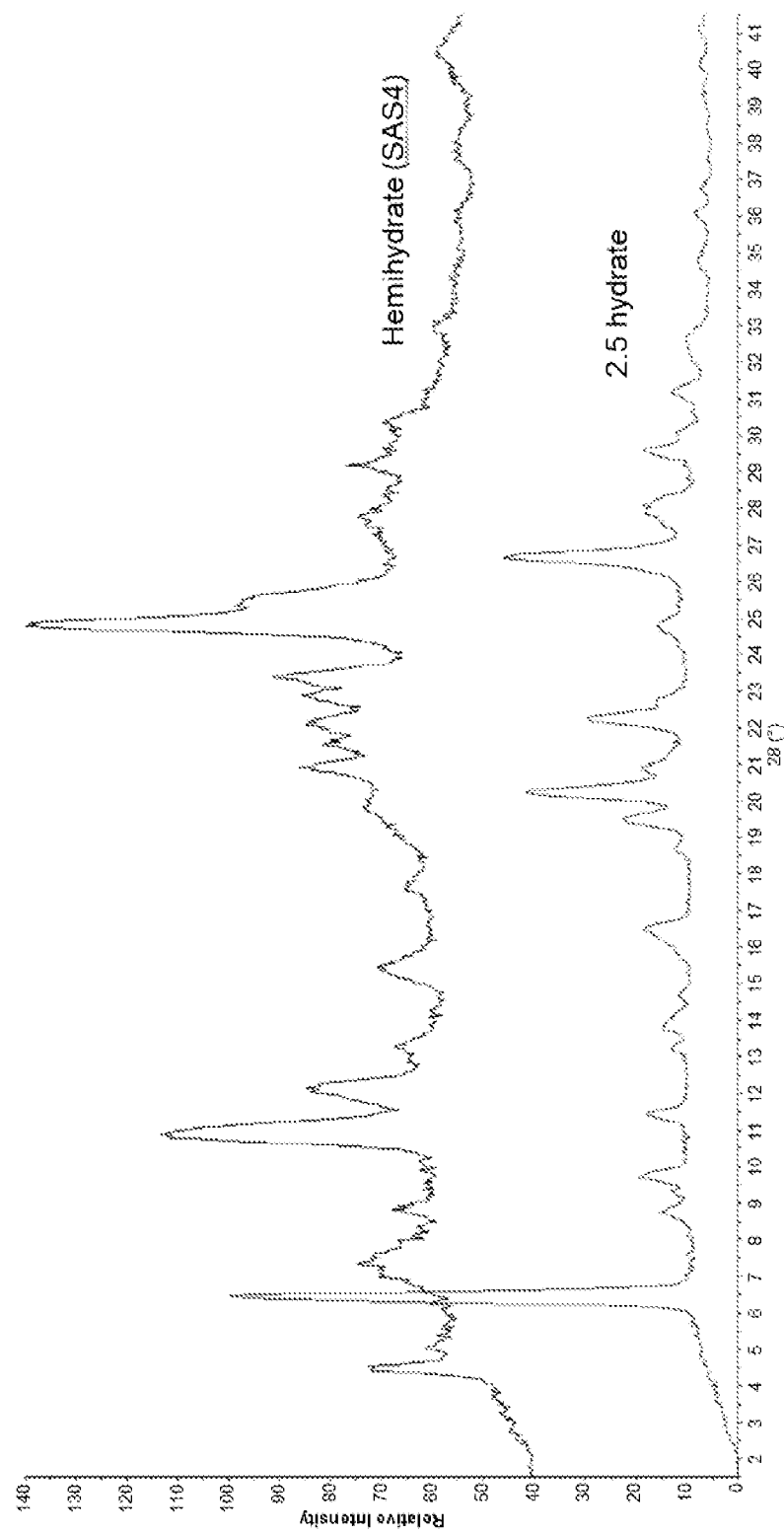

FIG. 49 depicts an overlay of HT-XRPD patterns (from bottom to top) Form 3 and Form 10. This form was obtained by freeze drying a water solution.

Figure 50:
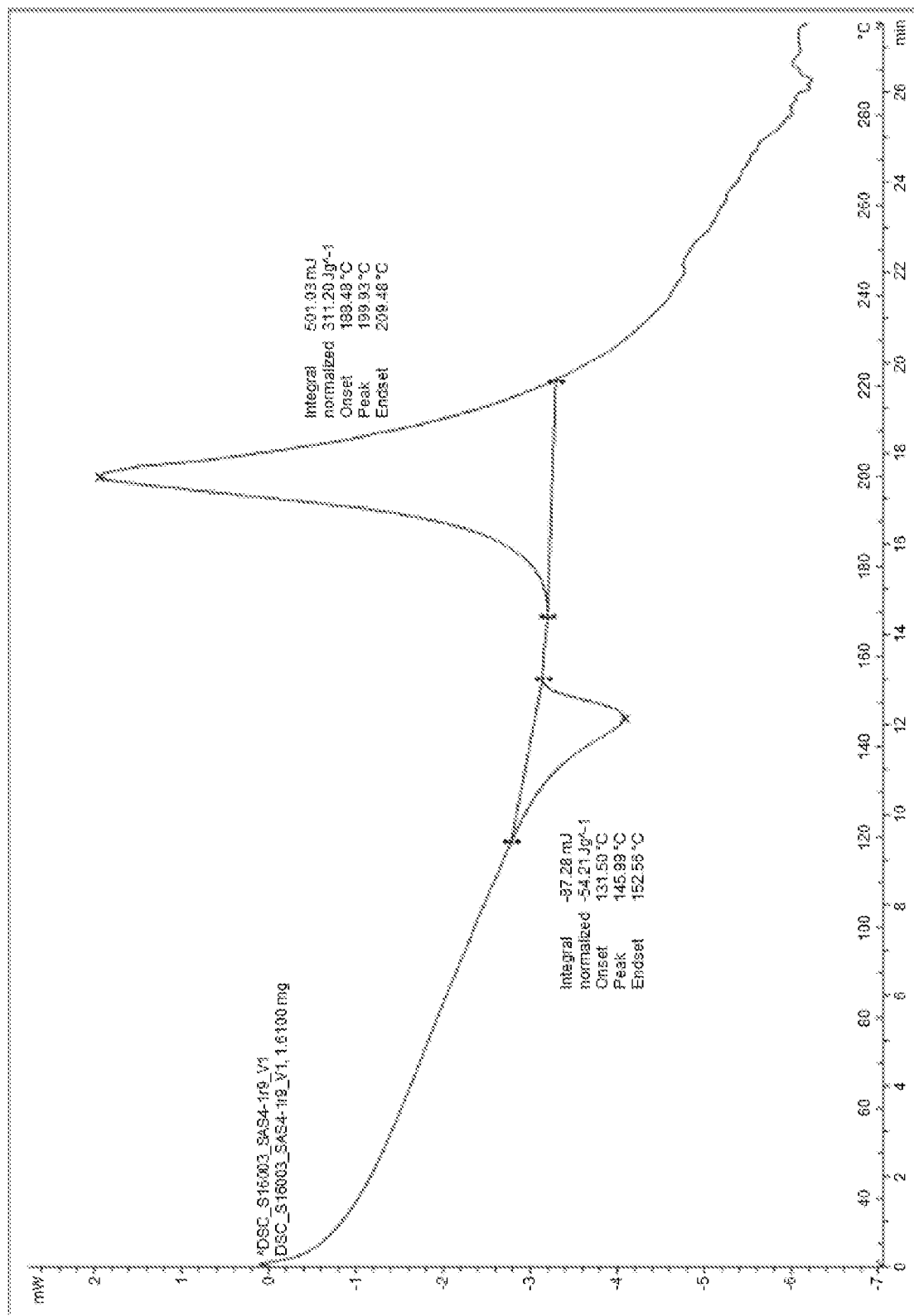

FIG. 50 depicts DSC analysis (with a heating rate of 10° C./min) of Form 10. A first endotherm is observed at 146.0° C. followed by an exothermic event at 199.9° C. which might be attributed to the thermal decomposition of the hydrochloride salt.

Figure 51A:
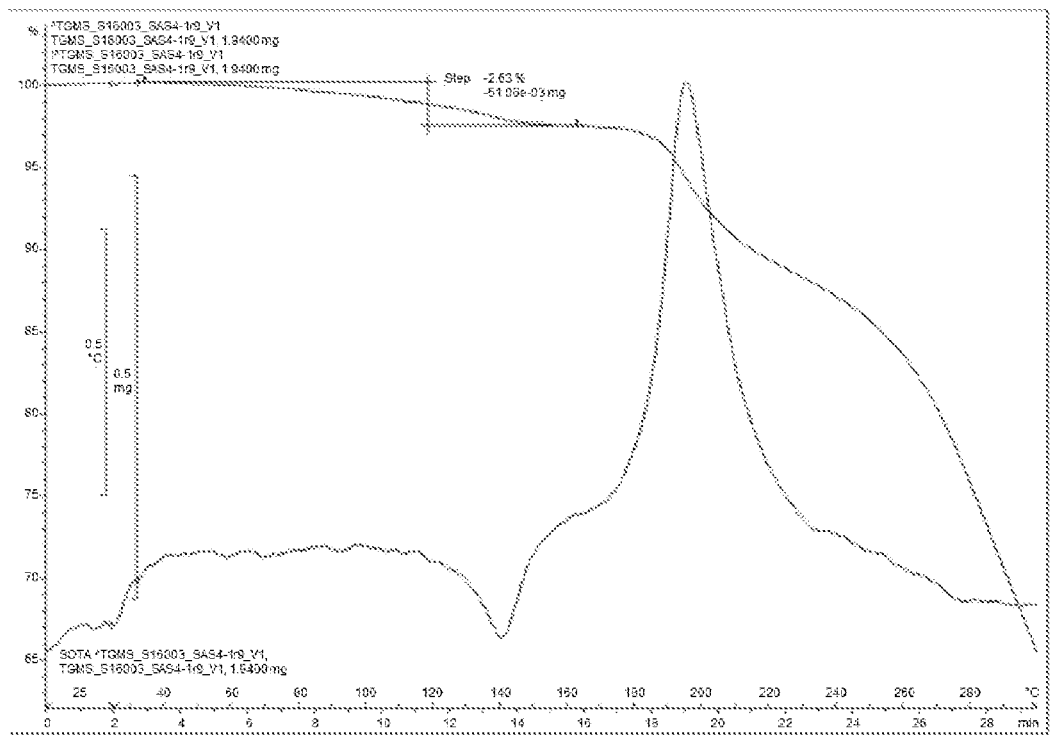
Figure 51B:
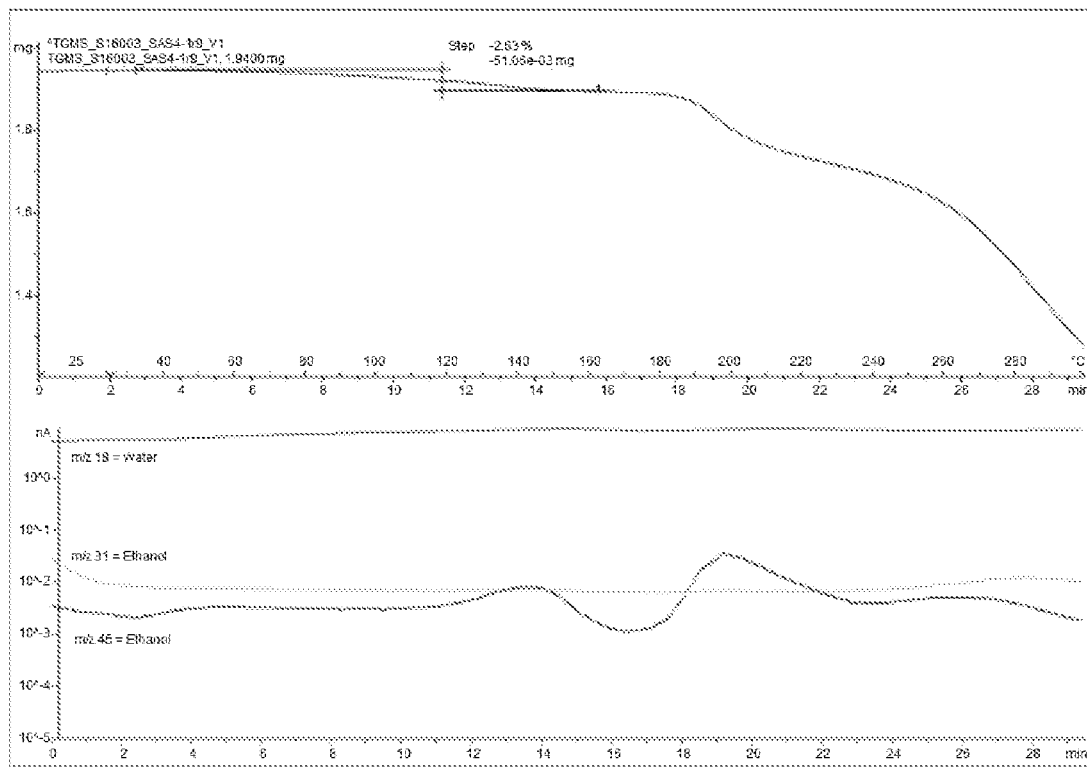

FIG. 51A depicts the TGA/SDTA analysis of Form 10.
FIG. 51B depicts the TGMS analysis of Form 10.

Figure 52:
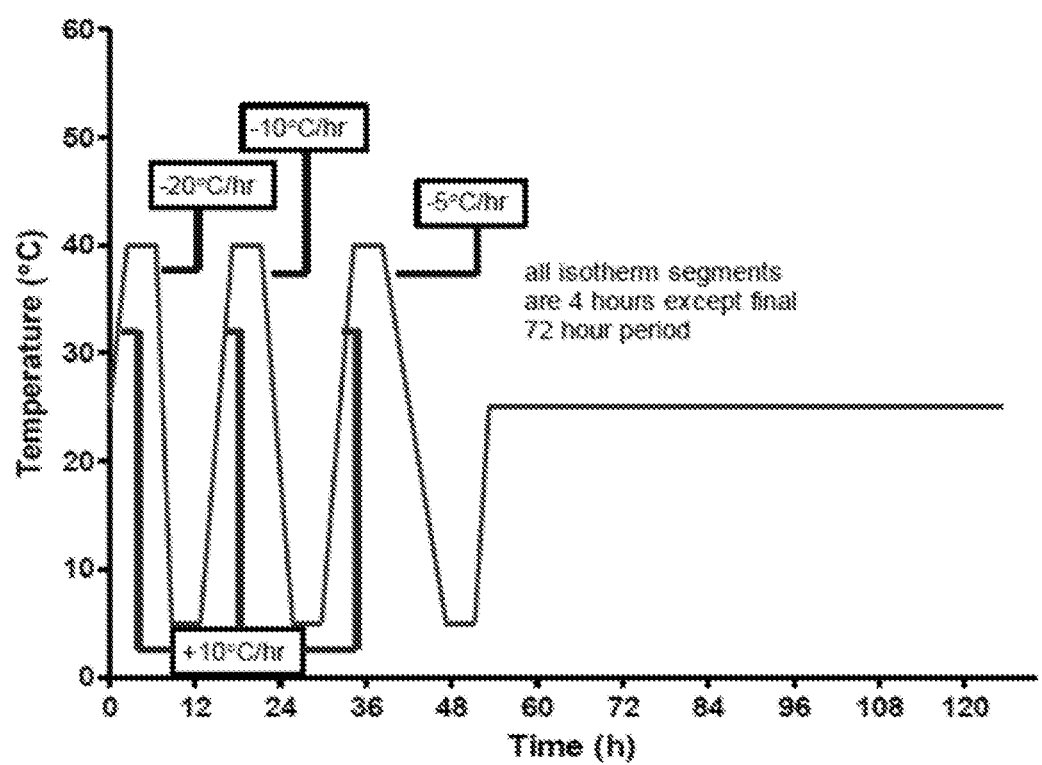

FIG. 52 depicts the temperature profile of the thermocycling experiments.

DETAILED DESCRIPTION OF THE INVENTION

Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the term "about" refers to ±10% of a stated number or value. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

The term "patient", as used herein in reference to individuals suffering from a disease or disorder, and the like, encompasses mammals and non-mammals. In some embodiments, the mammal is a human.

The term "subject", as used herein in reference to individuals administered a compound or composition as described herein, encompasses mammals and non-mammals. In some embodiments, the mammal is human.

The terms "effective amount", "therapeutically effective amount" or "pharmaceutically effective amount" as used herein, refer to an amount of at least one agent or compound being administered that is sufficient to treat or prevent the particular disease or condition. The result is the reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case is determined using techniques such as a dose escalation study.

A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

A "synergistically effective" therapeutic amount of an agent or therapy is an amount which, when combined with an effective or sub-therapeutic amount of another agent or therapy, produces a greater effect than when either of the two agents are used alone. In some embodiments, a synergistically effective therapeutic amount of an agent or therapy produces a greater effect when used in combination than the additive effects of each of the two agents or therapies when used alone. The term "greater effect" encompasses not only a reduction in symptoms of the disorder to be treated, but also an improved side effect profile, improved tolerability, improved patient compliance, improved efficacy, or any other improved clinical outcome.

The terms "synergistic" and "synergistically" as applied to the effect of two or more pharmaceutically active ingredients used in combination (whether simultaneously or sequentially) refer to a greater effect than when either of the two agents are used alone.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present invention, whether radioactive or not, are encompassed within the scope of the present invention. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art or by processes analogous to those described in the Schemes and Examples herein using appropriate isotopically-enriched reagents and/or intermediates. In some embodiments, the compounds described herein contain one or more isotopic variants (e.g., deuterium, tritium, $^{13}$C, and/or $^{14}$C).

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH.

"Pharmaceutically acceptable salt" includes both acid and base addition salts. A pharmaceutically acceptable salt of any one of the substituted steroidal derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

In the context of the present specification, the term "therapy" also includes "prophylaxis" unless there are specific indications to the contrary. The terms "therapeutic" and "therapeutically" should be construed accordingly.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

The term "substantially the same as" as used herein, refers to a powder X-ray diffraction pattern, DSC thermogram, TGA/SDTA pattern or TGMS pattern that is identical or non-identical to those depicted herein, but that falls within the limits of experimental error, when considered by one of ordinary skill in the art.

The term "substantially similar to" as used herein, refers to a powder X-ray diffraction pattern, DSC thermogram, TGA/SDTA pattern or TGMS pattern that is non-identical to those depicted herein, and shares a majority of major peaks, which fall within the limits of experimental error, when considered by one of ordinary skill in the art.

Polymorphs

The present invention relates to polymorphic forms of 3-[2-butyl-1-(2-diethylamino-ethyl)-1H-benzoimidazol-5-yl]-N-hydroxy-acrylamide, which is known to modulate histone deacetylase (HDAC) activities.

Figure 16:
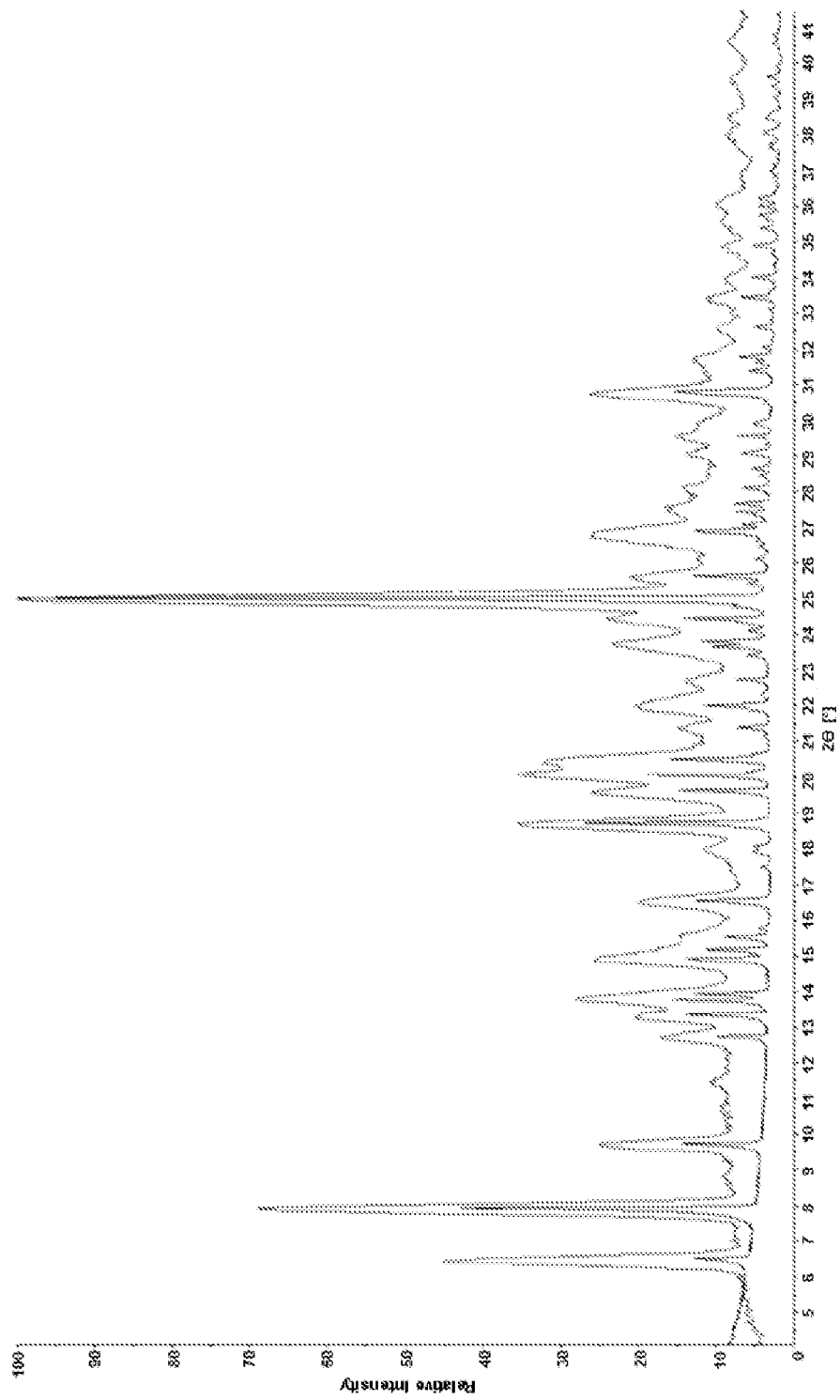
FIG. 16 depicts HR-XRPD pattern of 3-[2-butyl-1-(2-diethylamino-ethyl)-1H-benzoimidazol-5-yl]-N-hydroxy-acrylamide dihydrochloride monohydrate (Form 1) as obtained in the scale-up experiment (bottom) and 3-[2-butyl-1-(2-diethylamino-ethyl)-1H-benzoimidazol-5-yl]-N-hydroxy-acrylamide dihydrochloride monohydrate as a reference material (top).
Figure 17:
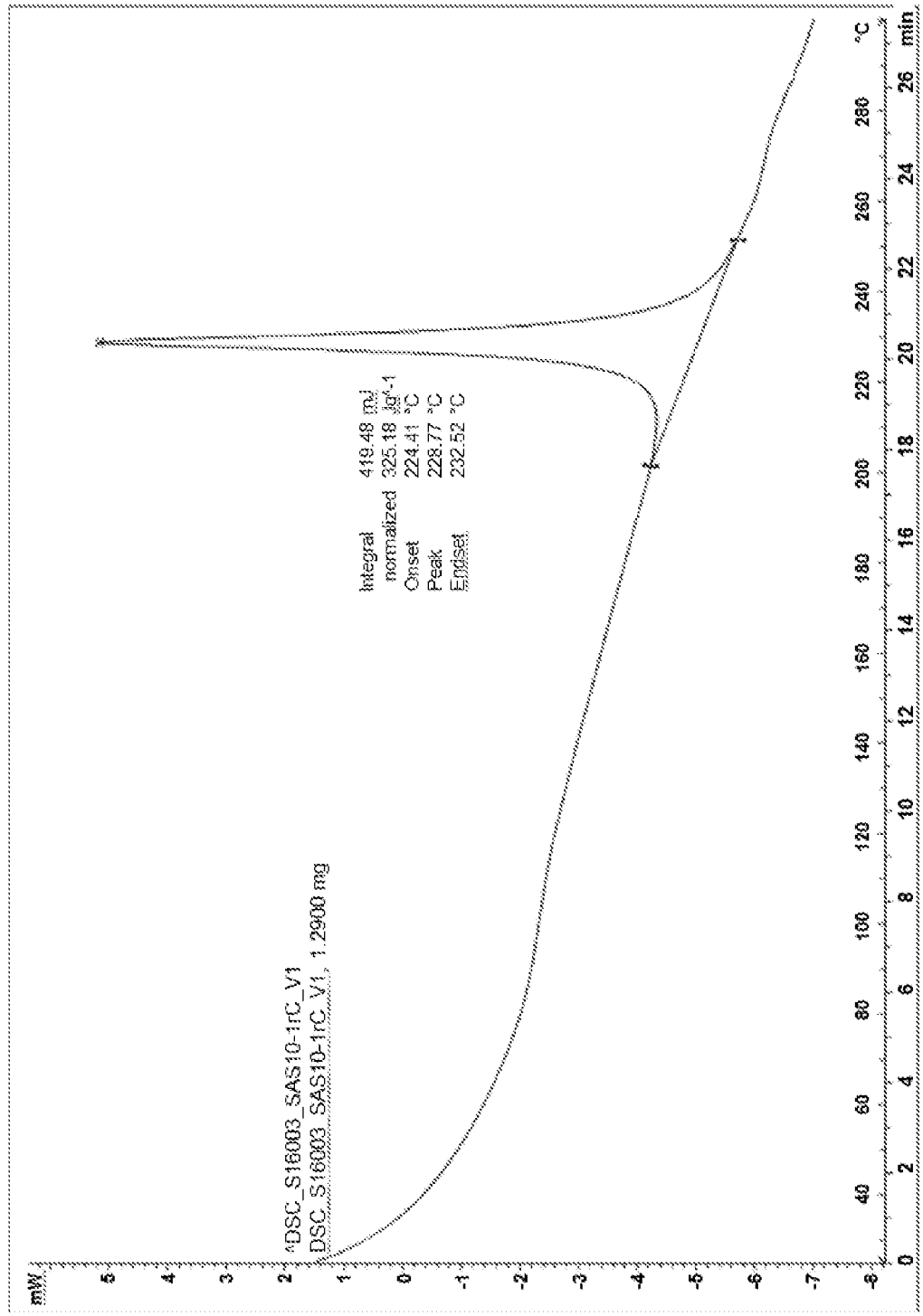
FIG. 17 depicts DSC analysis (with heating rate of 10° C./min) of 3-[2-butyl-1-(2-diethylamino-ethyl)-1H-benzoimidazol-5-yl]-N-hydroxy-acrylamide dihydrochloride monohydrate (Form 1).
Figure 18A:
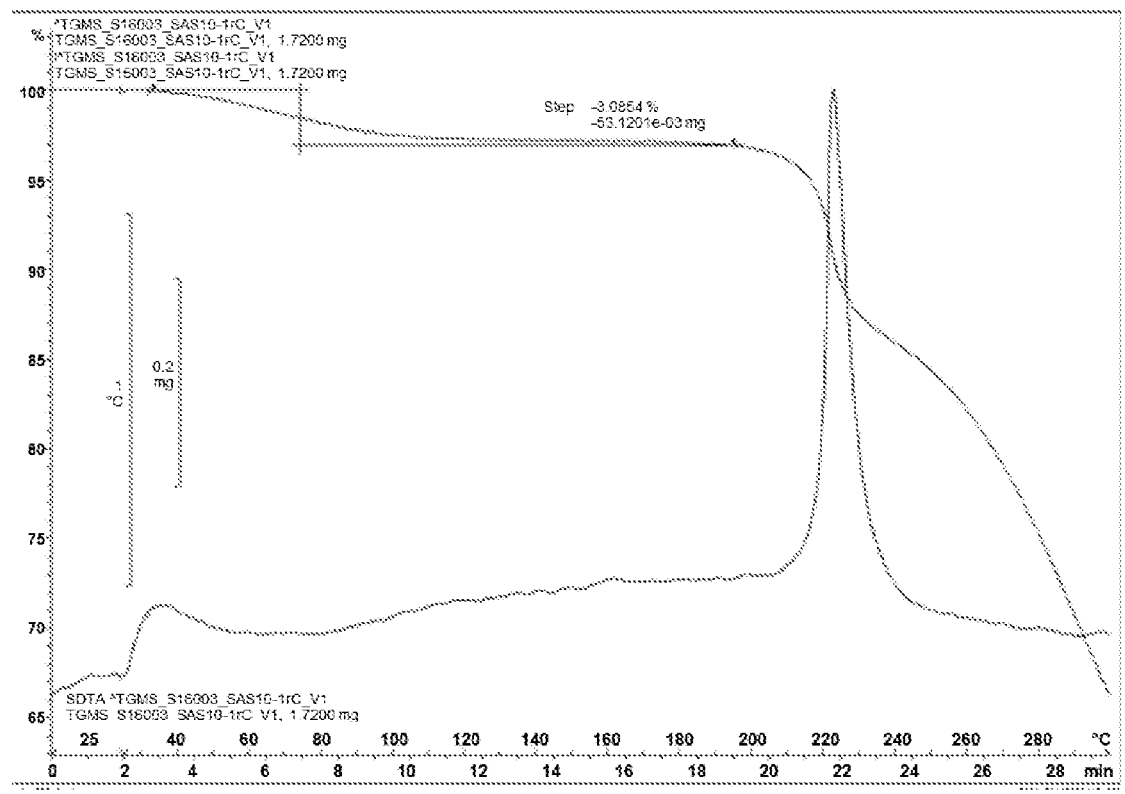
FIG. 18A depicts the TGA/SDTA analysis (with heating rate of 10° C./min) of 3-[2-butyl-1-(2-diethylamino-ethyl)-1H-benzoimidazol-5-yl]-N-hydroxy-acrylamide dihydrochloride monohydrate (Form 1).
Figure 18B:
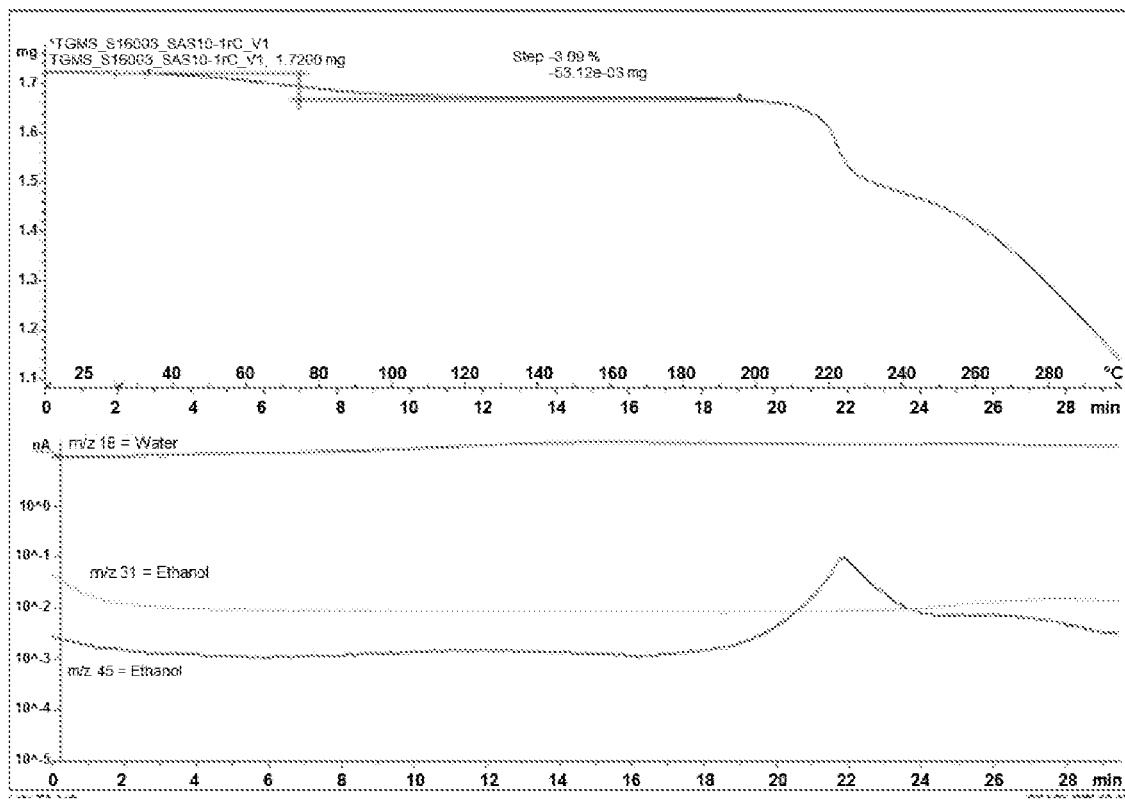
FIG. 18B depicts the TGMS analysis (with heating rate of 10° C./min) of 3-[2-butyl-1-(2-diethylamino-ethyl)-1H-benzoimidazol-5-yl]-N-hydroxy-acrylamide dihydrochloride monohydrate (Form 1).

The term "polymorph Form 1" or "Form 1" refers to a crystalline form of 3-[2-butyl-1-(2-diethylamino-ethyl)-1H-benzoimidazol-5-yl]-N-hydroxy-acrylamide dihydrochloride monohydrate that exhibits an X-ray powder diffraction pattern substantially the same as that shown in FIG. 16, and/or FIG. 34 and/or a DSC thermogram substantially the same as that shown in FIG. 17 and/or a TGA/SDTA trace substantially the same as that shown in FIG. 18A and/or a TGMS trace substantially the same as that shown in FIG. 18B.

Figure 1:
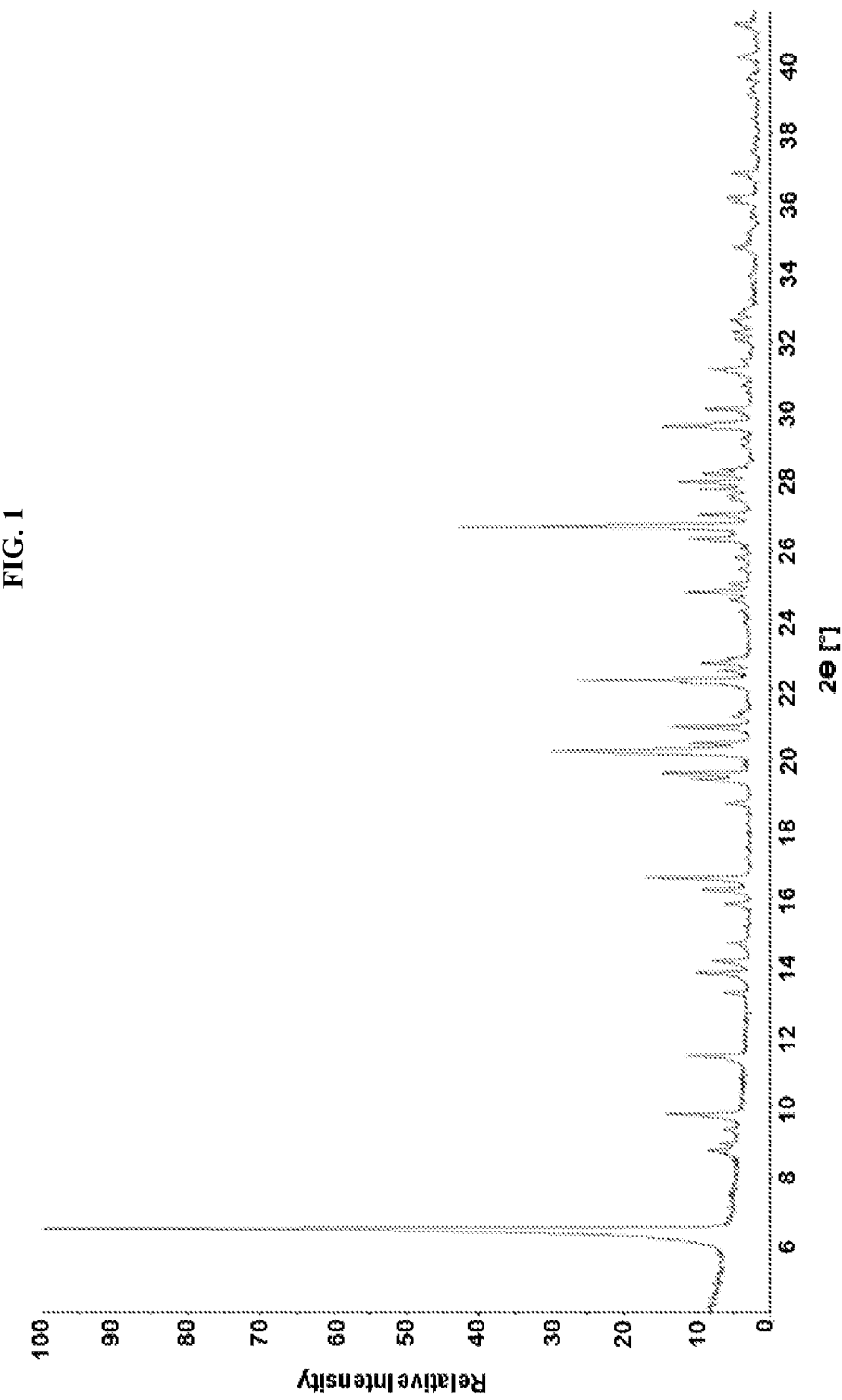
FIG. 1 depicts the HR-XRPD pattern of 3-[2-butyl-1-(2-diethylamino-ethyl)-1H-benzoimidazol-5-yl]-N-hydroxy-acrylamide dihydrochloride 2.5 hydrate.
Figure 2:
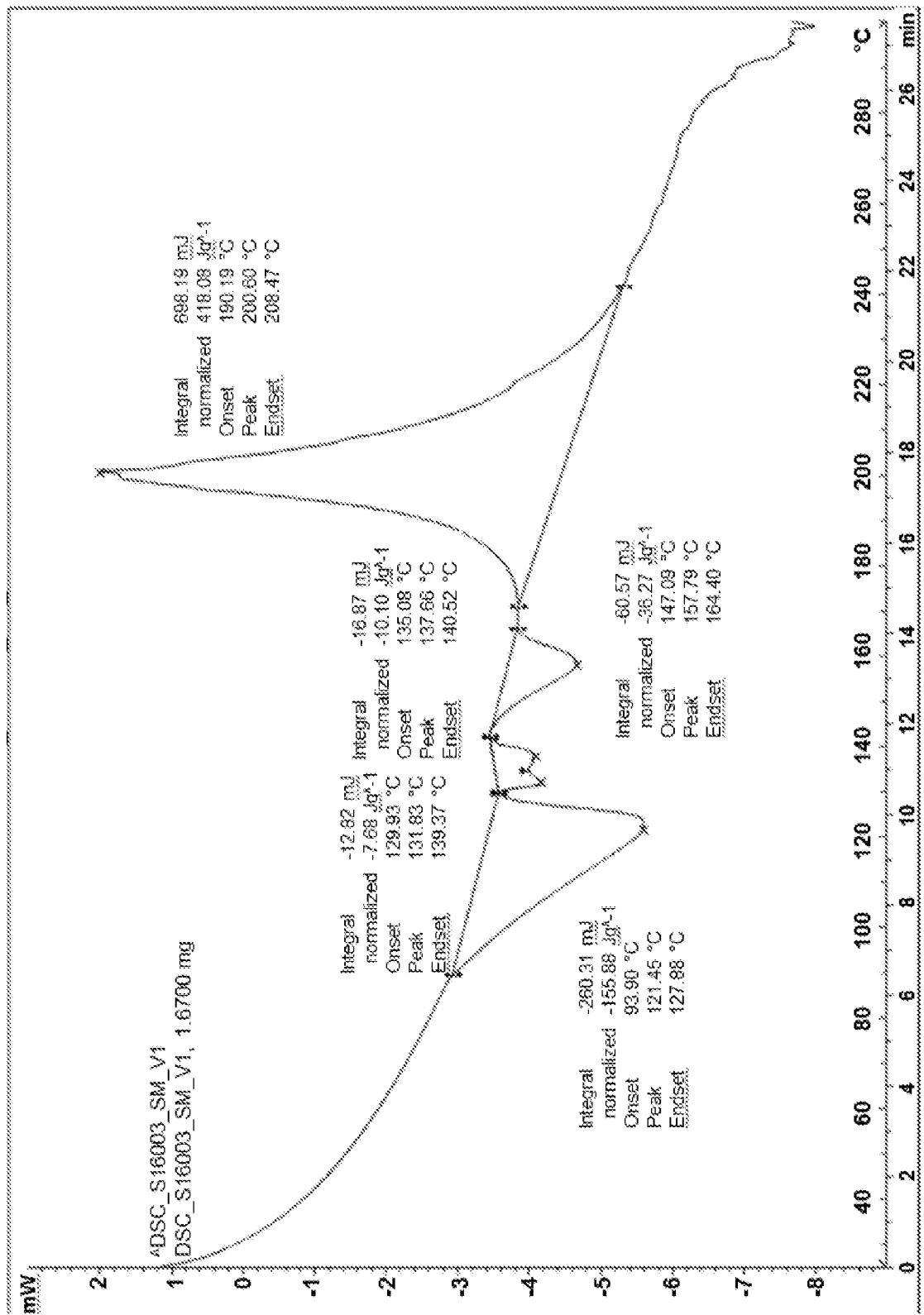
FIG. 2 depicts DSC analysis (with heating rate of 10° C./min) of 3-[2-butyl-1-(2-diethylamino-ethyl)-1H-benzoimidazol-5-yl]-N-hydroxy-acrylamide dihydrochloride 2.5 hydrate.
Figure 3A:
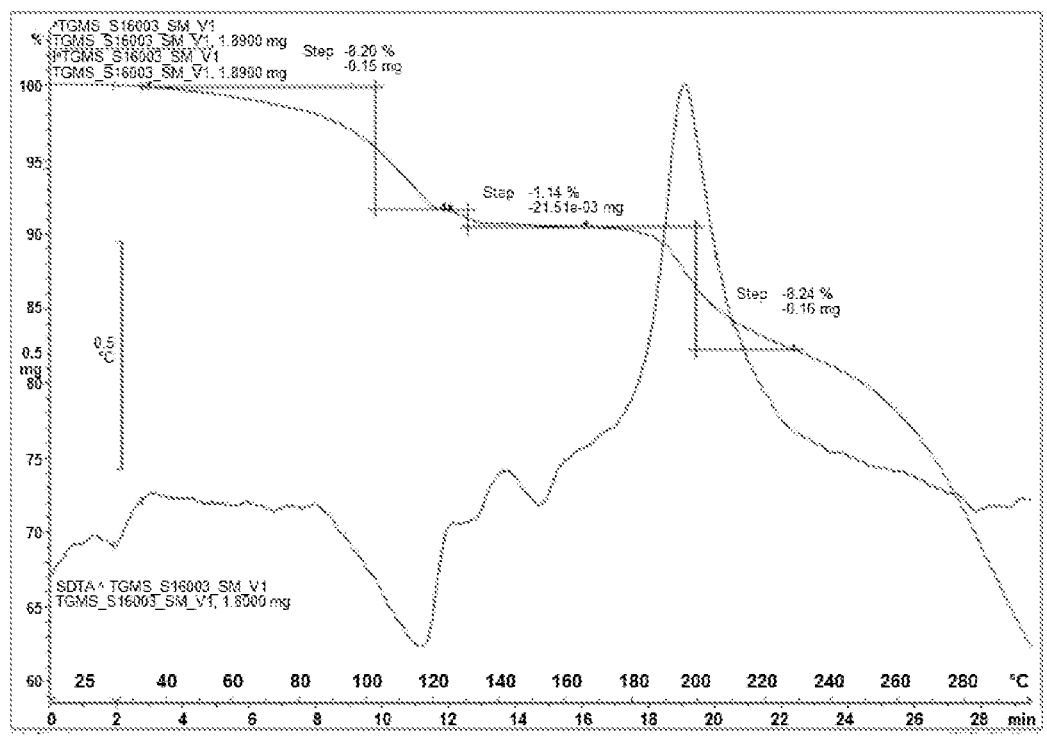
FIG. 3A depicts the TGA/SDTA analysis (with heating rate of 10° C./min) of 3-[2-butyl-1-(2-diethylamino-ethyl)-1H-benzoimidazol-5-yl]-N-hydroxy-acrylamide dihydrochloride 2.5 hydrate.
Figure 3B:
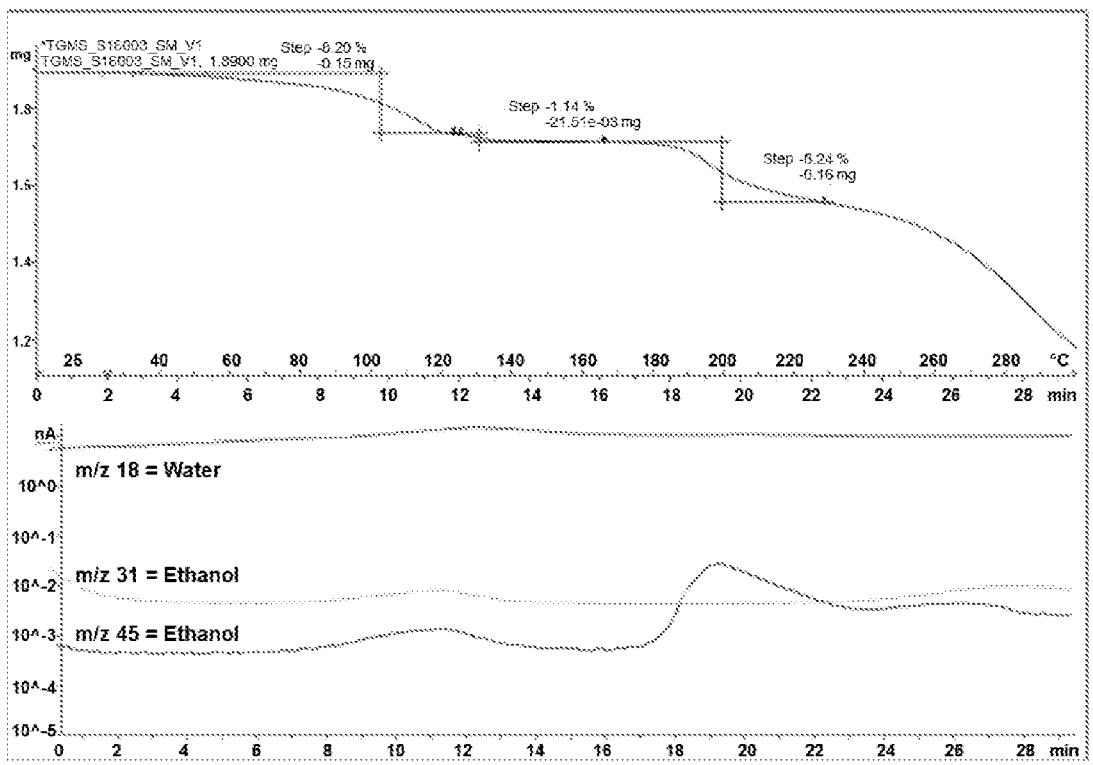
FIG. 3B depicts the TGMS analysis (with heating rate of 10° C./min) of 3-[2-butyl-1-(2-diethylamino-ethyl)-1H-benzoimidazol-5-yl]-N-hydroxy-acrylamide dihydrochloride 2.5 hydrate.

The term "polymorph Form 3" or "Form 3" or refers to a crystalline form of 3-[2-butyl-1-(2-diethylamino-ethyl)-1H-benzoimidazol-5-yl]-N-hydroxy-acrylamide dihydrochloride 2.5 hydrate that exhibits an X-ray powder diffraction pattern substantially the same as that shown in FIG. 1, and/or a DSC thermogram substantially the same as that shown in FIG. 2 and/or a TGA/SDTA trace substantially the same as that shown in FIG. 3A and/or a TGMS trace substantially the same as that shown in FIG. 3B. In some embodiments, a polymorph of 3-[2-butyl-1-(2-diethylamino-ethyl)-1H-benzoimidazol-5-yl]-N-hydroxy-acrylamide dihydrochloride 2.5 hydrate is characterized by the major peaks of FIG. 1. In some embodiments, the major peaks are the peaks of at least 20%, at least 15% or at least 10% of maximum intensity in the XRPD pattern of FIG. 1.

The present invention also relates to solid pharmaceutical compositions, comprising, as an active ingredient, an effective amount of 3-[2-butyl-1-(2-diethylamino-ethyl)-1H-benzoimidazol-5-yl]-N-hydroxy-acrylamide dihydrochloride 2.5 hydrate as the crystalline polymorph Form 3.

The present invention also relates to methods for treating or preventing diseases, comprising administering an effective amount of 3-[2-butyl-1-(2-diethylamino-ethyl)-1H-benzoimidazol-5-yl]-N-hydroxy-acrylamide dihydrochloride 2.5 hydrate, as the crystalline polymorph Form 3. In a still further aspect, the present invention provides the use of 3-[2-butyl-1-(2-diethylamino-ethyl)-1H-benzoimidazol-5-yl]-N-hydroxy-acrylamide dihydrochloride 2.5 hydrate as the crystalline polymorph Form 3, as hereinbefore defined, for use as a medicament for the treatment of cancer. In a further aspect, the present invention provides the use of 3-[2-butyl-1-(2-diethylamino-ethyl)-1H-benzoimidazol-5-yl]-N-hydroxy-acrylamide dihydrochloride 2.5 hydrate as the crystalline polymorph Form 3, as hereinbefore defined in the manufacture of a medicament for use in therapy. In a still further aspect, the present invention provides the use of 3-[2-butyl-1-(2-diethylamino-ethyl)-1H-benzoimidazol-5- yl]-N-hydroxy-acrylamide dihydrochloride 2.5 hydrate as the crystalline polymorph Form 3, as hereinbefore defined in the manufacture of a medicament for the treatment of human diseases or conditions in which modulation of histone deacetylase is beneficial. In a still further aspect, the present invention provides the use of 3-[2-butyl-1-(2-diethylamino-ethyl)-1H-benzoimidazol-5-yl]-N-hydroxy-acrylamide dihydrochloride 2.5 hydrate as the crystalline polymorph Form 3 as hereinbefore defined in the manufacture of a medicament for the treatment of cancer.

Also described herein are processes for the preparation of the crystalline polymorph Forms 1 and 3.

3-[2-butyl-1-(2-diethylamino-ethyl)-1H-benzoimidazol-5-yl]-N-hydroxy-acrylamide

Described herein are polymorph forms of 3-[2-butyl-1-(2-diethylamino-ethyl)-1H-benzoimidazol-5-yl]-N-hydroxy-acrylamide dihydrochloride which is known to modulate histone deacetylase (HDAC) activities. 3-[2-Butyl-1-(2-diethylamino-ethyl)-1H-benzoimidazol-5-yl]-N-hydroxy-acrylamide and related compounds are described in Patent Application Publications US 2009/0048300, WO2008108741, and US 2015/0258068.

3-[2-Butyl-1-(2-diethylamino-ethyl)-1H-benzoimidazol-5-yl]-N-hydroxy-acrylamide and the embodiments disclosed herein inhibit histone deacetylases. In certain embodiments, the histone deacetylase inhibitor interacts with and/or reduces the activity of more than one known histone deacetylase in the cell, which can be either from the same class of histone deacetylase or different class of histone deacetylase. In some other embodiments, the histone deacetylase inhibitor interacts and reduces the activity of predominantly one histone deacetylase, for example HDAC-1, HDAC-2, HDAC-3 or HDAC-8, which belongs to Class I HDAC enzymes. In some embodiments, the compounds disclosed herein have significant anti-proliferative effects and promote differentiation, cell cycle arrest in the G1 or G2 phase, and induce apoptosis.

Polymorph Form 1 (Monohydrate)

In one embodiment, 3-[2-butyl-1-(2-diethylamino-ethyl)-1H-benzoimidazol-5-yl]-N-hydroxy-acrylamide dihydrochloride monohydrate polymorph Form 1 exhibits an X-ray powder diffraction pattern characterized by the diffraction pattern summarized in Tables 1A and 1B. In some embodiments, the polymorph Form 1 of 3-[2-butyl-1-(2-diethylamino-ethyl)-1H-benzoimidazol-5-yl]-N-hydroxy-acrylamide dihydrochloride monohydrate comprises at least 3 peaks of (±0.1°2θ) of Table 1A or Table 1B. In certain embodiments, the polymorph Form 1 of 3-[2-butyl-1-(2-diethylamino-ethyl)-1H-benzoimidazol-5-yl]-N-hydroxy-acrylamide dihydrochloride monohydrate comprises at least 4 peaks of (±0.1°2θ) of Table 1A or Table 1B, at least 5 peaks of (±0.1°2θ) of Table 1A or Table 1B, at least 6 peaks of (±0.1°2θ) of Table 1A, at least 7 peaks of (±0.1°2θ) of Table 1A, at least 8 peaks of (±0.1°2θ) of Table 1A, or at least 9 peaks of (±0.1°2θ) of Table 1A.

TABLE 1A

Monohydrate Form 1

| Peak ID | Angle (2θ) | d-Spacing | Intensity |
|---|---|---|---|
| 1 | 7.94 | 11.13 | 37.97 |
| 2 | 9.74 | 9.07 | 9.81 |
| 3 | 13.76 | 6.43 | 12.28 |

TABLE 1A-continued

Monohydrate Form 1

| Peak ID | Angle (2θ) | d-Spacing | Intensity |
|---|---|---|---|
| 4 | 18.71 | 4.74 | 23.13 |
| 5 | 19.63 | 4.52 | 11.52 |
| 6 | 20.06 | 4.42 | 15.55 |
| 7 | 20.5 | 4.33 | 12.53 |
| 8 | 24.46 | 3.63 | 10.41 |
| 9 | 25.02 | 3.56 | 92.88 |

TABLE 1B

Monohydrate Form 1

| Peak ID | Angle (2θ) | d-Spacing | Intensity |
|---|---|---|---|
| 1 | 7.94 | 11.13 | 37.97 |
| 4 | 18.71 | 4.74 | 23.13 |
| 6 | 20.06 | 4.42 | 15.55 |
| 7 | 20.5 | 4.33 | 12.53 |
| 9 | 25.02 | 3.56 | 92.88 |

In one embodiment, the polymorph Form 1 is characterized by X-ray powder diffraction pattern peaks at 7.94, 18.71, and 25.02°2θ±0.1°2θ. In one embodiment, the polymorph Form 1 is characterized by X-ray powder diffraction pattern peaks at 7.94, 18.71, 20.06, and 25.02°2θ±0.1°2θ. In one embodiment, the polymorph Form 1 is further characterized by at least one peak at 13.76, 19.63, 20.5, or 24.46°2θ±0.1°2θ. In one embodiment, the polymorph Form 1 is further characterized by at least two peaks at 13.76, 19.63, 20.5, or 24.46°2θ±0.1°2θ. In one embodiment, the polymorph Form 1 is further characterized by at least three peaks at 13.76, 19.63, 20.5, or 24.46°2θ±0.1°2θ. In one embodiment, the polymorph Form 1 exhibits an X-ray powder diffraction pattern substantially the same as the X-ray powder diffraction pattern shown in FIG. 16.

In one embodiment, polymorph form 1 is produced by slurry conversion of the 2.5 hydrate in ethanol/water (98.4/1.6) at 50° C. In one embodiment, polymorph form 1 is hygroscopic and unstable.

In one embodiments, the monohydrate Form 1 is produced was upon slurry conversion of the 2.5 hydrate (Form 3) in ethanol/water 98.4/1.6. While stirring at 50° C. for 12 hours, precipitation occurred and the HT-XRPD analysis of the solid confirmed the formation of the monohydrate.

Polymorph Form 2 (Trihydrate)

In one embodiment, 3-[2-butyl-1-(2-diethylamino-ethyl)-1H-benzoimidazol-5-yl]-N-hydroxy-acrylamide dihydrochloride polymorph Form 2 exhibits an X-ray powder diffraction pattern characterized by the diffraction pattern summarized in Tables 2A and 2B. In some embodiments, the polymorph Form 2 of 3-[2-butyl-1-(2-diethylamino-ethyl)-1H-benzoimidazol-5-yl]-N-hydroxy-acrylamide dihydrochloride comprises at least 3 peaks of (±0.1°2θ) of Table 2A or 2B. In certain embodiments, the polymorph Form 2 of 3-[2-butyl-1-(2-diethylamino-ethyl)-1H-benzoimidazol-5-yl]-N-hydroxy-acrylamide dihydrochloride comprises at least 4 peaks of (±0.1°2θ) of Table 2A or Table 2B, at least 5 peaks of (±0.1°2θ) of Table 2A or Table 2B, at least 6 peaks of (±0.1°2θ) of Table 2A or Table 2B, at least 7 peaks of (±0.1°2θ) of Table 2A or Table 2B, at least 8 peaks of (±0.1°2θ) of Table 2A or Table 2B, at least 9 peaks of (±0.1°2θ) of Table 2A or Table 2B, at least 10 peaks of (±0.1°2θ) of Table 2A, at least 15 peaks of (±0.1°2θ) of Table 2A, at least 20 peaks of (±0.1°2θ) of Table 2A, at least 25 peaks of (±0.1°2θ) of Table 2A, or at least 30 peaks of (±0.1°2θ) of Table 2A.

TABLE 2A

Trihydrate Form 2

| Peak ID | Angle (2θ) | d-Spacing | Intensity |
|---|---|---|---|
| 1 | 4.46 | 19.79 | 38.33 |
| 2 | 4.54 | 19.45 | 36.21 |
| 3 | 6.46 | 13.67 | 12.08 |
| 4 | 6.58 | 13.42 | 11.84 |
| 5 | 7.42 | 11.9 | 14.6 |
| 6 | 7.58 | 11.64 | 23.13 |
| 7 | 7.69 | 11.48 | 14.67 |
| 8 | 8.82 | 10.01 | 14.6 |
| 9 | 8.89 | 9.93 | 11.51 |
| 10 | 11.12 | 7.94 | 56.01 |
| 11 | 11.58 | 7.63 | 15.12 |
| 12 | 11.87 | 7.45 | 34.1 |
| 13 | 13.3 | 6.65 | 11.46 |
| 14 | 19.41 | 4.57 | 11.98 |
| 15 | 20.39 | 4.35 | 11.17 |
| 16 | 20.86 | 4.25 | 41.96 |
| 17 | 22.03 | 4.03 | 29.4 |
| 18 | 22.3 | 3.98 | 22.36 |
| 19 | 22.66 | 3.92 | 15.77 |
| 20 | 22.82 | 3.89 | 13.38 |
| 21 | 22.94 | 3.87 | 17.97 |
| 22 | 23.06 | 3.85 | 15.55 |
| 23 | 24.83 | 3.58 | 58.24 |
| 24 | 24.91 | 3.57 | 64.44 |
| 25 | 25.22 | 3.53 | 39.83 |
| 26 | 25.35 | 3.51 | 38.44 |
| 27 | 25.42 | 3.5 | 39.99 |
| 28 | 25.55 | 3.48 | 42.64 |
| 29 | 25.66 | 3.47 | 44.16 |
| 30 | 25.98 | 3.43 | 19.55 |
| 31 | 40.58 | 2.22 | 12.8 |

TABLE 2B

Trihydrate Form 2

| Peak ID | Angle (2θ) | d-Spacing | Intensity |
|---|---|---|---|
| 1 | 4.46 | 19.79 | 38.33 |
| 2 | 4.54 | 19.45 | 36.21 |
| 10 | 11.12 | 7.94 | 56.01 |
| 12 | 11.87 | 7.45 | 34.1 |
| 16 | 20.86 | 4.25 | 41.96 |
| 23 | 24.83 | 3.58 | 58.24 |
| 24 | 24.91 | 3.57 | 64.44 |
| 25 | 25.22 | 3.53 | 39.83 |
| 26 | 25.35 | 3.51 | 38.44 |
| 27 | 25.42 | 3.5 | 39.99 |
| 28 | 25.55 | 3.48 | 42.64 |
| 29 | 25.66 | 3.47 | 44.16 |

In one embodiment, the polymorph Form 2 is characterized by X-ray powder diffraction pattern peaks at 11.12, 24.83, and 24.91°2θ±0.1°2θ. In one embodiment, the polymorph Form 2 is characterized by X-ray powder diffraction pattern peaks at 11.12, 20.86, 24.83, 24.91, and 25.66°2θ±0.1°2θ. In one embodiment, the polymorph Form 2 is further characterized by at least one peak at 4.46, 4.54, 11.87, 25.22, 25.35, or 25.42°2θ±0.1°2θ. In one embodiment, the polymorph Form 2 is further characterized by at least two peaks at 4.46, 4.54, 11.87, 25.22, 25.35, or 25.42°2θ±0.1°2θ. In one embodiment, the polymorph Form 2 is further characterized by at least three peaks at 4.46, 4.54, 11.87, 25.22, 25.35, or 25.42°2θ±0.1°2θ. In one embodiment, the polymorph Form 2 exhibits an X-ray powder diffraction pattern substantially the same as the X-ray powder diffraction pattern shown in FIG. 41.

Polymorph Form 3 (2.5 Hydrate)

In one embodiment, 3-[2-butyl-1-(2-diethylamino-ethyl)-1H-benzoimidazol-5-yl]-N-hydroxy-acrylamide dihydrochloride 2.5 hydrate polymorph Form 3 exhibits an X-ray powder diffraction pattern characterized by the diffraction pattern summarized in Tables 3A or 3B. In some embodiments, the polymorph Form 3 of 3-[2-butyl-1-(2-diethylamino-ethyl)-1H-benzoimidazol-5-yl]-N-hydroxy-acrylamide dihydrochloride 2.5 hydrate comprises at least 3 peaks of (±0.1°2θ) of Tables 3A or 3B.

In certain embodiments, the polymorph Form 3 of 3-[2-butyl-1-(2-diethylamino-ethyl)-1H-benzoimidazol-5-yl]-N-hydroxy-acrylamide dihydrochloride 2.5 hydrate comprises at least 4 peaks of (±0.1°2θ) of Table 3A or Table 3B, at least 5 peaks of (±0.1°2θ) of Table 3A, at least 6 peaks of (±0.1°2θ) of Table 3A, or at least 7 peaks of (±0.1°2θ) of Table 3A.

TABLE 3A 2.5 Hydrate Form 3

| Peak ID | Angle (2θ) | d-Spacing | Intensity |
|---|---|---|---|
| 1 | 6.46 | 13.66 | 95.9 |
| 2 | 9.78 | 9.04 | 9.8 |
| 3 | 16.57 | 5.35 | 13.65 |
| 4 | 19.58 | 4.53 | 12.11 |
| 5 | 20.26 | 4.38 | 26.77 |
| 6 | 22.27 | 3.99 | 23.28 |
| 7 | 26.68 | 3.34 | 37.99 |

TABLE 3B 2.5 Hydrate Form 3

| Peak ID | Angle (2θ) | d-Spacing | Intensity |
|---|---|---|---|
| 1 | 6.46 | 13.66 | 95.9 |
| 5 | 20.26 | 4.38 | 26.77 |
| 6 | 22.27 | 3.99 | 23.28 |
| 7 | 26.68 | 3.34 | 37.99 |

In one embodiment, the polymorph Form 3 is characterized by X-ray powder diffraction pattern peaks at 6.46, 20.26, and 26.68°2θ±0.1°2θ. In one embodiment, the polymorph Form 3 is characterized by X-ray powder diffraction pattern peaks at 6.46, 20.26, 22.27, and 26.68°2θ±0.1°2θ. In one embodiment, the polymorph Form 3 is further characterized by at least one peak at 9.78, 16.57, or 19.58°2θ±0.1°2θ. In one embodiment, the polymorph Form 3 is further characterized by at least two peaks at 9.78, 16.57, or 19.58°2θ±0.1°2θ. In one embodiment, the polymorph Form 3 is further characterized by at least three peaks at 9.78, 16.57, or 19.58°2θ±0.1°2θ. In one embodiment, the polymorph Form 3 exhibits an X-ray powder diffraction pattern substantially the same as the X-ray powder diffraction pattern shown in FIG. 1.

In one embodiment, polymorph Form 3 is a 2.5 hydrate. In one embodiment, polymorph Form 3 is non-hygroscopic. In one embodiment, polymorph Form 3 is physically stable under humid conditions (e.g., ranging from 10-95 RH). In one embodiments, Form 3 is has the desired physical properties including crystalline form, melting point, and moisture sorption to be compliant with Good Manufacturing Practices (GMP) for drug manufacturing.

In certain instances, the crystalline polymorph Form 3 was found to exhibit increased stability in comparison to the other solid state forms of 3-[2-butyl-1-(2-diethylamino-ethyl)-1H-benzoimidazol-5-yl]-N-hydroxy-acrylamide dihydrochloride. In some instances, improved stability of 3-[2-butyl-1-(2-diethylamino-ethyl)-1H-benzoimidazol-5-yl]-N-hydroxy-acrylamide dihydrochloride provides for the preparation of pharmaceutical dosage forms displaying reduced variability in the dosage present in a given dosage form, reduction in the presence of impurities in the final pharmaceutical product, and an improved shelf life of formulated dosage forms when compared to the pharmaceutical dosage form prepared with other solid state forms of 3-[2-butyl-1-(2-diethylamino-ethyl)-1H-benzoimidazol-5-yl]-N-hydroxy-acrylamide dihydrochloride. In some embodiments, Form 3 demonstrates no degradation for at least (e.g., less than 0.01%, less than 0.1%, less than 0.5% by wt.) for at least 2 days under accelerated conditions (e.g., 40° C./70% RH), for at least 1 week under accelerated conditions (e.g., 40° C./70% RH), for at least 1 month under accelerated conditions (e.g., 40° C./70% RH), for at least 6 months under accelerated conditions (e.g., 40° C./70% RH), and/or for at least 12 months under long-term conditions (e.g., 25° C./60 RH), for at least 18 months under long-term conditions (e.g., 25° C./60 RH), for at least 24 months under long-term conditions (e.g., 25° C./60 RH).

In certain instances, Form 3 exhibits decreased hygroscopity compared to other solid state forms. This property of decreased hygroscopicity greatly aids in the preparation of solid pharmaceutical dosage forms.

In one embodiment, polymorph Form 3 is produced from recrystallization of 3-[2-butyl-1-(2-diethylamino-ethyl)-1H-benzoimidazol-5-yl]-N-hydroxy-acrylamide dihydrochloride in ethanol and water mixtures containing more than 3% of water at ambient conditions. In one embodiment, Form 3 is produced from recrystallization of Form 1 in acetonitrile and water.

In certain embodiments, Form 3 optionally comprises a certain amount of Form 1 (e.g., less than 25% weight of the polymorph combination, less than 15% weight of the polymorph combination, less than 10% weight of the polymorph combination, less than 5% weight of the polymorph combination, less than 3% weight of the polymorph combination, less than 1% weight of the polymorph combination, or less than 0.5% weight of the polymorph combination). In other embodiments, Form 3 optionally comprises a certain amount of amorphous 3-[2-butyl-1-(2-diethylamino-ethyl)-1H-benzoimidazol-5-yl]-N-hydroxy-acrylamide dihydrochloride (e.g., less than 25% weight of the polymorph combination, less than 15% weight of the polymorph combination, less than 10% weight of the polymorph combination, less than 5% weight of the polymorph combination, less than 3% weight of the polymorph combination, less than 1% weight of the polymorph combination, or less than 0.5% weight of the polymorph combination).

Polymorph Form 4 (1.5 Hydrate)

In one embodiment, 3-[2-butyl-1-(2-diethylamino-ethyl)-1H-benzoimidazol-5-yl]-N-hydroxy-acrylamide dihydrochloride polymorph Form 4 exhibits an X-ray powder diffraction pattern characterized by the diffraction pattern summarized in Tables 4A and 4B. In some embodiments, the polymorph Form 4 of 3-[2-butyl-1-(2-diethylamino-ethyl)-1H-benzoimidazol-5-yl]-N-hydroxy-acrylamide dihydrochloride comprises at least 3 peaks of (±0.1°2θ) of Table 4A or 4B. In certain embodiments, the polymorph Form 4 of 3-[2-butyl-1-(2-diethylamino-ethyl)-1H-benzoimidazol-5-yl]-N-hydroxy-acrylamide dihydrochloride comprises at least 4 peaks of (±0.1°2θ) of Table 4A or Table 4B, at least 5 peaks of (±0.1°2θ) of Table 4A, at least 6 peaks of (±0.1°2θ) of Table 4A, at least 7 peaks of (±0.1°2θ) of Table 4A, at least 8 peaks of (±0.1°2θ) of Table 4A, at least 9 peaks of (±0.1°2θ) of Table 4A, or at least 10 peaks of (±0.1°2θ) of Table 4A.

TABLE 4A 1.5 hydrate Form 4

| Peak ID | Angle (2θ) | d-Spacing | Intensity |
|---|---|---|---|
| 1 | 5.34 | 16.53 | 17.87 |
| 2 | 6.97 | 12.66 | 49.18 |
| 3 | 10.66 | 8.29 | 80.01 |
| 4 | 11.46 | 7.71 | 10.13 |
| 5 | 12.07 | 7.32 | 10.92 |
| 6 | 12.14 | 7.28 | 11.38 |
| 7 | 22.3 | 3.98 | 13.87 |
| 8 | 22.38 | 3.97 | 13.9 |
| 9 | 22.46 | 3.95 | 15.21 |
| 10 | 24.76 | 3.59 | 35.47 |
| 11 | 25.84 | 3.44 | 33.27 |
| 12 | 26.62 | 3.34 | 13.79 |
| 13 | 27.46 | 3.24 | 14.58 |
| 14 | 27.57 | 3.23 | 13.63 |

TABLE 4B 1.5 hydrate Form 4

| Peak ID | Angle (2θ) | d-Spacing | Intensity |
|---|---|---|---|
| 2 | 6.97 | 12.66 | 49.18 |
| 3 | 10.66 | 8.29 | 80.01 |
| 10 | 24.76 | 3.59 | 35.47 |
| 11 | 25.84 | 3.44 | 33.27 |

In one embodiment, the polymorph Form 4 is characterized by X-ray powder diffraction pattern peaks at 6.97, 10.66, and 24.76°2θ±0.1°2θ. In one embodiment, the polymorph Form 4 is characterized by X-ray powder diffraction pattern peaks at 6.97, 10.66, 24.76 and 25.84°2θ±0.1°2θ. In one embodiment, the polymorph Form 4 is further characterized by at least one peak at 5.34, 12.14, 22.3, 22.38, 22.46, 26.62, 27.46, or 27.57°2θ±0.1°2θ. In one embodiment, the polymorph Form 4 is further characterized by at least two peaks at 5.34, 12.14, 22.3, 22.38, 22.46, 26.62, 27.46, or 27.57°2θ±0.1°2θ. In one embodiment, the polymorph Form 4 is further characterized by at least three peaks at 5.34, 12.14, 22.3, 22.38, 22.46, 26.62, 27.46, or 27.57°2θ±0.1°2θ. In one embodiment, the polymorph Form 4 exhibits an X-ray powder diffraction pattern substantially the same as the X-ray powder diffraction pattern shown in FIG. 44.

Polymorph Form 5 (Anhydrous Derived from Dehydration of Form 3 at 140° C.)

In one embodiment, 3-[2-butyl-1-(2-diethylamino-ethyl)-1H-benzoimidazol-5-yl]-N-hydroxy-acrylamide dihydrochloride polymorph Form 5 exhibits an X-ray powder diffraction pattern characterized by the diffraction pattern summarized in Tables 5A and 5B. In some embodiments, the polymorph Form 5 of 3-[2-butyl-1-(2-diethylamino-ethyl)-1H-benzoimidazol-5-yl]-N-hydroxy-acrylamide dihydrochloride comprises at least 3 peaks of (±0.1°2θ) of Tables 5A or 5B. In certain embodiments, the polymorph Form 5 of 3-[2-butyl-1-(2-diethylamino-ethyl)-1H-benzoimidazol-5-yl]-N-hydroxy-acrylamide dihydrochloride comprises at least 4 peaks of (±0.1°2θ) of Table 5A or Table 5B, at least 5 peaks of (±0.1°2θ) of Table 5A or Table 5B, at least 6 peaks of (±0.1°2θ) of Table 5A or Table 5B, at least 7 peaks of (±0.1°2θ) of Table 5A or Table 5B, at least 8 peaks of (±0.1°2θ) of Table 5A or Table 5B, at least 9 peaks of (±0.1°2θ) of Table 5A or Table 5B, at least 10 peaks of (±0.1°2θ) of Table 5A, at least 15 peaks of (±0.1°2θ) of Table 5A, at least 20 peaks of (±0.1°2θ) of Table 5A, at least 25 peaks of (±0.1°2θ) of Table 5A, or at least 30 peaks of (±0.1°2θ) of Table 5A.

TABLE 5A

Form 5 (anhydrous)

| Peak ID | Angle (2θ) | d-Spacing | Intensity |
|---|---|---|---|
| 1 | 6.87 | 12.85 | 60.19 |
| 2 | 6.94 | 12.72 | 59.95 |
| 3 | 7.26 | 12.17 | 33.91 |
| 4 | 9.7 | 9.11 | 19.5 |
| 5 | 11.34 | 7.79 | 55.56 |
| 6 | 13.41 | 6.59 | 17.8 |
| 7 | 13.57 | 6.52 | 11.62 |
| 8 | 17.26 | 5.13 | 10.84 |
| 9 | 17.71 | 5 | 13.67 |
| 10 | 17.78 | 4.98 | 14.44 |
| 11 | 17.86 | 4.96 | 16.05 |
| 12 | 18.99 | 4.67 | 12.5 |
| 13 | 19.1 | 4.64 | 16.26 |
| 14 | 19.94 | 4.45 | 49.33 |
| 15 | 20.3 | 4.37 | 23.03 |
| 16 | 20.58 | 4.31 | 27.91 |
| 17 | 20.66 | 4.29 | 29.78 |
| 18 | 20.9 | 4.25 | 20.01 |
| 19 | 21.17 | 4.19 | 10.3 |
| 20 | 21.78 | 4.08 | 10.33 |
| 21 | 21.87 | 4.06 | 10.36 |
| 22 | 21.94 | 4.05 | 12.12 |
| 23 | 22.11 | 4.02 | 13.85 |
| 24 | 23.91 | 3.72 | 11.49 |
| 25 | 24.1 | 3.69 | 10.02 |
| 26 | 24.91 | 3.57 | 13.43 |
| 27 | 25.06 | 3.55 | 11.53 |
| 28 | 25.59 | 3.48 | 68.74 |
| 29 | 26.5 | 3.36 | 13.65 |
| 30 | 26.62 | 3.34 | 11.83 |
| 31 | 26.95 | 3.3 | 27.08 |
| 32 | 27.05 | 3.29 | 23.95 |
| 33 | 27.74 | 3.21 | 18.51 |
| 34 | 27.82 | 3.2 | 18.08 |
| 35 | 27.94 | 3.19 | 18.35 |
| 36 | 28.06 | 3.18 | 18.07 |

TABLE 5B

Form 5 (anhydrous)

| Peak ID | Angle (2θ) | d-Spacing | Intensity |
|---|---|---|---|
| 1 | 6.87 | 12.85 | 60.19 |
| 2 | 6.94 | 12.72 | 59.95 |
| 3 | 7.26 | 12.17 | 33.91 |
| 5 | 11.34 | 7.79 | 55.56 |
| 14 | 19.94 | 4.45 | 49.33 |
| 15 | 20.3 | 4.37 | 23.03 |
| 16 | 20.58 | 4.31 | 27.91 |
| 17 | 20.66 | 4.29 | 29.78 |
| 18 | 20.9 | 4.25 | 20.01 |
| 28 | 25.59 | 3.48 | 68.74 |
| 31 | 26.95 | 3.3 | 27.08 |
| 32 | 27.05 | 3.29 | 23.95 |

Figure 5:
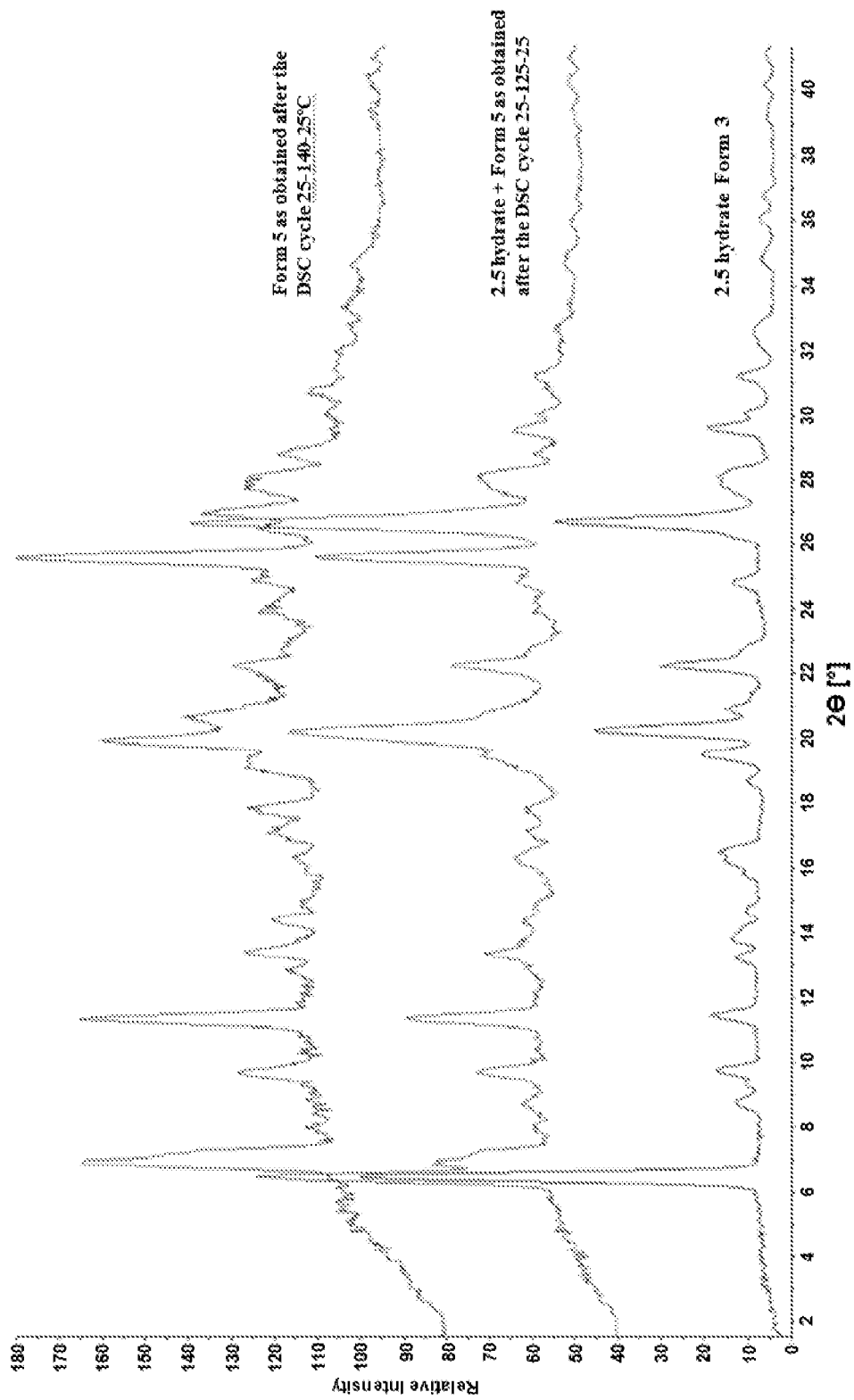
FIG. 5 depicts the overlay of XRPD patterns (from bottom to top): 3-[2-butyl-1-(2-diethylamino-ethyl)-1H-benzoimidazol-5-yl]-N-hydroxy-acrylamide dihydrochloride 2.5 hydrate, 2.5 hydrate +Form 5 as obtained after the DSC cycle 25-125-25° C. and Form 5 as obtained after the DSC cycle 25-140-25° C.

In one embodiment, the polymorph Form 5 is characterized by X-ray powder diffraction pattern peaks at 6.87, 6.94, 11.34, and 25.59°2θ±0.1°2θ. In one embodiment, the polymorph Form 5 is characterized by X-ray powder diffraction pattern peaks at 66.87, 6.94, 11.34, 19.94, and 25.59°2θ±0.1°2θ. In one embodiment, the polymorph Form 5 is further characterized by at least one peak at 7.26, 20.3, 20.58, 20.66, 20.9, 26.95, or 27.05°2θ±0.1°2θ. In one embodiment, the polymorph Form 5 is further characterized by at least two peaks at 7.26, 20.3, 20.58, 20.66, 20.9, 26.95, or 27.05°2θ±0.1°2θ. In one embodiment, the polymorph Form 5 is further characterized by at least three peaks at 7.26, 20.3, 20.58, 20.66, 20.9, 26.95, or 27.05°2θ±0.1°2θ. In one embodiment, the polymorph Form 5 exhibits an X-ray powder diffraction pattern substantially the same as the X-ray powder diffraction pattern shown in FIG. 5.

Polymorph Form 7 (Hemi-Ethanol Solvate)

In one embodiment, 3-[2-butyl-1-(2-diethylamino-ethyl)-1H-benzoimidazol-5-yl]-N-hydroxy-acrylamide dihydrochloride polymorph Form 7 exhibits an X-ray powder diffraction pattern characterized by the diffraction pattern summarized in Table 6A and Table 6B. In some embodiments, the polymorph Form 7 of 3-[2-butyl-1-(2-diethylamino-ethyl)-1H-benzoimidazol-5-yl]-N-hydroxy-acrylamide dihydrochloride comprises at least 3 peaks of (±0.1°2θ) of Tables 6A and 6B. In certain embodiments, the polymorph Form 7 of 3-[2-butyl-1-(2-diethylamino-ethyl)-1H-benzoimidazol-5-yl]-N-hydroxy-acrylamide dihydrochloride comprises at least 4 peaks of (±0.1°2θ) of Table 6A or Table 6B, at least 5 peaks of (±0.1°2θ) of Table 6A, at least 6 peaks of (±0.1°2θ) of Table 6A, at least 7 peaks of (±0.1°2θ) of Table 6A, at least 8 peaks of (±0.1°2θ) of Table 6A, at least 9 peaks of (±0.1°2θ) of Table 6A, at least 10 peaks of (±0.1°2θ) of Table 6A, or at least 11 peaks of (±0.1°2θ) of Table 6A.

TABLE 6A

Form 7 (Hemi-ethanol Solvate)

| Peak ID | Angle (2θ) | d-Spacing | Intensity |
|---|---|---|---|
| 1 | 4.90 | 18.01 | 94.74 |
| 2 | 8.34 | 10.59 | 15.69 |
| 3 | 8.82 | 10.01 | 8.57 |
| 4 | 9.90 | 8.92 | 23.02 |
| 5 | 12.58 | 7.03 | 9.38 |
| 6 | 14.10 | 6.27 | 10.39 |
| 7 | 24.54 | 3.62 | 8.33 |
| 8 | 24.7 | 3.6 | 9.16 |
| 9 | 25.53 | 3.48 | 44.72 |
| 10 | 26.51 | 3.36 | 27.41 |
| 11 | 26.58 | 3.35 | 28.01 |
| 12 | 27.14 | 3.28 | 14.05 |

TABLE 6B

Form 7 (Hemi-ethanol Solvate)

| Peak ID | Angle (2θ) | d-Spacing | Intensity |
|---|---|---|---|
| 1 | 4.90 | 18.01 | 94.74 |
| 9 | 25.53 | 3.48 | 44.72 |
| 10 | 26.51 | 3.36 | 27.41 |
| 11 | 26.58 | 3.35 | 28.01 |

In one embodiment, the polymorph Form 7 is characterized by X-ray powder diffraction pattern peaks at 4.90, 25.53, and 26.58°2θ±0.1°2θ. In one embodiment, the polymorph Form 7 is characterized by X-ray powder diffraction pattern peaks at 4.90, 25.53, 26.51, and 26.58°2θ±0.1°2θ. In one embodiment, the polymorph Form 7 is further characterized by at least one peak at 8.34, 9.90, 14.10, or 27.14°2θ±0.1°2θ. In one embodiment, the polymorph Form 7 is further characterized by at least two peaks at 8.34, 9.90, 14.10, or 27.14°2θ±0.1°2θ. In one embodiment, the polymorph Form 7 is further characterized by at least three peaks at 8.34, 9.90, 14.10, or 27.14°2θ±0.1°2θ. In one embodiment, 3-[2-butyl-1-(2-diethylamino-ethyl)-1H-benzoimidazol-5-yl]-N-hydroxy-acrylamide dihydrochloride polymorph Form 7 exhibits an X-ray powder diffraction pattern characterized by FIG. 47.

Polymorph Form 9 (Anhydrous)

In one embodiment, 3-[2-butyl-1-(2-diethylamino-ethyl)-1H-benzoimidazol-5-yl]-N-hydroxy-acrylamide dihydrochloride polymorph Form 9 exhibits an X-ray powder diffraction pattern characterized by the diffraction pattern summarized in Table 7A and Table 7B. In some embodiments, the polymorph Form 9 of 3-[2-butyl-1-(2-diethylamino-ethyl)-1H-benzoimidazol-5-yl]-N-hydroxy-acrylamide dihydrochloride comprises at least 3 peaks of (±0.1°2θ) of Tables 7A and 7B. In certain embodiments, the polymorph Form 9 of 3-[2-butyl-1-(2-diethylamino-ethyl)-1H-benzoimidazol-5-yl]-N-hydroxy-acrylamide dihydrochloride comprises at least 4 peaks of (±0.1°2θ) of Table 7A or Table 7B, at least 5 peaks of (±0.1°2θ) of Table 7A or Table 7B, at least 6 peaks of (±0.1°2θ) of Table 7A or Table 7B, at least 7 peaks of (±0.1°2θ) of Table 7A or Table 7B, at least 8 peaks of (±0.1°2θ) of Table 7A, at least 9 peaks of (±0.1°2θ) of Table 7A, at least 10 peaks of (±0.1°2θ) of Table 7A, at least 15 peaks of (±0.1°2θ) of Table 7A, or at least 20 peaks of (±0.1°2θ) of Table 7A.

TABLE 7A

Form 9 (anhydrous)

| Peak ID | Angle (2θ) | d-Spacing | Intensity |
|---|---|---|---|
| 1 | 3.55 | 24.88 | 33.37 |
| 2 | 8.88 | 9.95 | 34.98 |
| 3 | 10.08 | 8.76 | 22.58 |
| 4 | 11.38 | 7.77 | 14.61 |
| 5 | 14 | 6.32 | 25.06 |
| 6 | 14.18 | 6.24 | 65.17 |
| 7 | 14.64 | 6.04 | 21.64 |
| 8 | 18.7 | 4.74 | 16.76 |
| 9 | 19.3 | 4.59 | 29.73 |
| 10 | 20.01 | 4.43 | 21.1 |
| 11 | 20.18 | 4.4 | 10.08 |
| 12 | 21.32 | 4.16 | 35.65 |
| 13 | 21.77 | 4.08 | 11.49 |
| 14 | 22.1 | 4.02 | 16.52 |
| 15 | 22.36 | 3.97 | 17.08 |
| 16 | 23.23 | 3.82 | 42.31 |
| 17 | 24.54 | 3.62 | 22.45 |
| 18 | 24.83 | 3.58 | 25.52 |
| 19 | 25.65 | 3.47 | 55.41 |
| 20 | 25.71 | 3.46 | 60.69 |
| 21 | 25.93 | 3.43 | 19.2 |
| 22 | 26.58 | 3.35 | 90.47 |
| 23 | 26.86 | 3.31 | 12.87 |
| 24 | 27.62 | 3.23 | 18 |

TABLE 7B

Form 9 (anhydrous)

| Peak ID | Angle (2θ) | d-Spacing | Intensity |
|---|---|---|---|
| 1 | 3.55 | 24.88 | 33.37 |
| 2 | 8.88 | 9.95 | 34.98 |

TABLE 7B-continued

Form 9 (anhydrous)

| Peak ID | Angle (2θ) | d-Spacing | Intensity |
|---|---|---|---|
| 6 | 14.18 | 6.24 | 65.17 |
| 12 | 21.32 | 4.16 | 35.65 |
| 16 | 23.23 | 3.82 | 42.31 |
| 19 | 25.65 | 3.47 | 55.41 |
| 20 | 25.71 | 3.46 | 60.69 |
| 22 | 26.58 | 3.35 | 90.47 |

In one embodiment, the polymorph Form 9 is characterized by X-ray powder diffraction pattern peaks at 14.18, 25.71, and 26.58°2θ±0.1°2θ. In one embodiment, the polymorph Form 9 is characterized by X-ray powder diffraction pattern peaks at 14.18, 25.65, 25.71, and 26.58°2θ±0.1°2θ. In one embodiment, the polymorph Form 9 is further characterized by at least one peak at 3.55, 8.88, 21.32, or 23.23°2θ±0.1°2θ. In one embodiment, the polymorph Form 9 is further characterized by at least two peaks at 3.55, 8.88, 21.32, or 23.23°2θ±0.1°2θ. In one embodiment, the polymorph Form 9 is further characterized by at least three peaks at 3.55, 8.88, 21.32, or 23.23°2θ±0.1°2θ. In one embodiment, the polymorph Form 9 exhibits an X-ray powder diffraction pattern substantially the same as the X-ray powder diffraction pattern shown in FIG. 37 or 38.

Polymorph Form 10 (Hemihydrate)

In one embodiment, 3-[2-butyl-1-(2-diethylamino-ethyl)-1H-benzoimidazol-5-yl]-N-hydroxy-acrylamide dihydrochloride polymorph Form 10 exhibits an X-ray powder diffraction pattern characterized by the diffraction pattern summarized in Table 8A and Table 8B. In some embodiments, the polymorph Form 10 of 3-[2-butyl-1-(2-diethylamino-ethyl)-1H-benzoimidazol-5-yl]-N-hydroxy-acrylamide dihydrochloride comprises at least 3 peaks of (±0.1°2θ) of Table 8A or Table 8B. In certain embodiments, the polymorph Form 10 of 3-[2-butyl-1-(2-diethylamino-ethyl)-1H-benzoimidazol-5-yl]-N-hydroxy-acrylamide dihydrochloride comprises at least 4 peaks of (±0.1°2θ) of Table 8A or Table 8B, at least 5 peaks of (±0.1°2θ) of Table 8A or Table 8B, at least 6 peaks of (±0.1°2θ) of Table 8A or Table 8B, at least 7 peaks of (±0.1°2θ) of Table 8A or Table 8B, at least 8 peaks of (±0.1°2θ) of Table 8A or Table 8B, at least 9 peaks of (±0.1°2θ) of Table 8A or Table 8B, at least 10 peaks of (±0.1°2θ) of Table 8A or Table 8B, at least 15 peaks of (±0.1°2θ) of Table 8A, at least 20 peaks of (±0.1°2θ) of Table 8A, at least 25 peaks of (±0.1°2θ) of Table 8A, or at least 30 peaks of (±0.1°2θ) of Table 8A.

TABLE 8A 0.5 hydrate Form 10

| Peak ID | Angle (2θ) | d-Spacing | Intensity |
|---|---|---|---|
| 1 | 4.43 | 19.92 | 22.12 |
| 2 | 4.54 | 19.45 | 21.94 |
| 3 | 6.98 | 12.64 | 12.5 |
| 4 | 7.06 | 12.5 | 12.38 |
| 5 | 7.34 | 12.04 | 16.23 |
| 6 | 10.79 | 8.19 | 52.23 |
| 7 | 10.86 | 8.14 | 53.67 |
| 8 | 10.93 | 8.08 | 52.46 |
| 9 | 12.02 | 7.35 | 25.17 |
| 10 | 12.14 | 7.28 | 25.83 |

TABLE 8A-continued 0.5 hydrate Form 10

| Peak ID | Angle (2θ) | d-Spacing | Intensity |
|---|---|---|---|
| 11 | 12.26 | 7.21 | 23.85 |
| 12 | 15.38 | 5.75 | 11.85 |
| 13 | 15.46 | 5.72 | 12.25 |
| 14 | 20.83 | 4.26 | 19.63 |
| 15 | 20.9 | 4.25 | 21.53 |
| 16 | 21.31 | 4.17 | 10.42 |
| 17 | 21.66 | 4.1 | 14.87 |
| 18 | 21.98 | 4.04 | 16.41 |
| 19 | 22.07 | 4.02 | 19.31 |
| 20 | 22.18 | 4 | 18.61 |
| 21 | 22.74 | 3.91 | 17 |
| 22 | 22.9 | 3.88 | 19.11 |
| 23 | 23.18 | 3.83 | 17.89 |
| 24 | 23.4 | 3.8 | 24.91 |
| 25 | 24.78 | 3.59 | 72.74 |
| 26 | 24.85 | 3.58 | 71.88 |
| 27 | 25.35 | 3.51 | 31.75 |
| 28 | 25.49 | 3.49 | 30.54 |
| 29 | 25.58 | 3.48 | 28.45 |
| 30 | 29.18 | 3.06 | 13.35 |

TABLE 8B 0.5 hydrate Form 10

| Peak ID | Angle (2θ) | d-Spacing | Intensity |
|---|---|---|---|
| 6 | 10.79 | 8.19 | 52.23 |
| 7 | 10.86 | 8.14 | 53.67 |
| 8 | 10.93 | 8.08 | 52.46 |
| 9 | 12.02 | 7.35 | 25.17 |
| 10 | 12.14 | 7.28 | 25.83 |
| 25 | 24.78 | 3.59 | 72.74 |
| 26 | 24.85 | 3.58 | 71.88 |
| 27 | 25.35 | 3.51 | 31.75 |
| 28 | 25.49 | 3.49 | 30.54 |
| 29 | 25.58 | 3.48 | 28.45 |

In one embodiment, the polymorph Form 10 is characterized by X-ray powder diffraction pattern peaks at 10.86, 24.78, or 24.85°2θ±0.1°2θ. In one embodiment, the polymorph Form 10 is characterized by X-ray powder diffraction pattern peaks at 10.79, 10.86, 10.93, 24.78, or 24.85°2θ±0.1°2θ. In one embodiment, the polymorph Form 10 is further characterized by at least one peak at 12.02, 12.14, 25.35, 25.49, or 25.58°2θ±0.1°2θ. In one embodiment, the polymorph Form 10 is further characterized by at least two peaks at 12.02, 12.14, 25.35, 25.49, or 25.58°2θ±0.1°2θ. In one embodiment, the polymorph Form 10 is further characterized by at least three peaks at 12.02, 12.14, 25.35, 25.49, or 25.58°2θ±0.1°2θ. In one embodiment, the polymorph Form 10 exhibits an X-ray powder diffraction pattern substantially the same as the X-ray powder diffraction pattern shown in FIG. 49.

Summary of Analyses and Crystalline Patterns

Table 9 below summarizes the analyses and crystalline patterns identified. Solids were analyzed for their physical stability under accelerated aging conditions (40° C./70% RH) for 48 hours. After the exposure, the physical form was determined again by HT-XRPD analysis. The physicochemical characterization of the forms was done by TGMS analysis to determine the solvation state of the form and thermal events and by DSC analysis to confirm the thermal events observed in the SDTA signal of the TGA. (See Examples for details.)

TABLE 9

| Solid Form | Crystallization Conditions | Stability | Nature | Endotherms (° C.) |
|---|---|---|---|---|
| Form 3 | Starting material | Stable | 2.5 hydrate (9.3% water by TGMS) | 121.5, 131.8, 137.7, 157.8 |
| Form 1 | Slurry of 2.5 hydrate in EtOH/water (98.4/1.6, v/v) | Unstable | Monohydrate (3.1% water by TGMS) | 25-120 (broad), 228.8 |
| Form 4 | Slurry of 2.5 hydrate in EtOH for 2 hours | Unstable | 1.5 hydrate (6.1% water by TGMS) | 136.3, 156.8 |
| Form 2 | Slurry of monohydrate in MeOH/water (75/25, v/v) | Unstable | Trihydrate (10.5% water by TGMS) | 80.3, 116.9, 146 |
| Form 10 | Freeze-drying a water solution | Unstable | Hemihydrate (2.6% water by TGMS | 146.0 |
| Form 7 | Slurry of 2.5 hydrate in EtOH for 18 hours | — | Hemi ethanol solvate (5.1% ethanol by TGMS) | — |
| Form 5 | Dehydration of 2.5 hydrate | Unstable | Anhydrous | 156.3 |
| Form 9 | Slurry of 2.5 hydrate or monohydrate in EtOH absolute | Unstable | Anhydrous | 191.8 |

Methods

Provided herein are methods of treating a disease or disorder associated with dysregulation of histone deacetylase, comprising administering to a subject in need thereof an effective amount of a polymorph form as described herein of 3-[2-butyl-1-(2-diethylamino-ethyl)-1H-benzoimidazol-5-yl]-N-hydroxy-acrylamide dihydrochloride.

Some embodiments provided herein describe methods of treatment of a disorder caused by, associated with or accompanied by disruptions of cell proliferation and/or angiogenesis including administration of a therapeutically effective amount of a polymorph form as described herein of 3-[2-butyl-1-(2-diethylamino-ethyl)-1H-benzoimidazol-5-yl]-N-hydroxy-acrylamide dihydrochloride.

Also provided herein in some embodiments are agents for the treatment of a disorder caused by, associated with or accompanied by disruptions of cell proliferation and/or angiogenesis. In some embodiments, the agents are a polymorph form as described herein of 3-[2-butyl-1-(2-diethylamino-ethyl)-1H-benzoimidazol-5-yl]-N-hydroxy-acrylamide dihydrochloride.

Some embodiments described herein relate to the use of a polymorph form as described herein of 3-[2-butyl-1-(2-diethylamino-ethyl)-1H-benzoimidazol-5-yl]-N-hydroxy-acrylamide dihydrochloride in the preparation of a medicament for the treatment of a disorder caused by, associated with or accompanied by disruptions of cell proliferation and/or angiogenesis. In one embodiment, the disorder is a proliferative disorder. In a specific embodiment, the disorder is a cancer.

Other embodiments described herein provide a method of treatment of a disorder, disease or condition that can be treated by the inhibition of histone deacetylase including administration of a therapeutically effective amount of a polymorph form as described herein of 3-[2-butyl-1-(2-diethylamino-ethyl)-1H-benzoimidazol-5-yl]-N-hydroxy-acrylamide.

Also described herein are agents for the treatment of a disorder, disease or condition that can be treated by the inhibition of histone deacetylase. In one embodiment, the agent is an anticancer agent. In some embodiments, the agent is a polymorph form as described herein of 3-[2-butyl-1-(2-diethylamino-ethyl)-1H-benzoimidazol-5-yl]-N-hydroxy-acrylamide.

Some embodiments described herein provide a method for inhibiting cell proliferation including administration of an effective amount of a polymorph form as described herein of 3-[2-butyl-1-(2-diethylamino-ethyl)-1H-benzoimidazol-5-yl]-N-hydroxy-acrylamide.

Provided herein in certain embodiments is a method of treating chemoresistant cancer comprising administering to a subject in need thereof an effective amount of a DNA hypomethylating agent and a compound of formula (I). In some embodiments, the cancer is refractory, non-responsive or resistant to chemotherapy. In some embodiments, the cancer is refractory, non-responsive or resistant to haploidentical stem cell transplantation. In some embodiments, the cancer is resistant to azacitidine, decitabine, SGI-110, lenalidomide, TXA-127, or combinations thereof. In some embodiments, the cancer is resistant to azacitidine, decitabine, lenalidomide, TXA-127, or combinations thereof.

In one embodiment the disorder is selected from the group consisting of but not limited to cancer (e.g. breast cancer, colon cancer, prostate cancer, pancreatic cancer, leukemia, lymphomas, ovarian cancers, neuroblastomas, melanoma). In another embodiment the disorder is a proliferative disorder. In one embodiment the proliferative disorder is cancer. The cancer can include solid tumors or hematologic malignancies.

In some embodiments, the methods described herein are useful in treating various cancers including but not limited to bone cancers including Ewing's sarcoma, osteosarcoma, chondrosarcoma and the like, brain and CNS tumours including acoustic neuroma, neuroblastomas, glioma and other brain tumours, spinal cord tumours, breast cancers including ductal adenocarcinoma, metastatic ductal breast carcinoma, colorectal cancers, advanced colorectal adenocarcinomas, colon cancers, endocrine cancers including adenocortical carcinoma, pancreatic cancer, pituitary cancer, thyroid cancer, parathyroid cancer, thymus cancer, multiple endocrine neoplasma, gastrointestinal cancers including stomach cancer, esophageal cancer, small intestine cancer, liver cancer, extra hepatic bile duct cancer, gastrointestinal carcinoid tumour, gall bladder cancer, genitourinary cancers including testicular cancer, penile cancer, prostate cancer, gynaecological cancers including cervical cancer, ovarian cancer, vaginal cancer, uterus/endometrium cancer, vulva cancer, gestational trophoblastic cancer, fallopian tube cancer, uterine sarcoma, head and neck cancers including oral cavity cancer, lip cancer, salivary gland cancer, larynx cancer, hypopharynx cancer, orthopharynx cancer, nasal cancer, paranasal cancer, nasopharynx cancer, leukemias including childhood leukemia, acute lymphocytic leukemia, acute myeloid leukemia, chronic lymphocytic leukemia, chronic myeloid leukemia, hairy cell leukemia, acute promyelocytic leukemia, plasma cell leukemia, erythroleukemia, myelomas, haematological disorders including myelodysplastic syndromes, myeloproliferative disorders, aplastic anemia, Fanconi anemia, Waldenstroms Macroglobulinemia, lung cancers including small cell lung cancer, non-small cell lung cancer, mesothelioma, lymphomas including Hodgkin's disease, non-Hodgkin's lymphoma, cutaneous T-cell lymphoma, peripheral T-cell lymphoma, AIDS related Lymphoma, B-cell lymphoma, Burkitt's lymphoma, eye cancers including retinoblastoma, intraocular melanoma, skin cancers including melanoma, non-melanoma skin cancer, squamous cell carcinoma, merkel cell cancer, soft tissue sarcomas such as childhood soft tissue sarcoma, adult soft tissue sarcoma, Kaposi's sarcoma, urinary system cancers including kidney cancer, Wilms tumour, bladder cancer, urethral cancer, and transitional cell cancer.

In some embodiments, the disease or disorder associated with dysregulation of histone deacetylase is cancer. In some embodiments, the cancer is a hematological malignancy. In some embodiments, wherein the hematological malignancy is acute myeloid leukemia (AML), chronic myeloid leukemia (CML), chronic myelomonocytic leukemia, thrombolytic leukemia, a myelodysplastic syndrome (MDS), a myeloproliferative disorder, refractory anemia, a preleukemia syndrome, a lymphoid leukemia, lymphoma, non-Hodgkin's lymphoma, or an undifferentiated leukemia. In some specific embodiments, the cancer is myelodysplastic syndrome (MDS) or acute myeloid leukemia (AML). Non-limiting examples of non-Hodgkin's lymphoma include diffuse large B-cell lymphoma (DLBCL), mantle cell lymphoma (MCL), and chronic lymphocytic leukemia (CLL).

Other exemplary cancers that may be treated by the methods described herein include but are not limited to leukemias such as erythroleukemia, acute promyelocytic leukemia, acute myeloid leukemia, acute lymphocytic leukemia, acute T-cell leukemia and lymphoma such as B-cell lymphoma (e.g. Burkitt's lymphoma), cutaneous T-cell lymphoma (CTCL), and peripheral T-cell lymphoma.

Certain exemplary cancers that may be treated by the methods described herein include solid tumors and hematologic malignancies. In another embodiment, preferred cancers that may be treated with the compounds of the present invention are colon cancer, prostate cancer, hepatoma and ovarian cancer.

Pharmaceutical Compositions

The compound, compound forms and compositions described herein are administered either alone, or in combination with, pharmaceutically acceptable adjuvants, carriers, excipients, or diluents in a pharmaceutical composition, according to standard pharmaceutical practice. In certain embodiments, a polymorph form of 3-[2-butyl-1-(2-diethylamino-ethyl)-1H-benzoimidazol-5-yl]-N-hydroxy-acrylamide as described herein is administered as a pure chemical. In other embodiments, a polymorph form of 3-[2-butyl-1-(2-diethylamino-ethyl)-1H-benzoimidazol-5-yl]-N-hydroxy-acrylamide as described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Some embodiments provide pharmaceutical compositions comprising a polymorph form of 3-[2-butyl-1-(2-diethylamino-ethyl)-1H-benzoimidazol-5-yl]-N-hydroxy-acrylamide provided herein, or a pharmaceutically acceptable salt thereof, and a pharmaceutically acceptable excipient. Some embodiments provide pharmaceutical compositions comprising 3-[2-butyl-1-(2-diethylamino-ethyl)-1H-benzoimidazol-5-yl]-N-hydroxy-acrylamide dihydrochloride 2.5 hydrate for Form 3, as described herein.

In some embodiments, the polymorph form of 3-[2-butyl-1-(2-diethylamino-ethyl)-1H-benzoimidazol-5-yl]-N-hydroxy-acrylamide as described herein is substantially pure. In some embodiments, the polymorph form of 3-[2-butyl-1-(2-diethylamino-ethyl)-1H-benzoimidazol-5-yl]-N-hydroxy-acrylamide contains less than about 5%, less than about 1%, or less than about 0.1%, of other organic small molecules, such as unreacted intermediates or synthesis by-products that are created in, or left behind by, for example, one or more of the steps of a synthesis method.

In further or additional embodiments, a polymorph form of 3-[2-butyl-1-(2-diethylamino-ethyl)-1H-benzoimidazol-5-yl]-N-hydroxy-acrylamide as described herein is polymorphically pure, wherein the form is substantially free of other polymorph forms of 3-[2-butyl-1-(2-diethylamino-ethyl)-1H-benzoimidazol-5-yl]-N-hydroxy-acrylamide. In some embodiments, "polymorphically pure" refers to a polymorph form containing less than about 10%, less than about 5%, less than about 2%, less than about 0.5%, less than about 0.2%, less than about 0.1%, or less than about 0.05% of other polymorphic forms. In some embodiments, "polymorphically pure" refers to a polymorph form containing between 0.2% and 10%, between 0.2% and 5%, or between 0.2% and 2%, between 0.2 and 1%, between 0.1% and 10%, between 0.1% and 5%, between 0.1% and 2%, or between 0.1% and 1% by weight of other polymorph forms.

In some embodiments, a pharmaceutical composition comprises polymorph Form 3 of 3-[2-butyl-1-(2-diethylamino-ethyl)-1H-benzoimidazol-5-yl]-N-hydroxy-acrylamide dihydrochloride 2.5 hydrate, wherein Form 3 is polymorphically pure. In some embodiments, the polymorphically pure Form 3 contains less than 2% by weight of Form 1 as determined by powder X-ray diffraction. In some embodiments, the polymorphically pure Form 3 contains less than 10%, less than 5%, less than 2%, less than 1%, less than 0.5%, less than 0.2% or less than 0.1% by weight of Form 1, as determined by powder X-ray diffraction.

In some embodiments, the pharmaceutical compositions described herein are formulated as oral dosage forms. Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

Pharmaceutical compositions described herein may be administered to patients (e.g. humans), for the treatment of one or more diseases, as described herein. The dose of the composition comprising at least one polymorph form of 3-[2-butyl-1-(2-diethylamino-ethyl)-1H-benzoimidazol-5-yl]-N-hydroxy-acrylamide as described herein differ, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses for treatment of a disease described herein may range from about 1.0 mg to about 1000 mg, one to four times, or more, per day. In some embodiments, the oral dose is based on the surface area of the patient and is in a range of 0.1 to 1000 mg/m$^2$. In some embodiments, the oral dose is in a range of 1 to 250, 1 to 150, or 1 to 100 mg/m$^2$ per day. In some embodiments, the oral dose is in the range of 0.1 to 1000 mg per day, administered in a single dose or in two to four divided doses. In some embodiments, the oral dose is 1 to 200 mg per day, 1 to 100 mg per day, 10 to 100 mg per day, 10 to 90 mg per day, 10 to 80 mg per day, 20 to 100 mg per day, 20 to 90 mg per day or 20 to 80 mg per day. In some embodiments, the oral dose comprises 3-[2-butyl-1-(2-diethylamino-ethyl)-1H-benzoimidazol-5-yl]-N-hydroxy-acrylamide dihydrochloride 2.5 hydrate (Form 3), as described herein, and optionally one or more excipients, such as one or more carriers, one or more diluents, one or more lubricants, one or more dispersants or one or more glidants.

Combination Therapy

Any suitable hypomethylating agent may be used in combination with a polymorph form as described herein of 3-[2-butyl-1-(2-diethylamino-ethyl)-1H-benzoimidazol-5-yl]-N-hydroxy-acrylamide. DNA hypomethylating agents for use in the methods provided herein include but are not limited to 5-azacytidine (azacitidine), 5-azadeoxycytidine (decitabine), SGI-110, zebularine and procaine. In certain specific embodiments, the DNA hypomethylating agent is 5-azacytidine (azacitidine).

Modes of Administration

The compound, compound forms and compositions described herein are administered either alone, or in combination with, pharmaceutically acceptable adjuvants, carriers, excipients, or diluents in a pharmaceutical composition, according to standard pharmaceutical practice.

The pharmaceutical compositions described herein are, for example, in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition is, in some embodiments, in unit dosage forms suitable for single administration of precise dosages. Pharmaceutical compositions include a compound or compound form as described herein as an active ingredient, and a conventional pharmaceutical carrier or excipient. In some embodiments, these compositions include other or additional medicinal or pharmaceutical agents, carriers, adjuvants, etc.

Pharmaceutical compositions are conveniently presented in unit dosage form. In some embodiments, they are prepared with a specific amount of active compound by any of the methods well known or apparent to those skilled in the pharmaceutical arts.

EXAMPLES

The following examples further illustrate the invention but should not be construed as in any way limiting its scope. In particular, the processing conditions are merely exemplary and can be readily varied by one of ordinary skill in the art.

All methods described herein can be performed in a suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. Unless defined otherwise, technical and scientific terms used herein have the same meaning as is commonly understood by one of skill in the art to which this invention belongs.

Example 1: Preparation of 3-[2-butyl-1-(2-diethyl-amino-ethyl)-1H-benzoimidazol-5-yl]-N-hydroxy-acrylamide Dihydrochloride Monohydrate Form 1

Several trials were attempted to produce the monohydrated of 3-[2-butyl-1-(2-diethylamino-ethyl)-1H-benzoimidazol-5-yl]-N-hydroxy-acrylamide dihydrochloride to be used in the polymorph screen. The attempts are presented Table 10. Approximately 1 g of starting material 2.5 hydrate Form 3 was suspended in 15 ml ethanol absolute at room temperature. After 10 minutes, the suspension formed a 'solid'. Subsequently, 5 ml of ethanol absolute was added to make a suspension again. The experiment was stirred at ambient conditions for 12 hours. The solids were isolated from the mother liquor by centrifugation and dried under deep vacuum. A new solid form designated Form 9 (anhydrous) was obtained.

Other attempts to produce the monohydrate consisted of varying the slurry time in ethanol absolute. Two experiments were performed upon slurry for two hours and 12 hours. The first experiment led to the identification of the 1.5 hydrate (Form 4). The slurry after 12 hours led to the identification of a new solid form designated Form 7 an ethanol hemisolvate.

One last attempt consisted in preparing amorphous material by freeze-drying and then slurring the amorphous powder in an ethanol/water mixture. However, the freeze-drying experiment led to the formation of what it seems to be a hemihydrate (Form 10).

The protocol that led to the manufacturing of the monohydrate Form 1 was upon slurry conversion of the 2.5 hydrate (Form 3) in ethanol/water 98.4/1.6. Two grams of the 2.5 hydrate Form 3 were suspended in 40 ml ethanol/water (98.4/1.6) at 50° C. After 10 minutes the suspension was completely dissolved. The experiment was stirred at 50° C. for 12 hours. During this time precipitation occurred and the HT-XRPD analysis of the solid confirmed the formation of the monohydrate. Approximately 1.2 g were recovered from the initial 2 grams (yield 60%).

TABLE 10

| Solvent | Crystallization Method | Mass (mg) | Volume solvent (mL) | Dissolved at initial temperature | Form |
| --- | --- | --- | --- | --- | --- |
| Ethanol | Slurry | 1001 | 15 + 5 | No | Anhydrous Form 9 |
| Ethanol | Slurry (2 hours) | 50 | 1.0 | Yes | 1.5 hydrate Form 4 |
| Ethanol | Slurry (18 hours) | 51 | 1.0 | Yes | 0.5 ethanol solvate Form 7 |
| Water | Freeze drying | 28 | 0.165 | Yes | Hemi hydrate Form 10 |
| Water | Freeze drying | 26 | 0.155 | Yes | Hemi hydrate Form 10 |
| Ethanol | Slurry (50° C.) | 51 | 1.0 | No | Anhydrous Form 9 |
| Ethanol/Water (98.4/1.6) | Slurry (50° C.) | 53 | 1.0 | No | Monohydrate Form 1 |
| Ethanol/Water (98.4/1.6) | Slurry (50° C.) | 2000 | 40 | No | Monohydrate Form 1 |
| Ethanol/Water (98.4/1.6) | Slurry (50° C.) | 1023 | 15 | No | Monohydrate Form 1 |
| Ethanol/Water (98.4/1.6) | Slurry (50° C.) | 1003 | 15 | No | Monohydrate Form 1 |

Example 2: Preparation of 3-[2-butyl-1-(2-diethyl-amino-ethyl)-1H-benzoimidazol-5-yl]-N-hydroxy-acrylamide Dihydrochloride 2.5 Hydrate Form 3

5 g of 3-[2-butyl-1-(2-diethylamino-ethyl)-1H-benzoimidazol-5-yl]-N-hydroxy-acrylamide monohydrate Form 1 (lot DBDERP8001) was suspended in Acetonitrile (80 ml) and heated to a gentle reflux. Water (~20 mL) was added until the mixture became homogenous. The solution was slowly cooled to ambient temperature and keep at this temperature for approximately 18 h. The crystals that formed were filtered off and collected without drying. The crystals were determined to have the same retention time by HPLC and the XRPD matched XRPD pattern of Form 3.

Example 3: Analysis of 2.5 Hydrate Polymorph Form 3

X-Ray Powder Diffraction of Form 3

The HR-XRPD analysis showed that 3-[2-butyl-1-(2-diethylamino-ethyl)-1H-benzoimidazol-5-yl]-N-hydroxy-acrylamide dihydrochloride 2.5 hydrate consisted of one single crystalline phase. The HR-XRPD diffractogram is presented in FIG. 1.

Indexing of the HR-XRPD patterns resulted in the cell parameters of 3-[2-butyl-1-(2-diethylamino-ethyl)-1H-benzoimidazol-5-yl]-N-hydroxy-acrylamide dihydrochloride 2.5 hydrate. This form crystallizes in a monoclinic system with a C2/c space group. The calculated cell parameters are presented in Table 11. The water content of 2.5 molecules of water per molecule of API was according to the calculated density of the crystal.

TABLE 11

| Identification code | 2.5 hydrate |
|---|---|
| Empirical formula | $C_{20}H_{32}N_4O_2^{+\bullet}2Cl^{-\bullet}2.5 H_2O$ |
| Fw | 476.44 |
| Empirical formula | — |
| Fw | — |
| T [K] | 296 (2) |
| λ [Å] | 1.5418 |
| Crystal system | Monoclinic |
| Space group | C2/c |
| Unit cell dimensions | |
| a [Å] | 20.158 (4) |
| b [Å] | 18.980 (4) |
| c [Å] | 13.559 (2) |
| β [°] | 99.441 (9) |
| V [Å$^3$] | 5117.4 (9) |
| Z (Z') | 8 (1) |
| $D_c$ [g/cm$^3$] | 1.237 |
| $D_e$ [g/cm$^3$] | — |
| Capillary size [mm$^2$] | 0.3 × 8 |
| 2θ Step size [°] | 0.016 |
| No of steps | 2377 |
| Time per step [s] | 4 |
| 2θ range [°] | 4 → 41.5 |
| Rexp | 5.45 |
| $R_{wp}$ | 6.05 |
| $R_p$ | 4.59 |
| GOF | 1.11 |
| $R_{Brag}$ | 0.27 |
| Amorphous Content [%] | Not determined |

Thermal Analysis of Form B

The DSC thermogram showed several endotherms, which are most likely attributed to the water content. The four endotherms were observed at 121.5° C., 131.8° C., 137.7° C. and 157.8° C. (see FIG. 2). The first three endotherms observed in the DSC trace corresponded to the loss of water.

The TGMS analysis showed a mass loss of 9.3% in two consecutive steps (see FIG. 3B). A mass loss of 9.3% of water corresponds to 2.5 molecules of water. Based on the evaluation of the MS signal, the two mass losses are attributed to water and ethanol. The third mass loss is likely attributed to the disproportionation of the hydrochloride salt.

Figure 4A:
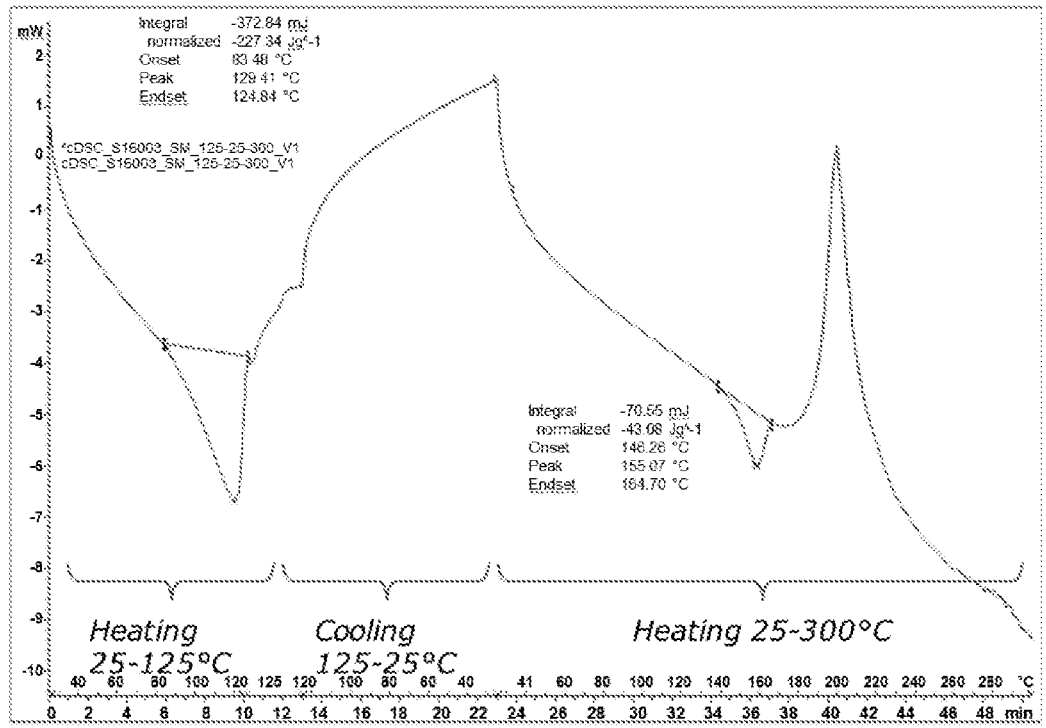
FIG. 4A depicts DSC cycles of 3-[2-butyl-1-(2-diethylamino-ethyl)-1H-benzoimidazol-5-yl]-N-hydroxy-acrylamide dihydrochloride 2.5 hydrate (with heating rate of 10° C./min) with a temperature cycle of 25-125-25-300° C.
Figure 4B:
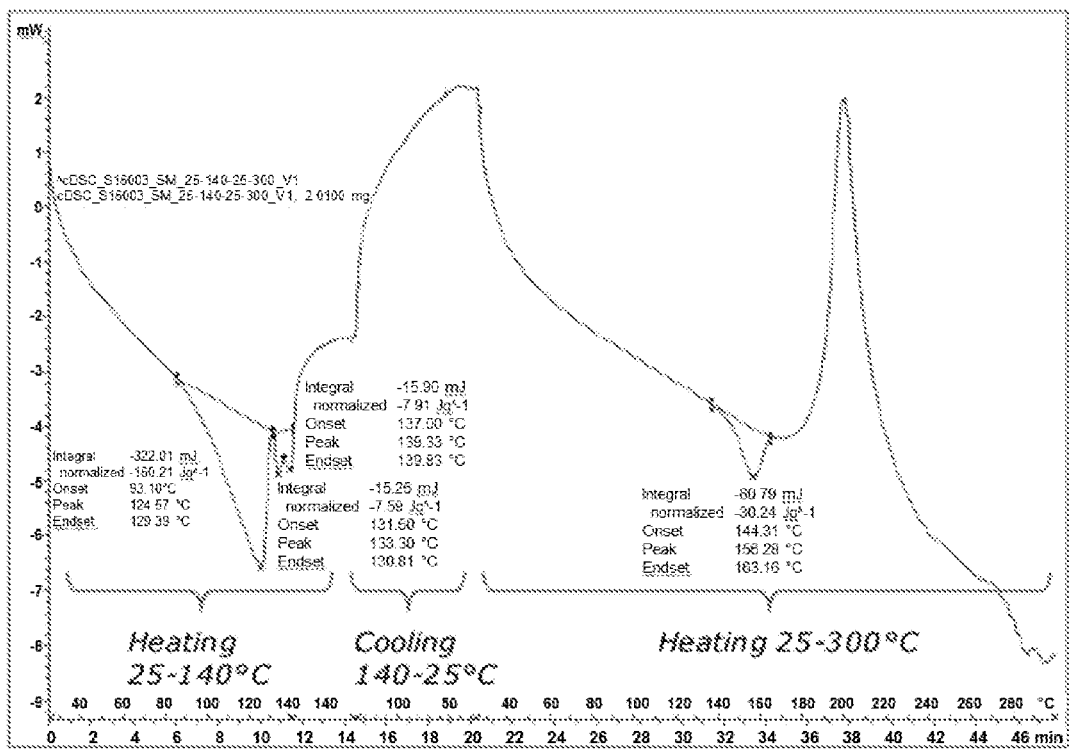
FIG. 4B depicts DSC cycles of 3-[2-butyl-1-(2-diethylamino-ethyl)-1H-benzoimidazol-5-yl]-N-hydroxy-acrylamide dihydrochloride 2.5 hydrate (with heating rate of 10° C./min) with a temperature cycle of 25-140-25-300° C.

To confirm the nature of the thermal events, four cycling DSC experiments were performed. Two samples of 3-[2-butyl-1-(2-diethylamino-ethyl)-1H-benzoimidazol-5-yl]-N-hydroxy-acrylamide dihydrochloride 2.5 hydrate were heated up to 125° C. and 140° C. and then cooled to 25° C. The obtained solids were analyzed by HT-XRPD. Two other samples were treated identically with the exception that the samples were heated up again to 300° C. after cooling (see FIG. 4A and FIG. 4B).

After the initial heating cycles, the XRPD analysis of the solids indicated that conversion to a new solid form had occurred. This new solid form was designated Form 5. Based on the thermal behavior in the second DSC cycle this form is an anhydrous form with a melting temperature of 156° C. Upon dehydration of the 2.5 hydrate conversion to the anhydrous Form 5 occurred. An overlay of the XRPD patterns of polymorph Form 3 and form 5 is provided (see FIG. 5).

Karl Fischer analysis confirmed the hydrated nature of the starting material with a water content of 8.7%, which corresponds to 2.3 molecules of water per molecule of API. The slight difference in the water content between the TGMS and KF analyses (9.3% vs 8.7%, respectively) is attributed to some residual ethanol present in the starting material.

Variable Temperature XRPD Analysis of Form 3

Figure 6:
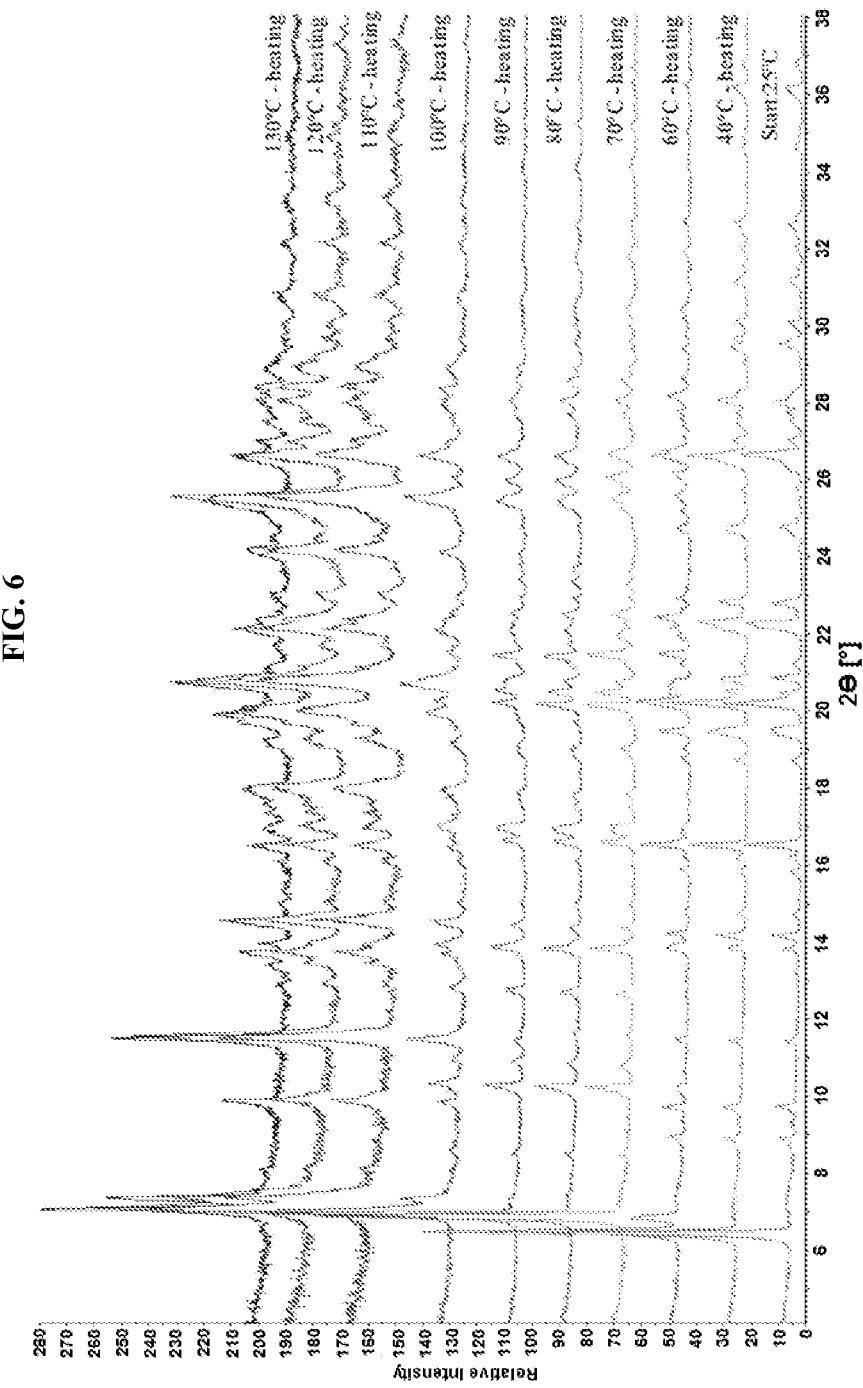
FIG. 6 depicts the overlay of XRPD patterns obtained from the variable temperature XRPD measurements of 3-[2-butyl-1-(2-diethylamino-ethyl)-1H-benzoimidazol-5-yl]-N-hydroxy-acrylamide dihydrochloride 2.5 hydrate between 25-130° C. (sequence from bottom to top).
Figure 7:
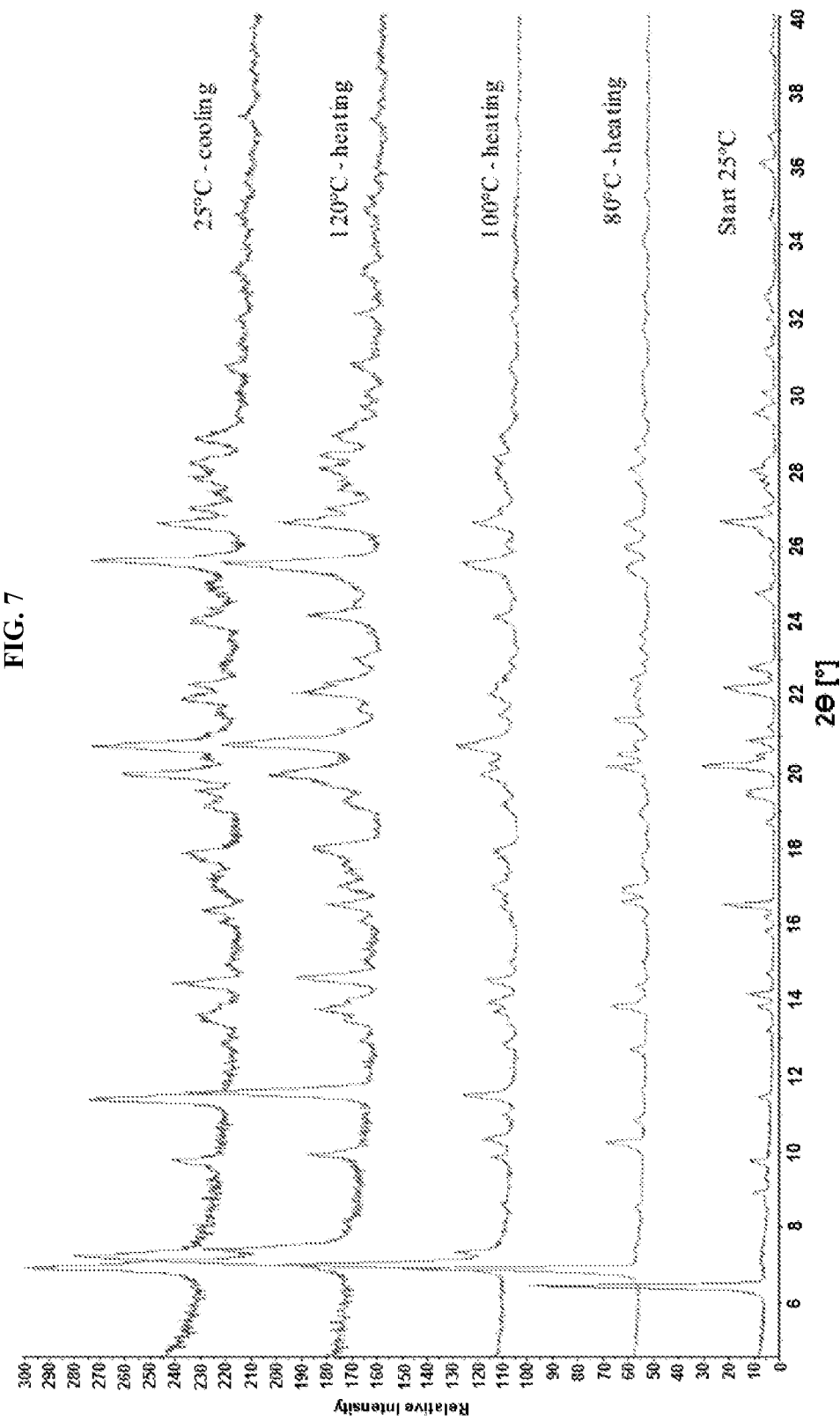
FIG. 7 depicts the overlay of XRPD patterns corresponding to the new solid forms of 3-[2-butyl-1-(2-diethylamino-ethyl)-1H-benzoimidazol-5-yl]-N-hydroxy-acrylamide identified in the variable temperature XRPD measurements.

To investigate the phase interconversions upon temperature exposure, a variable temperature XRPD analysis on 3-[2-butyl-1-(2-diethylamino-ethyl)-1H-benzoimidazol-5-yl]-N-hydroxy-acrylamide dihydrochloride 2.5 hydrate was performed. The experiment was run between 25° C. to 130° C. with cooling back to 25° C. at the end. At 60° C., additional peaks corresponding to a new solid form started to appear. At 70° C., the conversion to this novel form was completed. At 100° C., a second conversion was observed which was completed at 110° C. The latter solid form seems to be the anhydrous Form 5. After reaching a temperature of 130° C., the material was cooled back to 25° C. Upon cooling no solid form conversion were recorded indicating that the dehydration/hydration process was not reversible. The data is presented in FIG. 6. Conversion to a new solid form was initially observed at 60° C. and full conversion was observed at 70° C. At 100° C. a new transition was identified which correspond to Form 5 previously identified in the cycling DSC analyses. An overlay of XRPD patterns corresponding to new sold forms of 3-[2-butyl-1-(2-diethylamino-ethyl)-1H-benzoimidazol-5-yl]-N-hydroxy-acrylamide dihydrochloride identified in the variable temperature XRPD measurements is presented in FIG. 7.

HPLC Analysis

Figure 8A:
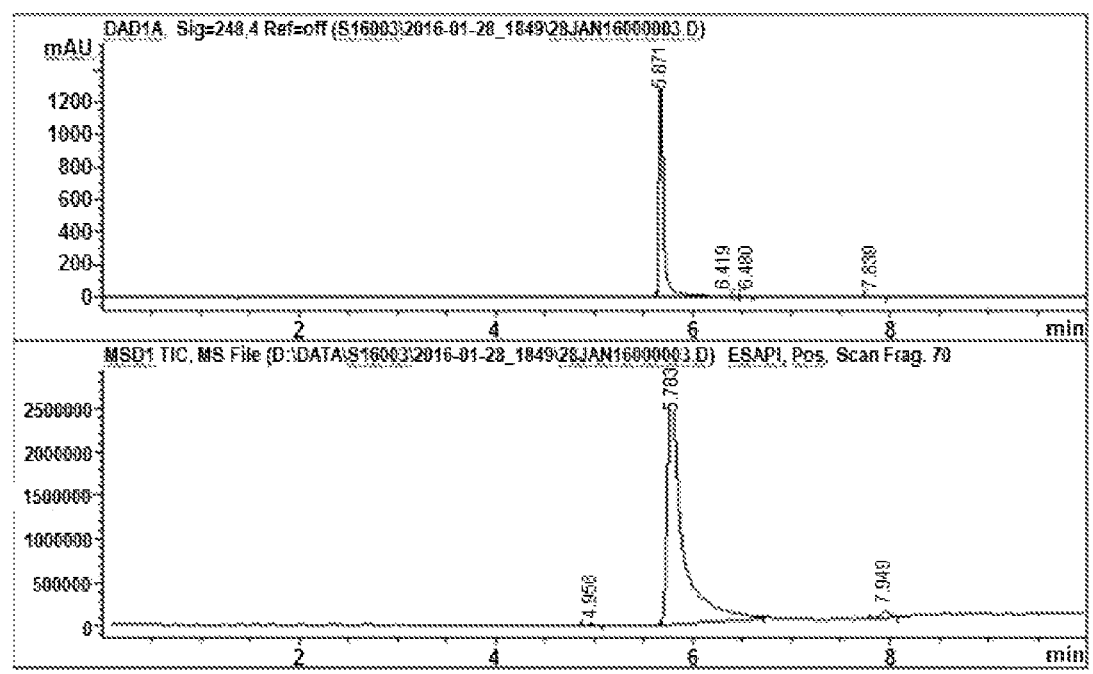
FIG. 8A depicts the HPLC data of the 2.5 hydrate 3-[2-butyl-1-(2-diethylamino-ethyl)-1H-benzoimidazol-5-yl]-N-hydroxy-acrylamide dihydrochloride (polymorph Form 3).

The HPLC trace of polymorph Form 3 is shown in FIG. 8A. The main peak was observed at a retention time of 5.7 min with a chemical purity of 99.5% (area %). The peak listing for the trace is given in the table below.

| Peak # | Ret time (min) | Type | Width (min) | Area (mAU*s) | Height (mAU) | Area (%) |
|---|---|---|---|---|---|---|
| 1 | 5.671 | BV | 0.0474 | 4642.60937 | 1489.93054 | 99.4514 |
| 2 | 6.419 | VV | 0.0368 | 10.52158 | 3.63135 | 0.2254 |

-continued

| Peak # | Ret time (min) | Type | Width (min) | Area (mAU*s) | Height (mAU) | Area (%) |
|---|---|---|---|---|---|---|
| 3 | 6.486 | VB | 0.0583 | 8.90586 | 1.88013 | 0.1908 |
| 4 | 7.839 | BB | 0.0657 | 6.18187 | 1.36780 | 0.1324 |

Mass Spectrometry Analysis

Figure 8B:
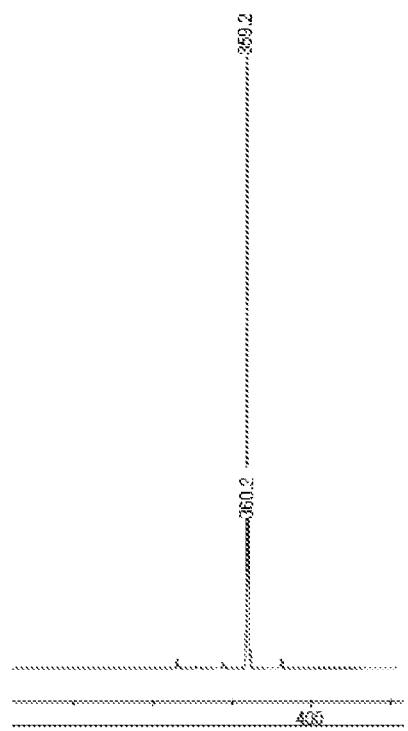
FIG. 8B depicts the MS data of the 2.5 hydrate 3-[2-butyl-1-(2-diethylamino-ethyl)-1H-benzoimidazol-5-yl]-N-hydroxy-acrylamide dihydrochloride (polymorph Form 3).

MS peaks for polymorph Form 3 is shown in FIG. 8B. The MS signal confirmed the molecular weight of 358 g/mol corresponding to the molecular weight of 3-[2-butyl-1-(2-diethylamino-ethyl)-1H-benzoimidazol-5-yl]-N-hydroxy-acrylamide as the free base.

Scanning Electron Microscopy Analysis

Figure 9A:
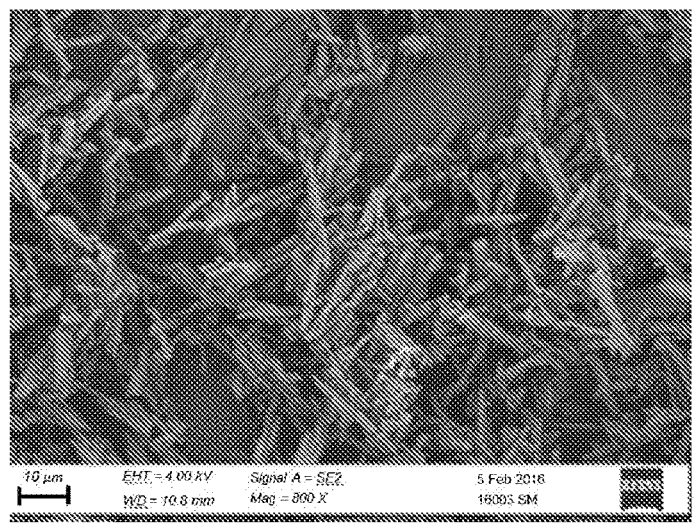
FIG. 9A depicts scanning electron microscopy images of 3-[2-butyl-1-(2-diethylamino-ethyl)-1H-benzoimidazol-5-yl]-N-hydroxy-acrylamide dihydrochloride 2.5 hydrate (800× magnification).
Figure 9B:
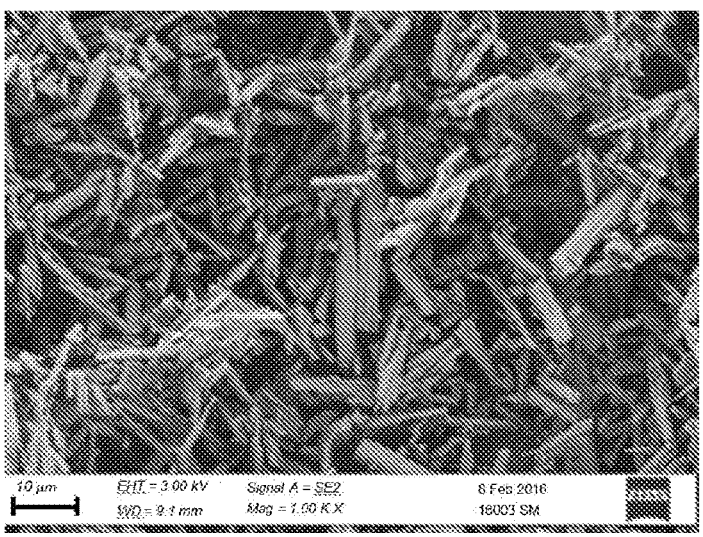
FIG. 9B depicts scanning electron microscopy images of 3-[2-butyl-1-(2-diethylamino-ethyl)-1H-benzoimidazol-5-yl]-N-hydroxy-acrylamide dihydrochloride 2.5 hydrate (1000× magnification).
Figure 9C:
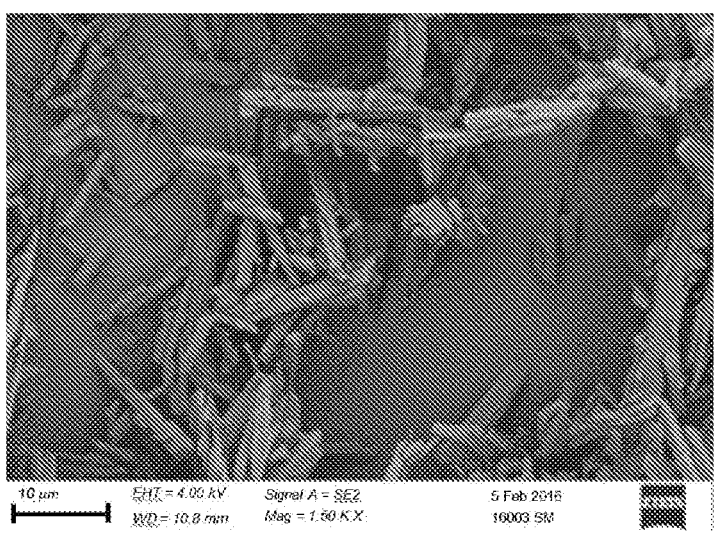
FIG. 9C depicts scanning electron microscopy images of 3-[2-butyl-1-(2-diethylamino-ethyl)-1H-benzoimidazol-5-yl]-N-hydroxy-acrylamide dihydrochloride 2.5 hydrate (1500× magnification).

A sample of the starting material was submitted for imaging by scanning electron microscopy. The 1000-fold magnification provided a good image of the material. The material presented itself as columnar particles (see FIG. 9).

Moisture Sorption Studies

A moisture sorption study was performed to investigate the physical stability of 3-[2-butyl-1-(2-diethylamino-ethyl)-1H-benzoimidazol-5-yl]-N-hydroxy-acrylamide dihydrochloride 2.5 hydrate upon exposure to several relative humidity profiles. HT-XRPD analyses were performed on the solid material obtained after the DVS analyses. The analytical method is described herein.

Figure 10A:
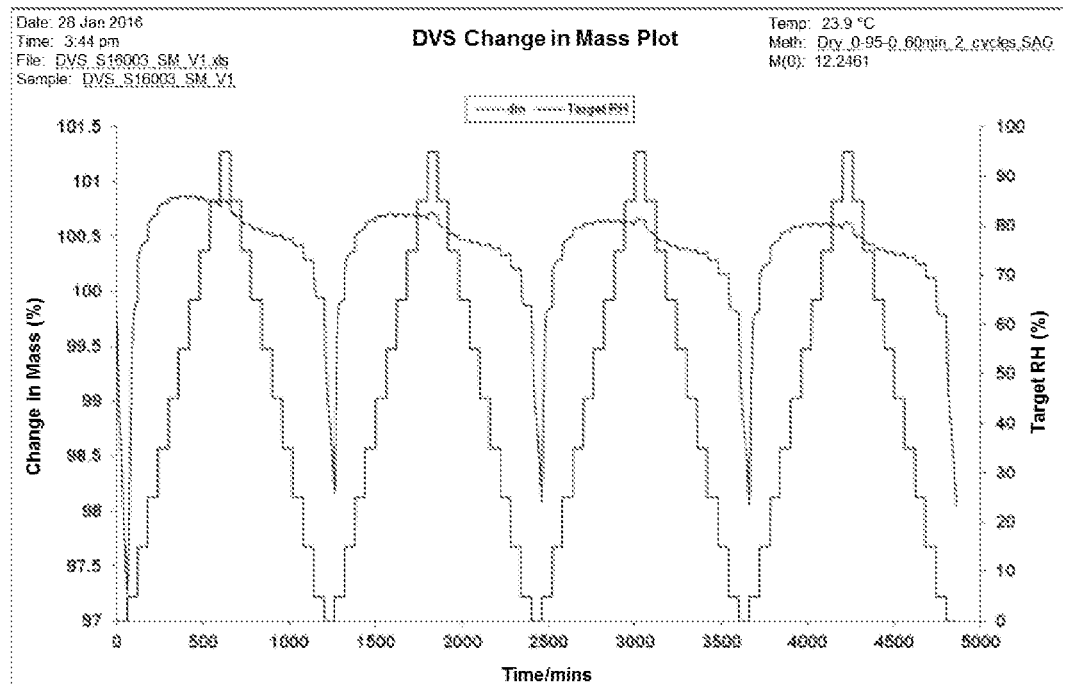
FIG. 10A depicts the DVS mass plot analysis on 3-[2-butyl-1-(2-diethylamino-ethyl)-1H-benzoimidazol-5-yl]-N-hydroxy-acrylamide dihydrochloride 2.5 hydrate (Form 3).
Figure 10B:
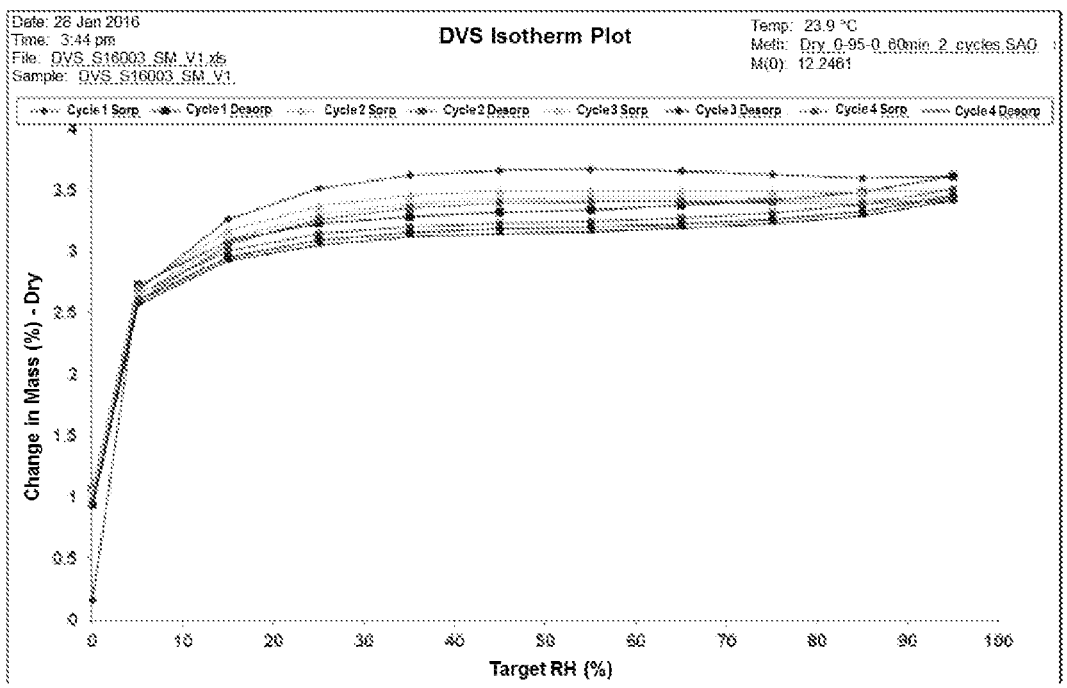
FIG. 10B depicts the DVS isotherm plot analysis on 3-[2-butyl-1-(2-diethylamino-ethyl)-1H-benzoimidazol-5-yl]-N-hydroxy-acrylamide dihydrochloride 2.5 hydrate (Form 3).

The first moisture sorption experiment consisted of four sorption-desorption cycles between 0-95-0% RH. This analysis indicated that 3-[2-butyl-1-(2-diethylamino-ethyl)-1H-benzoimidazol-5-yl]-N-hydroxy-acrylamide dihydrochloride 2.5 hydrate does not change at relative humidity values between 25-95%. However, below 15% RH the water is gradually lost. At 0% RH a mass loss of about 2% was observed (see FIG. 10A and FIG. 10B). Upon increase of the relative humidity, the water loss is reversed and the initial form was recovered. A sorption-desorption cycle 0-95-0% RH was followed by desorption from 95% RH to 0% RH with a stage time of 60 min per step. This cycle was repeated 4 times. At 0% RH a water loss of about 2% was observed. At 5% RH, the water is absorbed again. Similar change in mass profile was observed during the four sorption-desorption cycles.

Figure 11:
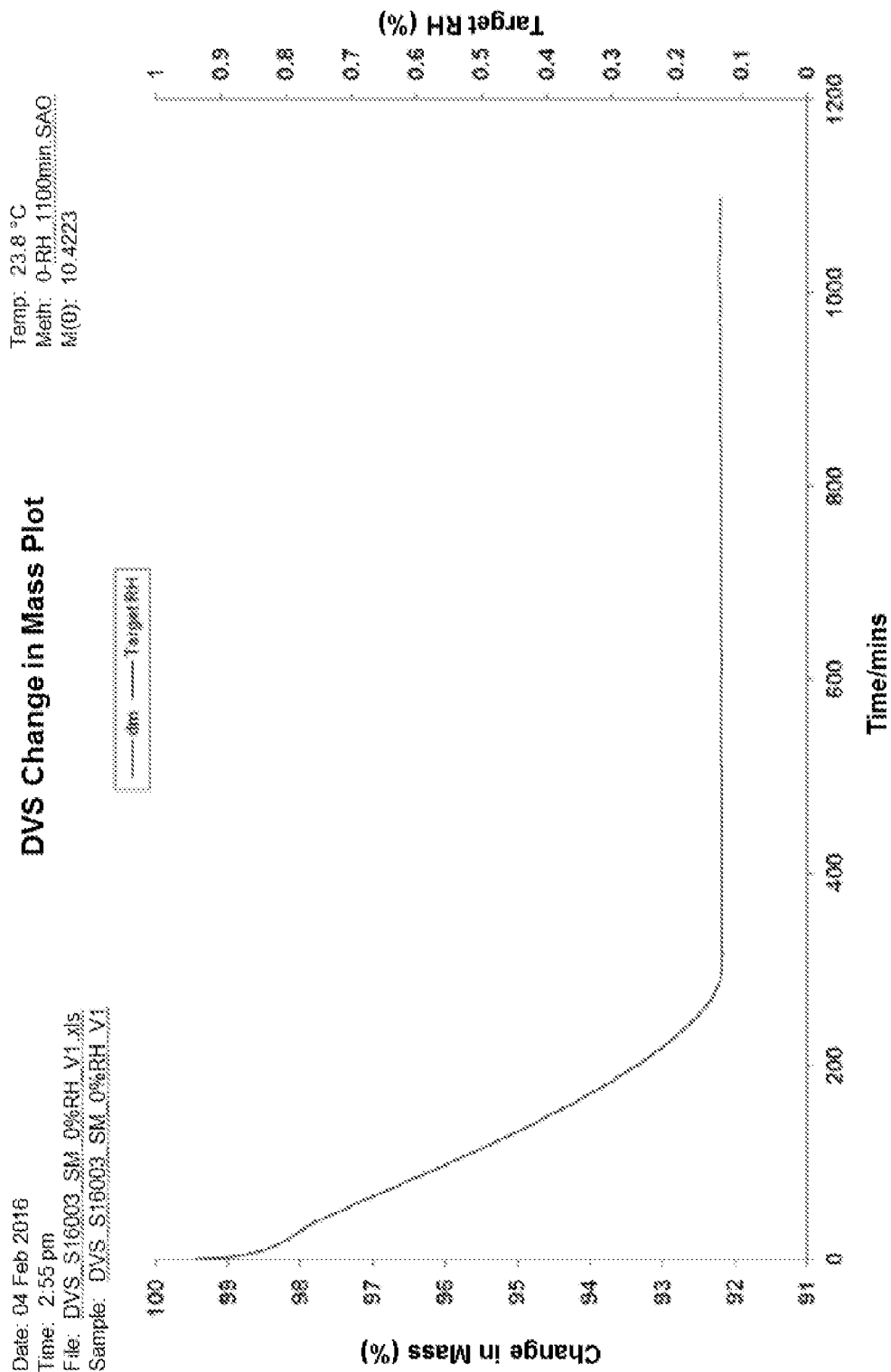
FIG. 11 depicts mass plot DVS analysis on 3-[2-butyl-1-(2-diethylamino-ethyl)-1H-benzoimidazol-5-yl]-N-hydroxy-acrylamide dihydrochloride 2.5 hydrate with a drying protocol at 0% RH for 18 hours.

In order to investigate the desorption profile observed at 0% RH, a DVS analysis at a constant relative humidity level was performed (see FIG. 11). 3-[2-Butyl-1-(2-diethylamino-ethyl)-1H-benzoimidazol-5-yl]-N-hydroxy-acrylamide dihydrochloride 2.5 hydrate was exposed to 0% RH for 18 hours. In the first 5 hours, a gradual loss of water was observed (8%). Thereafter no change in mass was recorded. The HT-XRPD analysis of the recovered solids indicated that the 2.5 hydrate had converted to a new solid form designated Form 6. Form 6 had limited stability and as soon as the relative humidity was above 5%, conversion to the 2.5 hydrate took place.

Figure 12A:
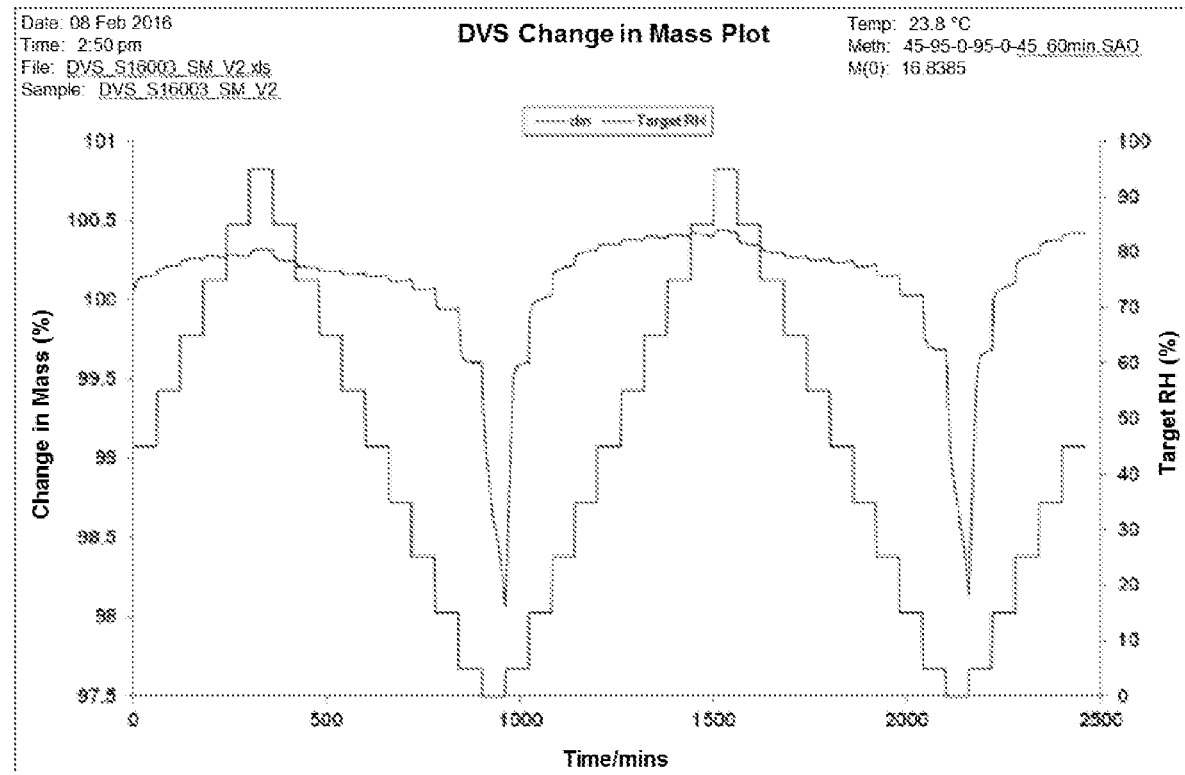
FIG. 12A depicts DVS mass plot analysis on 3-[2-butyl-1-(2-diethylamino-ethyl)-1H-benzoimidazol-5-yl]-N-hydroxy-acrylamide dihydrochloride 2.5 hydrate (Form 3).
Figure 12B:
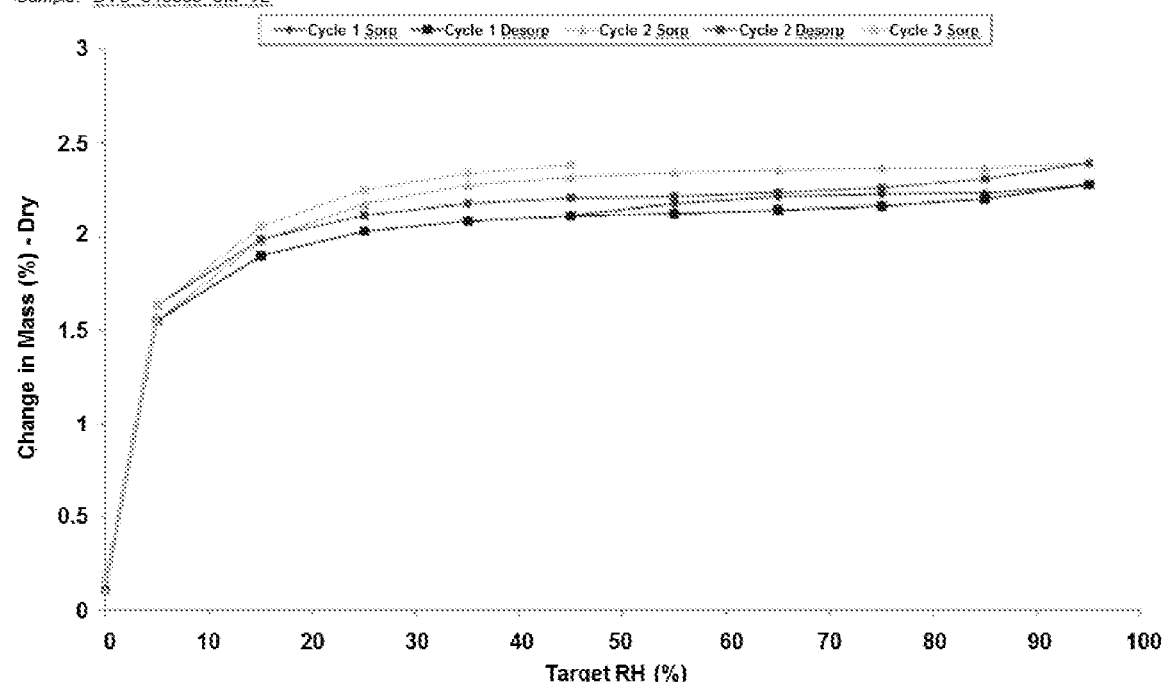
FIG. 12B depicts DVS isotherm plot analysis on 3-[2-butyl-1-(2-diethylamino-ethyl)-1H-benzoimidazol-5-yl]-N-hydroxy-acrylamide dihydrochloride 2.5 hydrate (Form 3).

This result was confirmed with a DVS experiment performed on the 2.5 hydrate (polymorph Form 3). This analysis consisted of two sorption-desorption cycles from 45-95-0-95-0-45% RH (see FIG. 12A and FIG. 12B). A sorption cycle from 45-95% RH was followed by desorption from 95% RH to 0%, sorption to 95% RH, desorption to 0% RH and sorption to 45% RH. A water loss of about 2% was observed between 5-0% RH. The water is again absorbed upon increasing the relative humidity.

Figure 13:
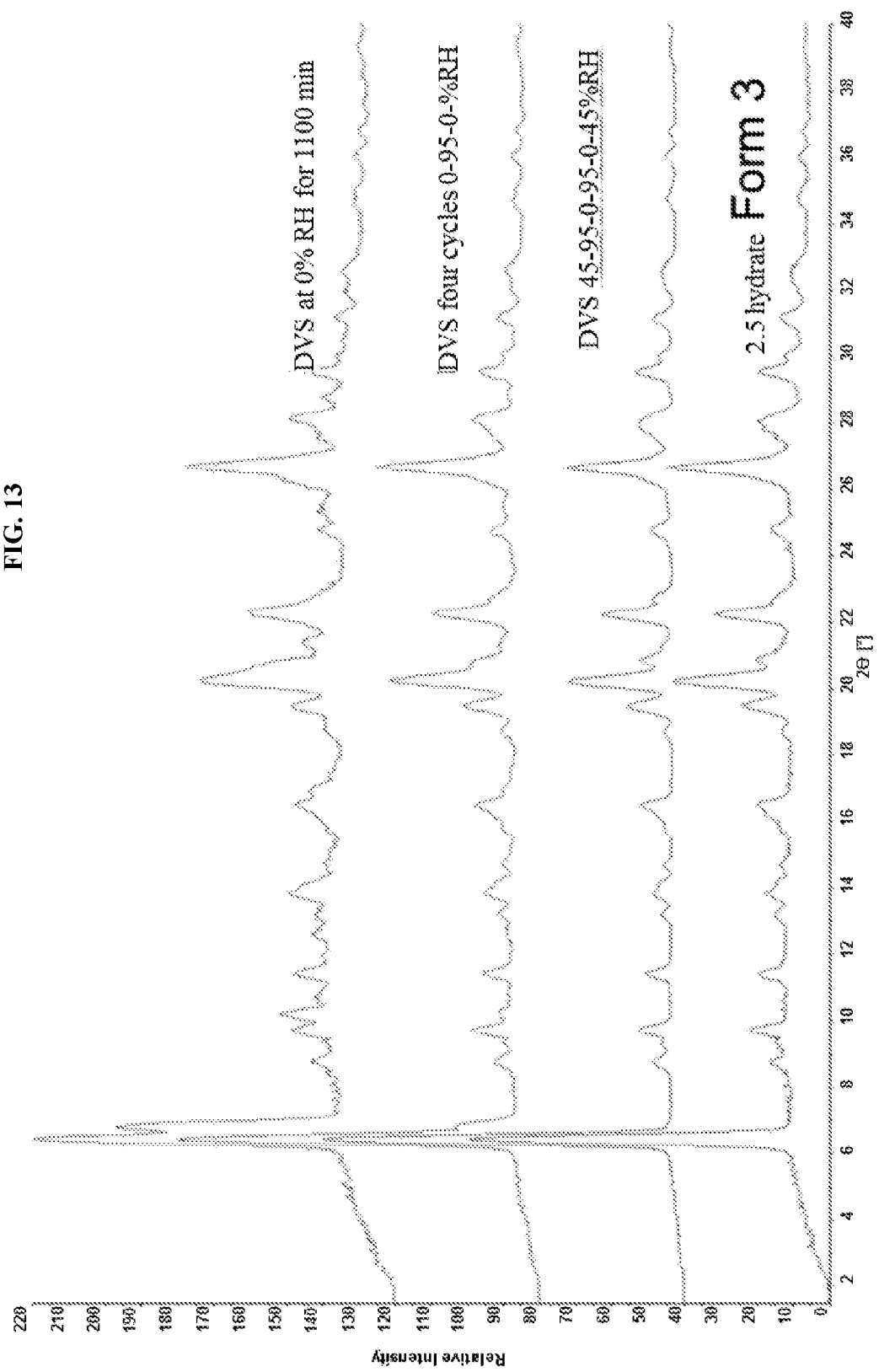
FIG. 13 depicts an overlay of XRPD patterns (from bottom to top): 3-[2-butyl-1-(2-diethylamino-ethyl)-1H-benzoimidazol-5-yl]-N-hydroxy-acrylamide dihydrochloride 2.5 hydrate (Form 3), 2.5 hydrate (Form 3) as obtained after the DVS analysis 45-95-0-45% RH, Form 3 (2.5 hydrate)+Form 6 as obtained after the DVS analysis 0-95-0-95-0-95-0-95-0% RH and Form 3 (2.5 hydrate)+Form 6 as obtained after drying Form 3 (the 2.5 hydrate) after 1100 min at 0% RH.

After this relative humidity profile the 2.5 hydrate was recovered (see FIG. 13). These results indicate the 2.5 hydrate is not hygroscopic.

Variable Temperature and Humid XRPD Analysis of Polymorph Form 3

3-[2-Butyl-1-(2-diethylamino-ethyl)-1H-benzoimidazol-5-yl]-N-hydroxy-acrylamide dihydrochloride 2.5 hydrate (polymorph Form 3) was analyzed by variable humidity XRPD to investigate in more detail the dynamics of form conversion upon exposure to variable relative humidity levels. The analytical method is described herein.

Figure 14:
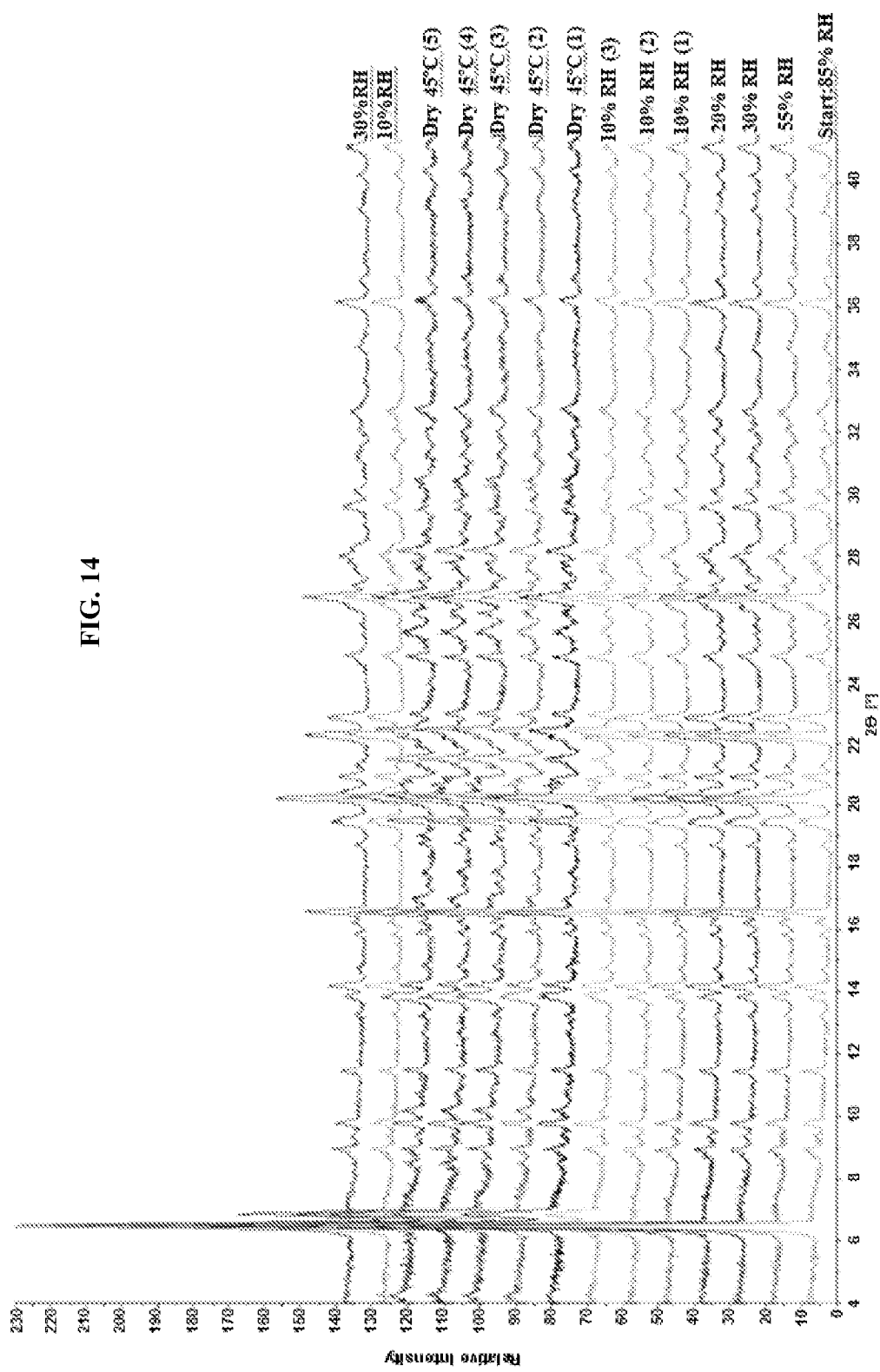
FIG. 14 depicts an overlay of XRPD patterns obtained from the variable humidity XRPD measurements of 3-[2-butyl-1-(2-diethylamino-ethyl)-1H-benzoimidazol-5-yl]-N-hydroxy-acrylamide dihydrochloride 2.5 hydrate (Form 3) at 30° C. (sequence from bottom to top). The number between the brackets indicates that the conditions were maintained with a waiting time of 45 minutes before X-ray data collection.
Figure 15:
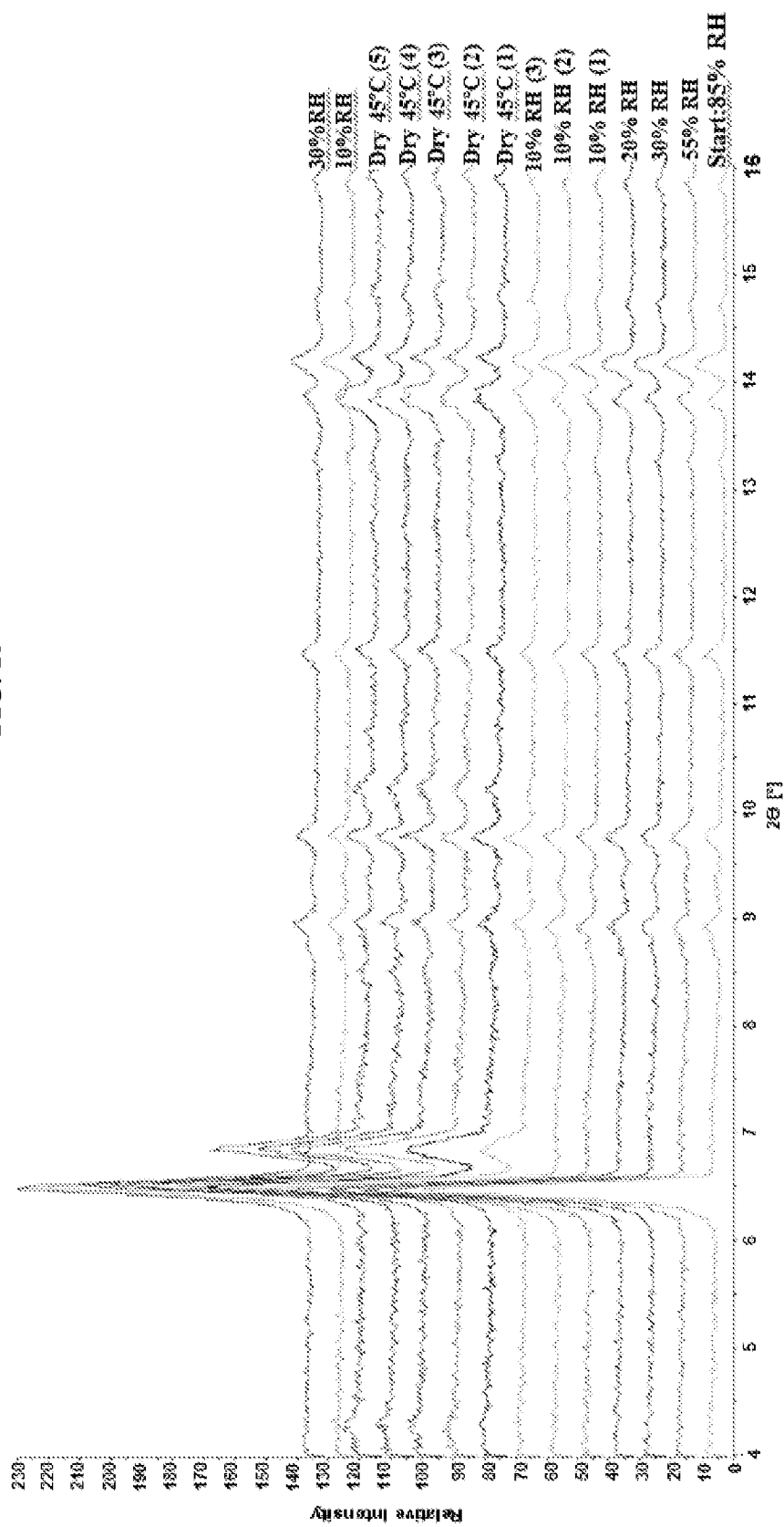
FIG. 15 depicts an overlay of XRPD patterns (zoomed in on region 4-16°2θ) obtained from the variable humidity XRPD measurements of 3-[2-butyl-1-(2-diethylamino-ethyl)-1H-benzoimidazol-5-yl]-N-hydroxy-acrylamide dihydrochloride 2.5 hydrate (Form 3) at 30° C. (sequence from bottom to top). The number between the brackets indicates that the conditions were held for 15 min (per step) before recording X-Ray diffraction.

The variable humidity XRPD analysis indicated that between 85-10% RH 3-[2-butyl-1-(2-diethylamino-ethyl)-1H-benzoimidazol-5-yl]-N-hydroxy-acrylamide dihydrochloride 2.5 hydrate (polymorph Form 3) is physically stable. Upon desorption at relative humidity values below 10% additional diffraction peaks became visible. These diffraction peaks corresponded to a new crystalline phase. The main diffraction peak of this new crystalline phase was located at $6.8°2\theta$ and corresponded to Form 6. This form was physically stable at relative humidity values below 10%. At values above 10% RH Form 6 converted to the 2.5 hydrate (polymorph Form 3). The collected XRPD patterns are shown in FIG. 14 and FIG. 15. FIG. 14: at relative humidity values between 85-10% RH the 2.5 hydrate (Form 3) seems to be physically stable. An attempt to get a relative humidity below 10% was made by drying the sample at 45° C. Upon exposure to these conditions, a phase contamination was visible (diffraction peak at $6.8°2\theta$). FIG. 15: the main peak corresponding to the phase contamination was visible at $6.8°2\theta$. After 45 min at 10% RH, the phase contamination was initially observed. Upon drying the sample at 45° C. the phase contamination increased. However, full conversion to this new phase was not completed after 3 hours at 45° C. and <10% RH. Increasing the relative humidity to 10% RH leads to the pure 2.5 hydrate (Form 3) being observed.

The results obtained during the variable humidity XRPD and DVS analysis indicate that 3-[2-butyl-1-(2-diethylamino-ethyl)-1H-benzoimidazol-5-yl]-N-hydroxy-acrylamide dihydrochloride 2.5 hydrate (Form 3) is physically stable at relative humidity levels above 10%. Below 10% RH part of the 2.5 hydrate converts into Form 6.

Example 4: Analysis of Monohydrate Polymorph Form 1

X-Ray Powder Diffraction of Form 1

Both a HR-XRPD and HT-XRPD of the obtained 3-[2-butyl-1-(2-diethylamino-ethyl)-1H-benzoimidazol-5-yl]-N-hydroxy-acrylamide dihydrochloride monohydrate were recorded (see FIG. 16). The HR-XRPD confirmed one single phase. The cell parameters were determined by indexing the HR-XRPD pattern. Based on the calculated density of the crystal cell the water content was estimated to be one molecule of water per molecule of API confirming the monohydrated nature of this form. The determined cell parameters are presented in Table 12.

TABLE 12

| Identification code | Monohydrate |
|---|---|
| Empirical formula | $C_{20}H_{32}N_4O_2^+ \cdot 2Cl^- \cdot H_2O$ |
| Fw | 449.32 |
| Empirical formula | $C_{20}H_{32}N_4O_2^+ \cdot 2Cl^- \cdot 0.5 H_2O$ |
| Fw | 440.41 |
| T [K] | 296 (2) |
| λ [Å] | 1.5418 |
| Crystal system | Monoclinic |
| Space group | $P2_1/n$ |

TABLE 12-continued

| Unit cell dimensions | |
|---|---|
| a [Å] | 7.2627 (6) |
| b [Å] | 27.148 (3) |
| c [Å] | 12.3879 (2) |
| β [°] | 98.360 (6) |
| V [Å$^3$] | 2416.5 (4) |
| Z (Z') | 4 (1) |
| D$_c$ [g/cm$^3$] | 1.235 |
| D$_c$ [g/cm$^3$] | 1.210 |
| Capillary size [mm$^2$] | 0.3 × 8 |
| 2θ Step size [°] | 0.016 |
| No of steps | 2377 |
| Time per step [s] | 20 |
| 2θ range [°] | 4 → 41.5 |
| Rexp | 1.79 |
| R$_{wp}$ | 3.14 |
| R$_p$ | 2.44 |
| GOF | 1.75 |
| R$_{Brag}$ | 0.09 |
| Amorphous Content [%] | Not determined |

Thermal Analyses of Form 1

The DSC trace showed one broad endotherm was observed between 25-120° C. followed by an exothermic event at 228.8° C. most likely corresponding to the thermal decomposition of the hydrochloride salt (see FIG. 17). The TGMS analysis confirmed the hydrated nature of the material (see FIG. 18A and FIG. 18B). A mass loss of 3.1% was observed over the temperature range 25-200° C. This mass loss corresponded to 0.8 molecules of water per molecule of API. The Karl Fischer analysis indicated that this material contained 3.3% of water, which equated to 0.8 molecules of water.

The TGMS analysis performed on the reference material in batch DBDE8002 showed a mass loss of 4.3% corresponding to 1.1 molecules of water. The Karl Fischer analysis also confirmed a water content of 4.4% (corresponding to 1.1 molecules of water). Therefore, it seems that the monohydrated form of 3-[2-butyl-1-(2-diethylamino-ethyl)-1H-benzoimidazol-5-yl]-N-hydroxy-acrylamide dihydrochloride can have a variable water content (3.3-4.3% of water). See FIGS. 34-37 for analysis of the Form 1 reference material (X-ray Powder Diffraction, DSC analysis, TGA/SDTA analysis, and TGMS analysis).

Variable Temperature XRPD Analysis of Form 1

Figure 19:
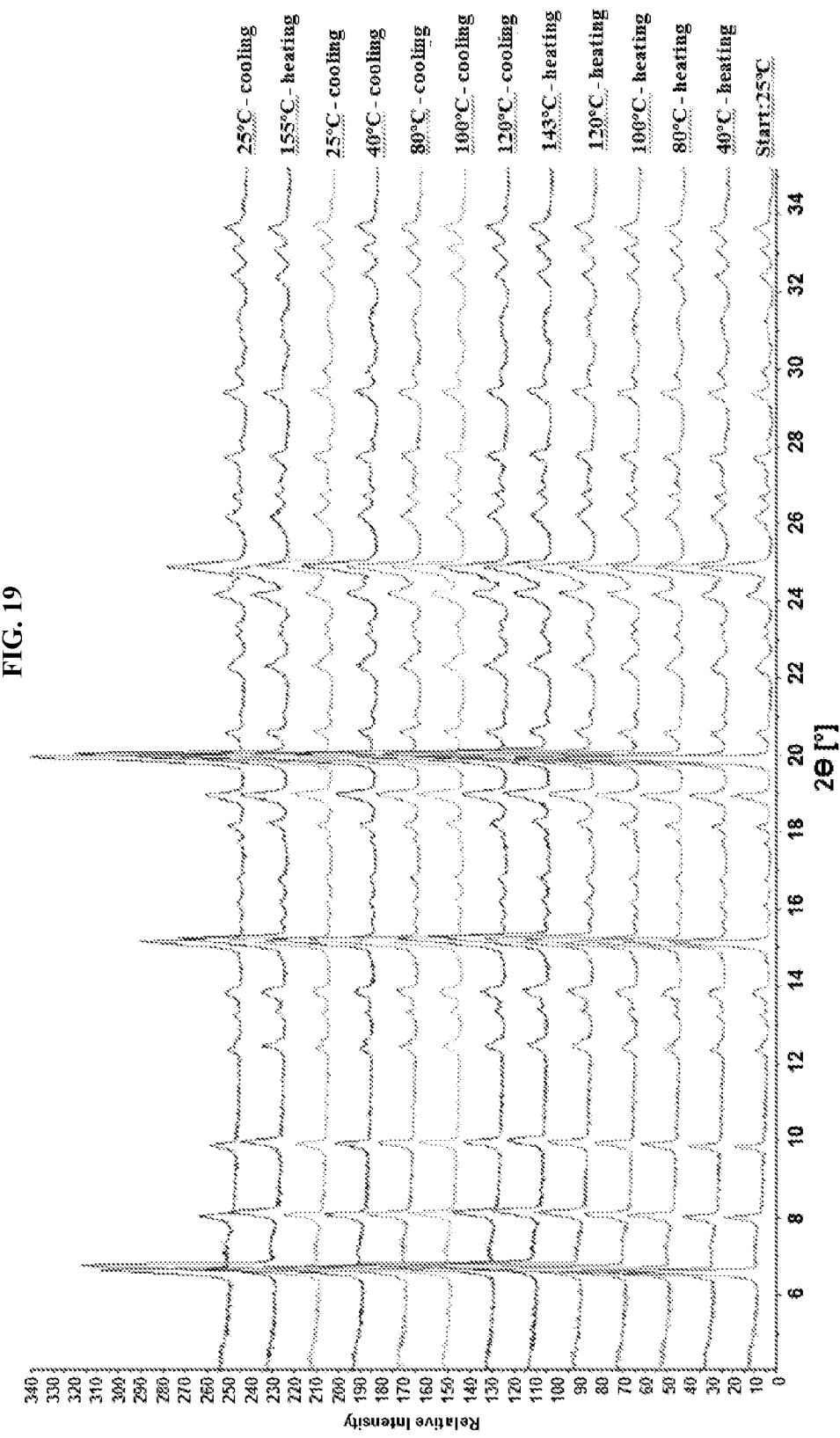
FIG. 19 depicts an overlay of XRPD patterns obtained from the variable temperature XRPD measurements of 3-[2-butyl-1-(2-diethylamino-ethyl)-1H-benzoimidazol-5-yl]-N-hydroxy-acrylamide dihydrochloride monohydrate (Form 1) between 25-155° C. (sequence from bottom to top).

A variable temperature XRPD experiment with 3-[2-butyl-1-(2-diethylamino-ethyl)-1H-benzoimidazol-5-yl]-N-hydroxy-acrylamide dihydrochloride monohydrate was conducted to investigate the solid form conversion that occurred upon heating. The experiment was run between 25° C. to 143° C. followed by cooling to 25° C., reheating to 155° C. and then cooling again to 25° C. (see FIG. 19).

Figure 20:
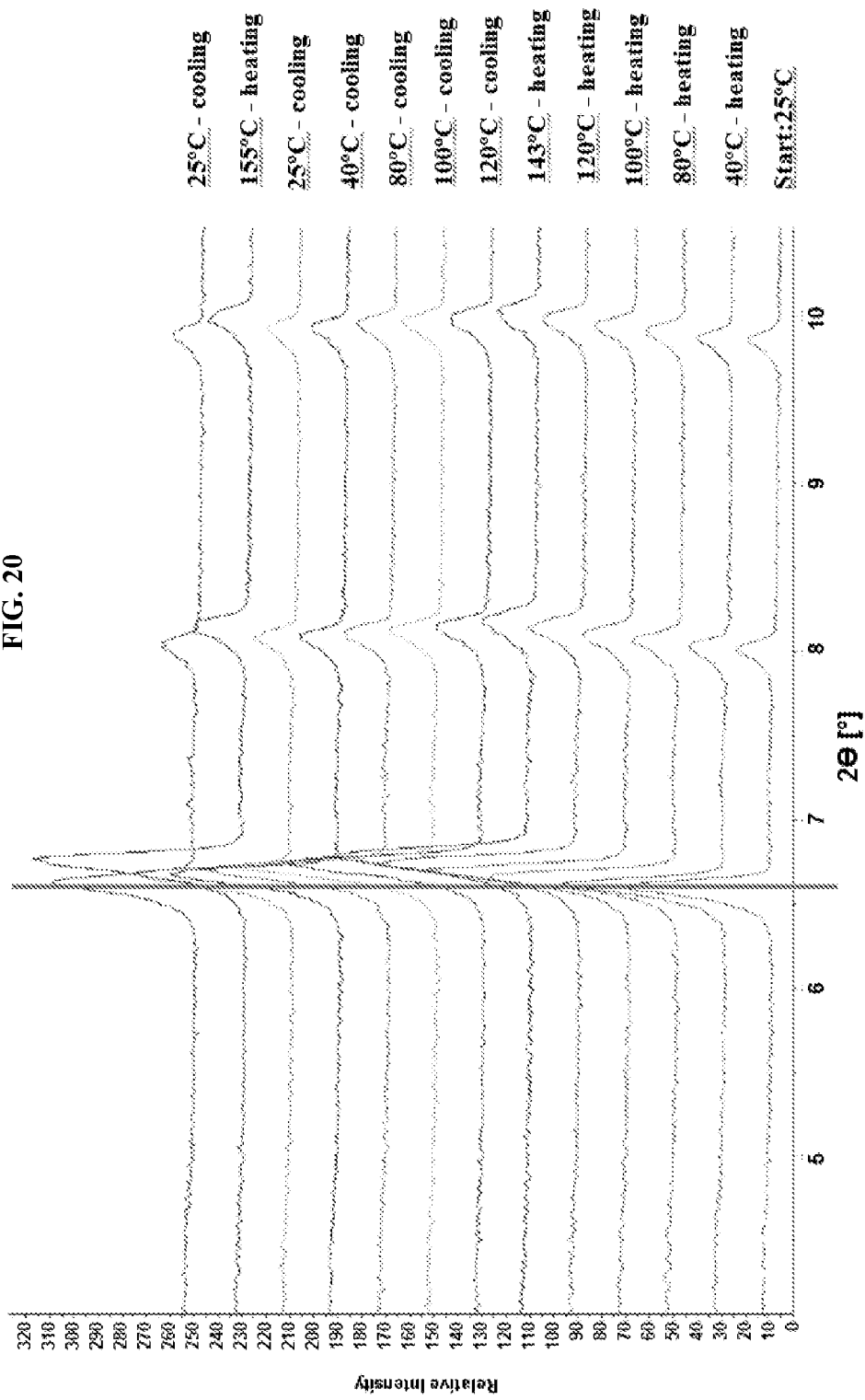
FIG. 20 depicts an overlay of XRPD patterns measurements (zoomed in on region 4-10°2θ) obtained from the variable temperature XRPD of 3-[2-butyl-1-(2-diethylamino-ethyl)-1H-benzoimidazol-5-yl]-N-hydroxy-acrylamide dihydrochloride monohydrate (Form 1) between 25-155° C. (sequence from bottom to top).

No solid form conversions were observed. Small shifts in the diffraction peaks of the monohydrate were noticed upon heating which were more intense at 155° C. (see FIG. 20). The vertical line highlights diffraction peaks shifted observed at 155° C. It seems that at elevated temperatures the crystal cell shrunk due to most likely a partial water loss. As soon as the temperature is decreased, the cell recovered its initial size.

HPLC Analysis

Figure 21A:
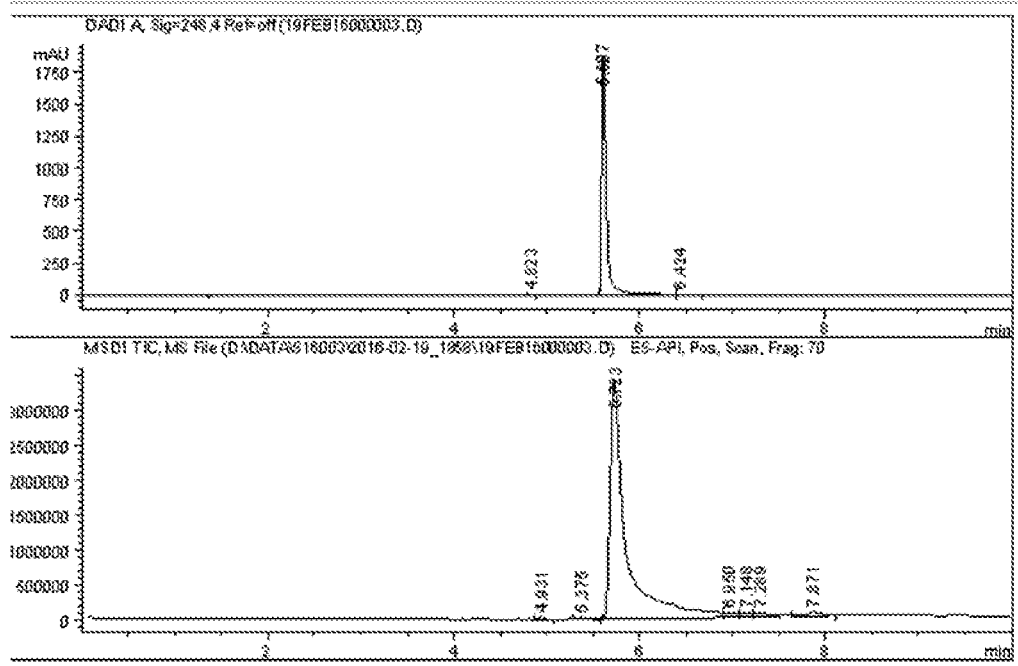
FIG. 21A depicts the HPLC data of the monohydrate 3-[2-butyl-1-(2-diethylamino-ethyl)-1H-benzoimidazol-5-yl]-N-hydroxy-acrylamide dihydrochloride (polymorph Form 1).

The HPLC trace of polymorph Form 1 is shown in FIG. 21A. The main peak was observed at a retention time of 5.6 min with a chemical purity of 99.5% (area %). The peak listing for the trace is given in the table below.

| Peak # | Ret time (min) | Type | Width (min) | Area (mAU*s) | Height (mAU) | Area (%) |
|---|---|---|---|---|---|---|
| 1 | 4.823 | BB | 0.0306 | 6.03995 | 2.98612 | 0.0944 |
| 2 | 5.607 | BV | 0.0484 | 6366.15771 | 1885.48840 | 99.4799 |
| 3 | 6.424 | VB | 0.1150 | 27.24646 | 2.94199 | 0.4258 |

Mass Spectrometry Analysis

Figure 21B:
FIG. 21B depicts the MS data of the monohydrate 3-[2-butyl-1-(2-diethylamino-ethyl)-1H-benzoimidazol-5-yl]-N-hydroxy-acrylamide dihydrochloride (polymorph Form 1).

MS peaks for polymorph Form 1 is shown in FIG. 21B. The MS signal confirmed the molecular weight of 358 g/mol corresponding to the molecular weight of 3-[2-butyl-1-(2-diethylamino-ethyl)-1H-benzoimidazol-5-yl]-N-hydroxy-acrylamide as the free base.

Scanning Electron Microscopy

Figure 22A:
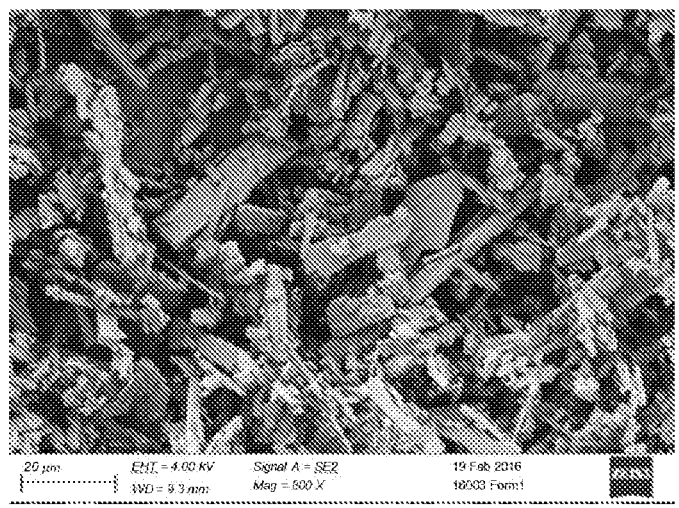
FIG. 22A depicts scanning electron microscopy images of 3-[2-butyl-1-(2-diethylamino-ethyl)-1H-benzoimidazol-5-yl]-N-hydroxy-acrylamide dihydrochloride monohydrate (Form 1) (800× magnification).
Figure 22B:
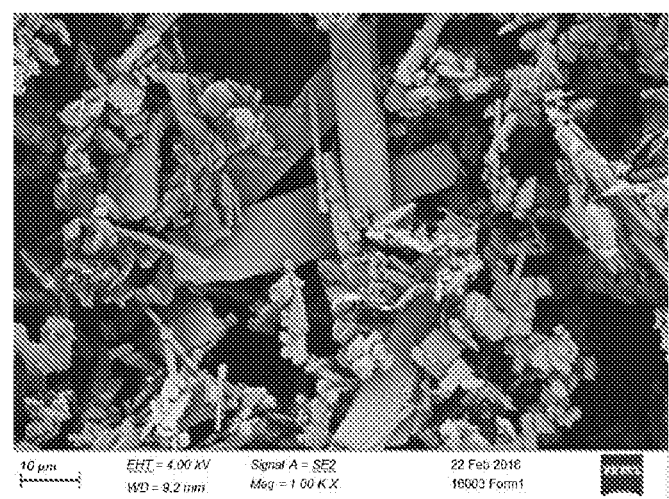
FIG. 22B depicts scanning electron microscopy images of 3-[2-butyl-1-(2-diethylamino-ethyl)-1H-benzoimidazol-5-yl]-N-hydroxy-acrylamide dihydrochloride monohydrate (Form 1) (1000× magnification).
Figure 22C:
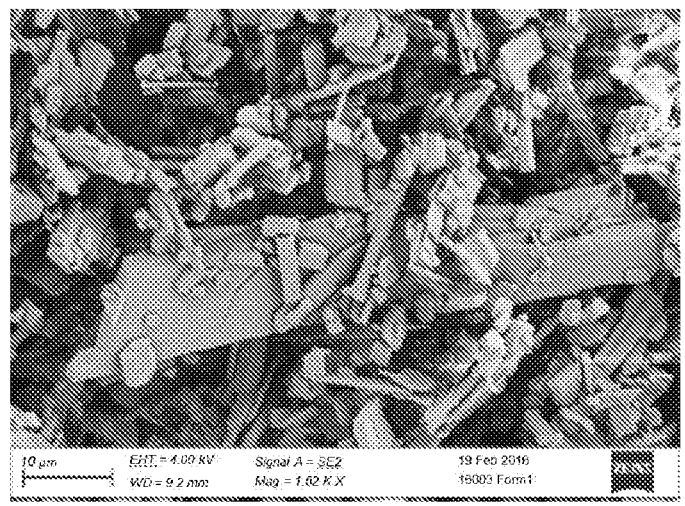
FIG. 22C depicts scanning electron microscopy images of 3-[2-butyl-1-(2-diethylamino-ethyl)-1H-benzoimidazol-5-yl]-N-hydroxy-acrylamide dihydrochloride monohydrate (Form 1) (1500× magnification).

A sample of the monohydrate Form 1 was analyzed by scanning electron microscopy. The 800-fold magnification indicated that the material crystallized as cubes of different sizes and dimensions (see FIG. 22).

Moisture Sorption Studies

Figure 23A:
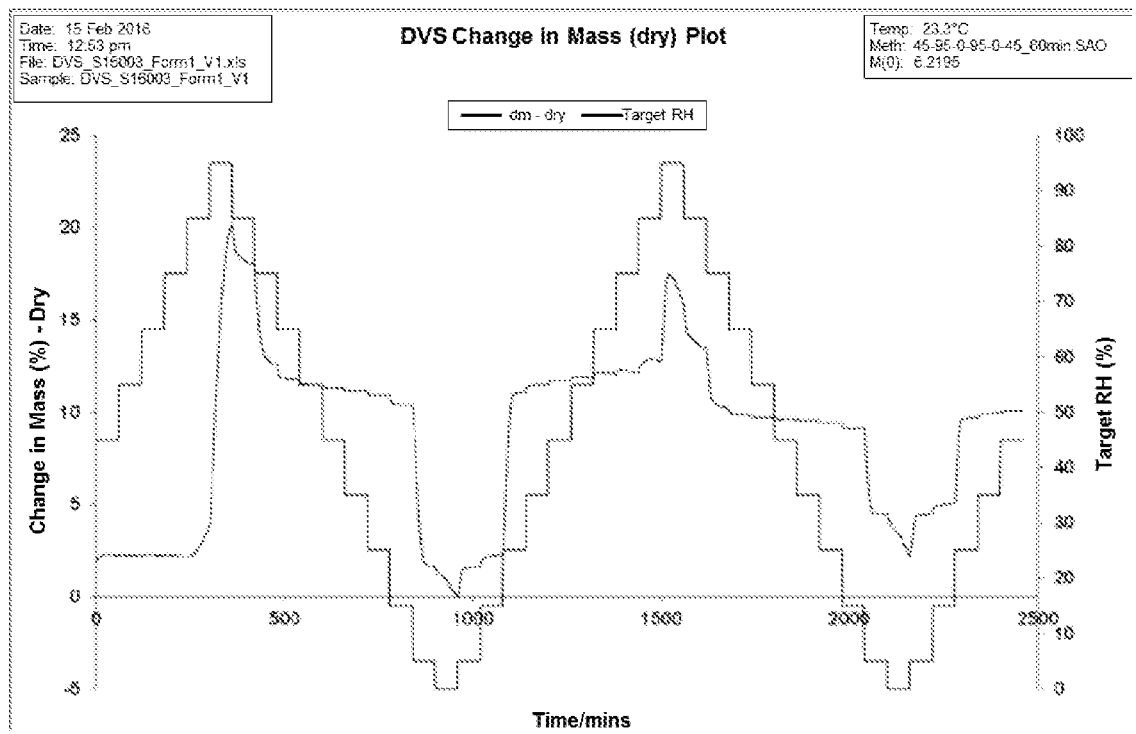
FIG. 23A depicts DVS mass plot analysis on 3-[2-butyl-1-(2-diethylamino-ethyl)-1H-benzoimidazol-5-yl]-N-hydroxy-acrylamide dihydrochloride monohydrate (Form 1).
Figure 23B:
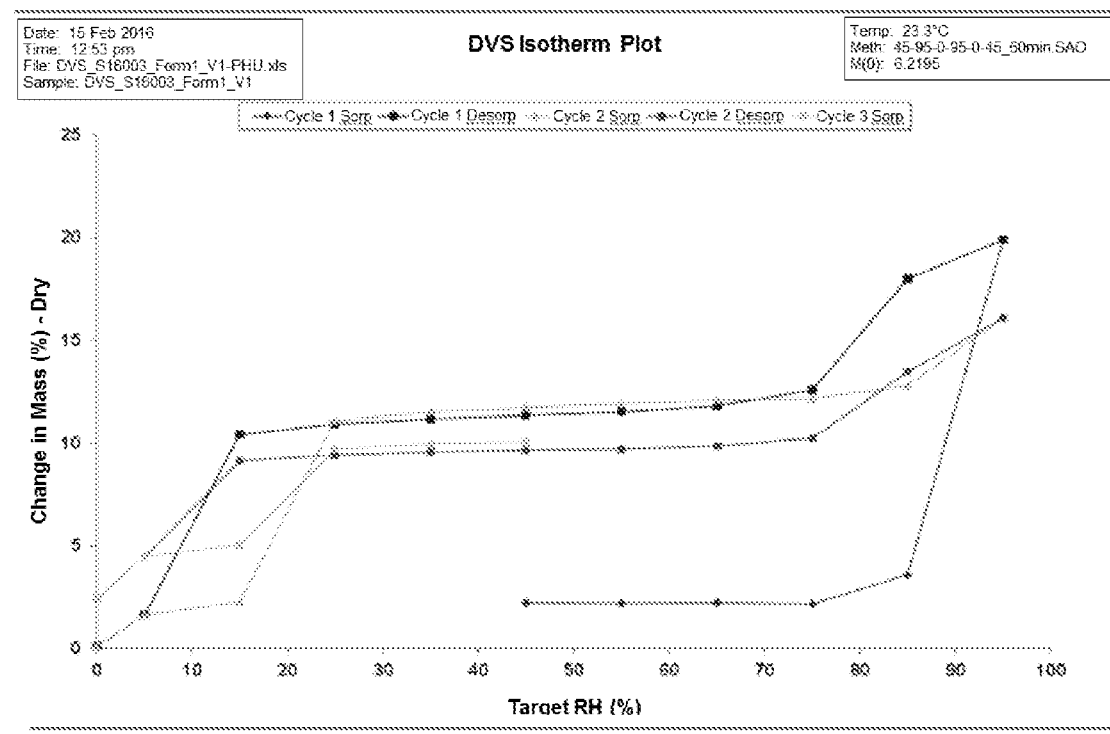
FIG. 23B depicts DVS isotherm plot analysis on 3-[2-butyl-1-(2-diethylamino-ethyl)-1H-benzoimidazol-5-yl]-N-hydroxy-acrylamide dihydrochloride monohydrate (Form 1).

The hygroscopic behavior of polymorph Form 1 was studied by several DVS experiments. The relative humidity was cycled between 45-95-0-45% for two cycles (see FIG. 23A and FIG. 23B). A sorption cycle from 45-95% RH followed by desorption from 95% RH to 0%, sorption to 95% RH, desorption to 0% RH and sorption to 45% RH. A water uptake of 17% was observed between 85-95% RH. During desorption a weight loss of 7% was recorded between 95-75% RH and 10% between 15-0% RH. Similar hygroscopicity behavior was observed in the second cycle. On the first cycle, a water uptake of 18% was recorded at 75% RH that was fully reversible when the humidity was decreased again. However, the weight loss was recorded in two steps—7% from 95-75% RH and about 10% between 15-0% RH. Between 75-15% RH, no significant changes in weight were recorded. On the second cycle, a similar water absorption and desorption profile was observed. After the DVS analysis, the solid was analyzed by HT-XRPD confirming a conversion mainly to the 2.5 hydrate (Form 3). However, a few additional diffraction peaks were observed. This phase contamination might be attributed to a hemihydrate form (Form 10), discovered during the attempts to produce the monohydrate (Form 1).

Figure 24A:
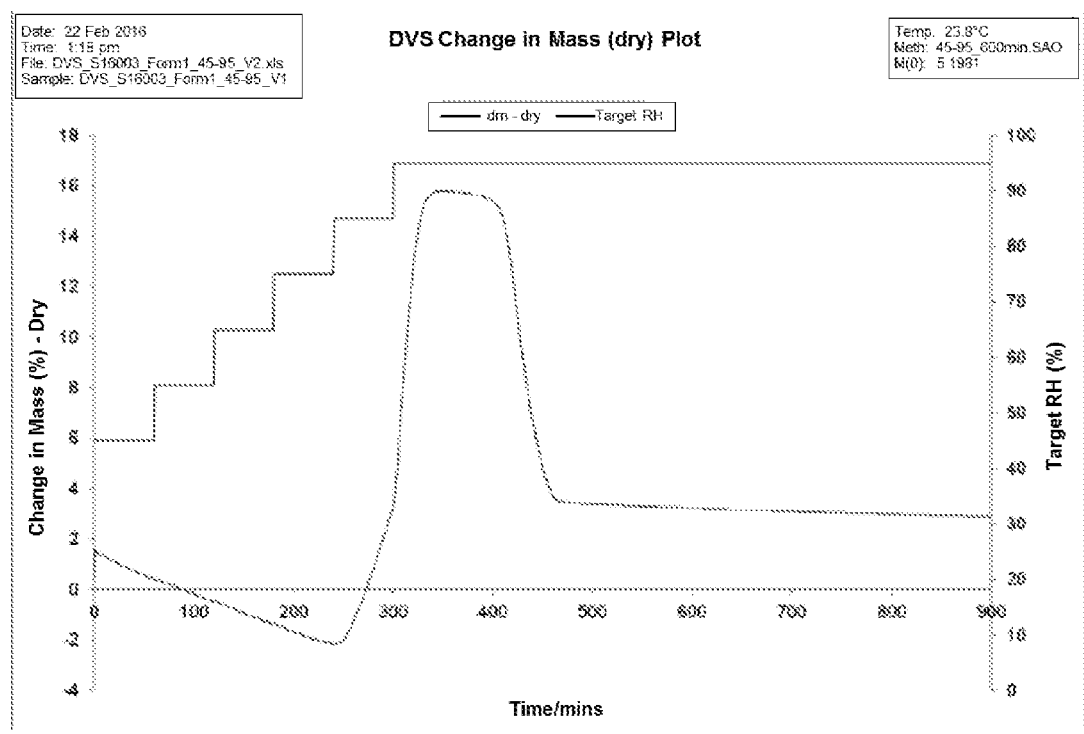
FIG. 24A depicts DVS analyses on 3-[2-butyl-1-(2-diethylamino-ethyl)-1H-benzoimidazol-5-yl]-N-hydroxy-acrylamide dihydrochloride monohydrate (Form 1) with one sorption cycle from 45-95% RH.
Figure 24B:
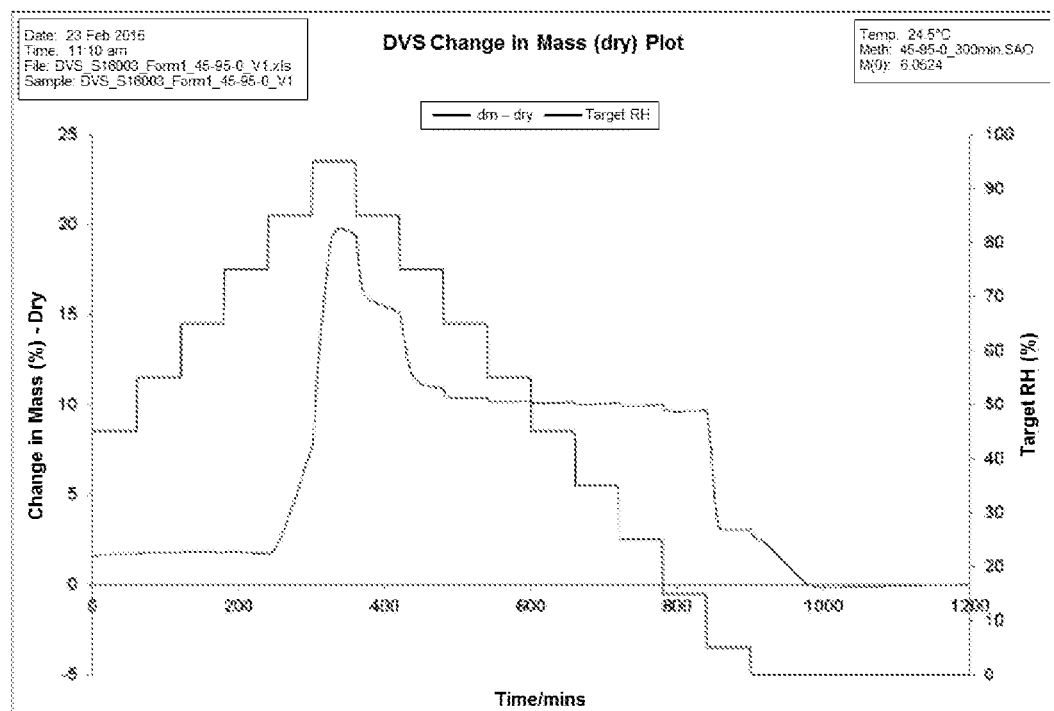
FIG. 24B depicts DVS analyses on 3-[2-butyl-1-(2-diethylamino-ethyl)-1H-benzoimidazol-5-yl]-N-hydroxy-acrylamide dihydrochloride monohydrate (Form 1) with one sorption from 45-95% RH followed by desorption from 95-0% RH.
Figure 25:
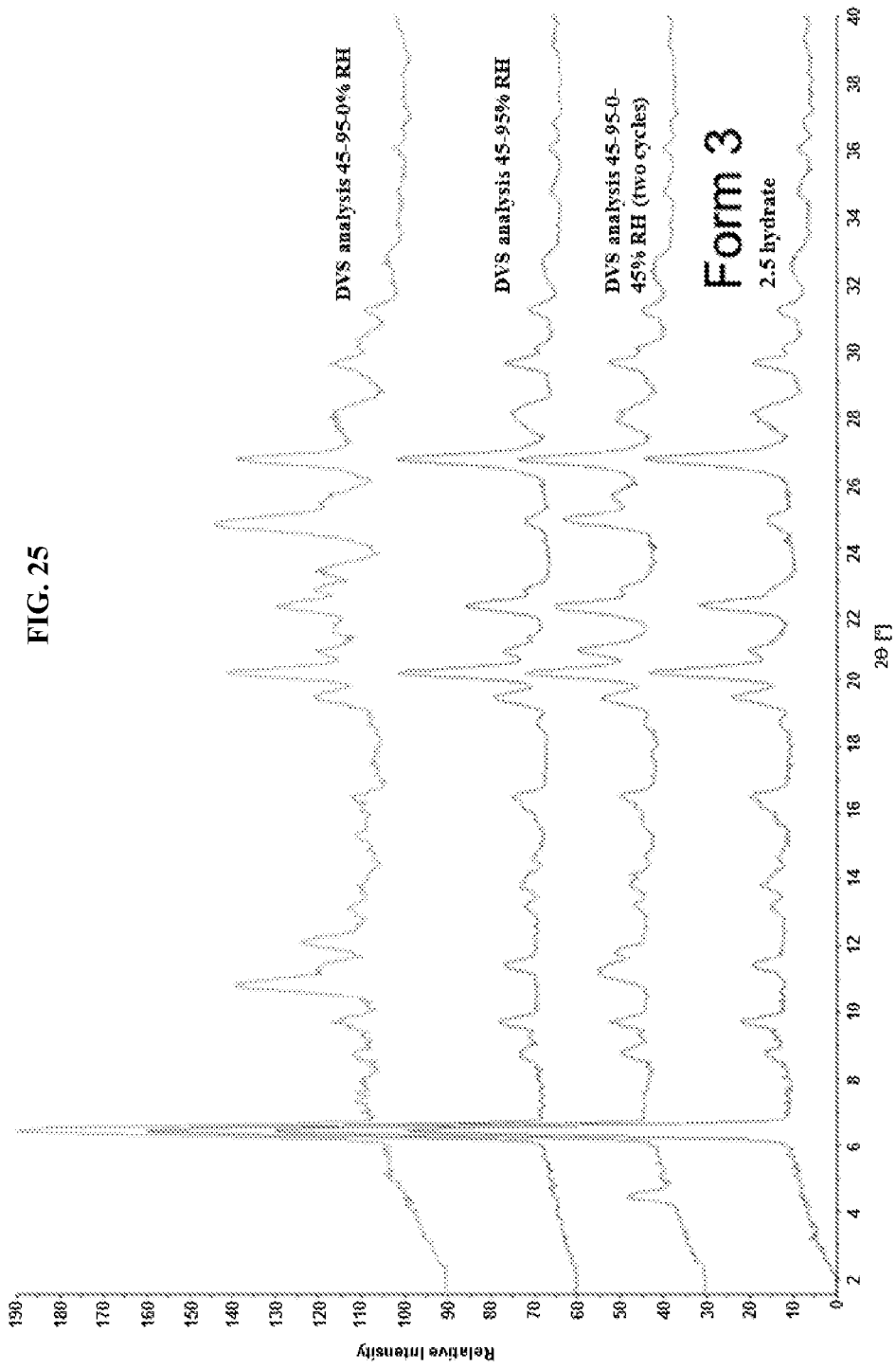
FIG. 25 depicts an overlay of XRPD patterns (from bottom to top): 3-[2-butyl-1-(2-diethylamino-ethyl)-1H-benzoimidazol-5-yl]-N-hydroxy-acrylamide dihydrochloride 2.5 hydrate (Form 3), 2.5 hydrate (Form 3)+hemihydrate (Form 10) as obtained after the DVS analysis 45-95-0-45% RH (two cycles), 2.5 hydrate (Form 3) as obtained after the DVS analysis 45-95% RH and 2.5 hydrate (Form 3)+hemihydrate (Form 10) as obtained after DVS analysis 45-95-0% RH.

In order to investigate the solid form conversion of the monohydrate Form 1 at relative humidity levels above 75%, a second DVS analysis was performed increasing the relative humidity from 45% to 95% and holding the sample at 95% RH for 10 hours (see FIG. 24A and FIG. 24B). A water uptake of 18% was recorded between 85-95% RH. Nevertheless, after aging at 95% RH for 2 hours, a weight loss of about 12% was observed. This event was attributed to the re-crystallization of the monohydrate (Form 1) to the 2.5 hydrate (Form 3). The 2.5 hydrate (Form 3) was recovered after this DVS analysis confirming that the monohydrate (Form 1) converted to the 2.5 hydrate (Form 3) at relative humidity levels above 85% (see FIG. 25).

A DVS analysis was performed to investigate the solid form conversion that was occurring upon desorption. The relative humidity was varied from 45-95-0% RH with aging for 5 hours at 0% RH. The hygroscopicity profile was similar to that previously obtained. The recovered solid analyzed by HT-XRPD was the 2.5 hydrate (Form 3) with a small contamination of the hemihydrate (Form 10). The hemihydrate (Form 10) appeared to be formed when 0% RH is reached. However, this form was physically unstable and under ambient conditions converted to the 2.5 hydrate (Form 3).

Variable Temperature and Humid XRPD Analysis of Polymorph Form 1

Pracinostat dihydrochloride monohydrate (Form 1) was analyzed by variable humidity XRPD to investigate in more detail the dynamics of form conversion upon exposure to variable relative humidity levels. The analytical method is described herein.

Figure 26:
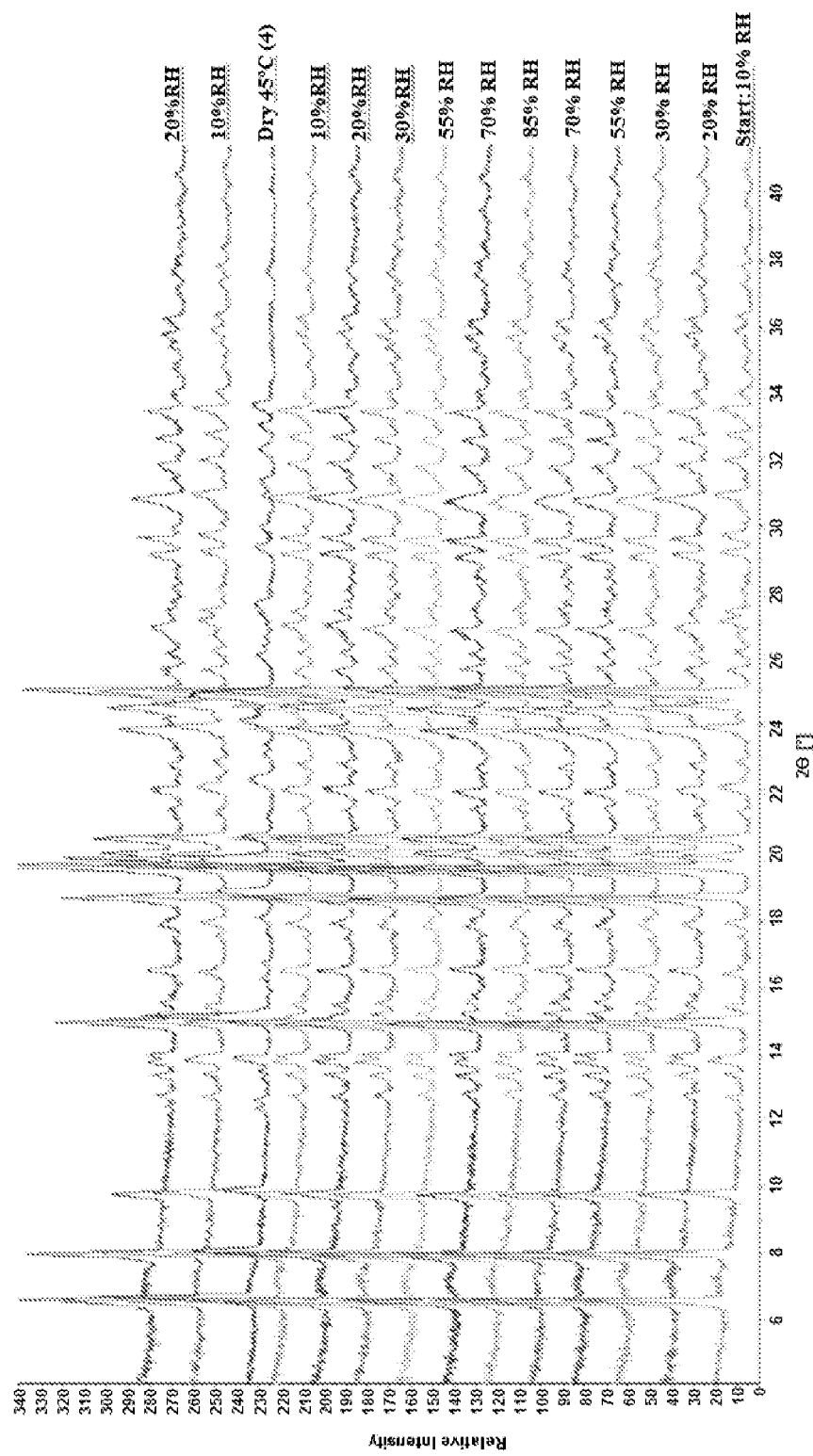
FIG. 26 depicts an overlay of XRPD patterns obtained from the variable humidity XRPD measurements of 3-[2-butyl-1-(2-diethylamino-ethyl)-1H-benzoimidazol-5-yl]-N-hydroxy-acrylamide dihydrochloride monohydrate (Form 1) at 30° C. (sequence from bottom to top). The number between the brackets indicates that the conditions were hold for 15 min (per step) before X-ray data collection.
Figure 27:
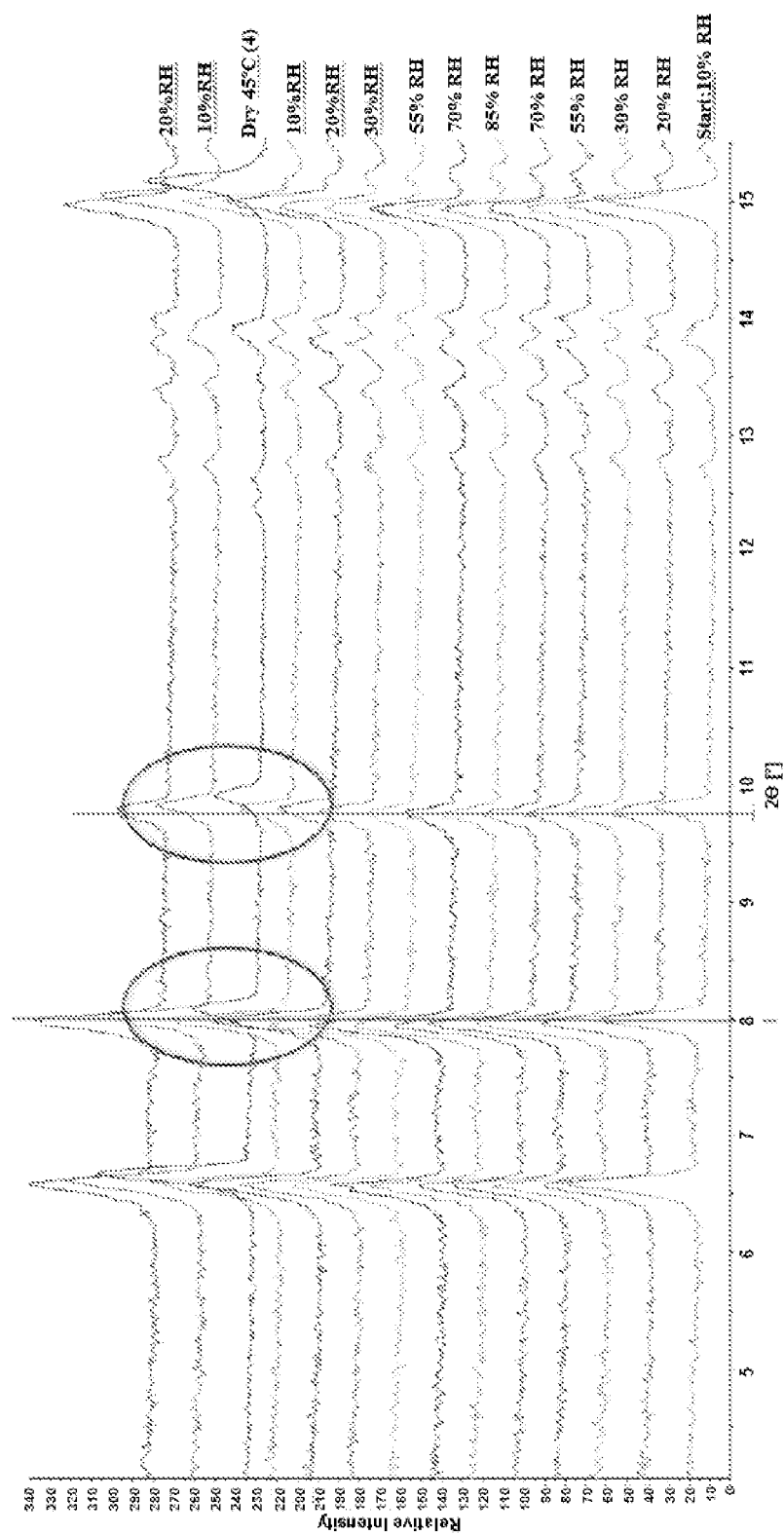
FIG. 27 depicts an overlay of XRPD patterns (zoom in on region 4-16°2θ) obtained from the variable humidity XRPD measurements of 3-[2-butyl-1-(2-diethylamino-ethyl)-1H-benzoimidazol-5-yl]-N-hydroxy-acrylamide dihydrochloride monohydrate (Form 1) at 30° C. (sequence from bottom to top). Highlighted with an oval shape are the main shifts of the diffraction peaks observed at a relative humidity below 10%.

The variable humidity XRPD did not show any solid form conversion between 10-85% RH at 30° C. (see FIG. 26). The humid controller of the XRPD cannot reach relative humidity levels above 85% RH. Therefore, the conversion of the monohydrate (Form 1) to the 2.5 hydrate (Form 3) occurring at RH above 85% in the DVS was not visible in this experiment. The most dry condition (RH<10%) was reached upon increasing the temperature to 45° C. This condition was maintained for 1 hour. No significant changes were seen at this low relative humidity level, except for a small shift in the diffraction peaks (see FIG. 27). This shift indicated that the crystal cell had shrunk most likely due to a partial water loss. As soon as the relative humidity was increased to 10%, the cell returned to its initial dimensions.

The variable humidity XRPD experiment indicated that 3-[2-butyl-1-(2-diethylamino-ethyl)-1H-benzoimidazol-5-yl]-N-hydroxy-acrylamide dihydrochloride monohydrate (Form 1) was physically stable at relative humidity conditions between 10-85% RH at 30° C.

Example 5: Polymorph Evaluation

Thermocycling Studies

Suspensions of 3-[2-butyl-1-(2-diethylamino-ethyl)-1H-benzoimidazol-5-yl]-N-hydroxy-acrylamide dihydrochloride monohydrate (Form 1) and 2.5 hydrate (Form 3) were prepared in 12 process relevant solvent systems. The suspensions were cycled between 5° C. and 50° C. followed by aging at 25° C. for 72 hours. The mixtures underwent a temperature profile as displayed in FIG. 52. Upon completion of the incubation time, the solids were collected, dried under ambient conditions and dried under deep vacuum before being analyzed by HT-XRPD. All the measured solids were exposed to accelerated ageing conditions (2 days at 40° C./70% RH) followed by re-analysis by HT-XRPD.

The 2.5 hydrate Form 3 was found in most of the thermocycling experiments. In most of the methanol/water mixtures tested the 2.5 hydrate Form 3 seems to be the most stable form. Nevertheless, in neat methanol the monohydrate (Form 1) was obtained.

In ethanol, absolute or extra dry, the monohydrate Form 1 transformed into the anhydrous Form 9 and the 2.5 hydrate Form 3 converted to the monohydrate Form 1. In almost all ethanol/water mixtures the 2.5 hydrate Form 3 is the most stable form.

Figure 28:
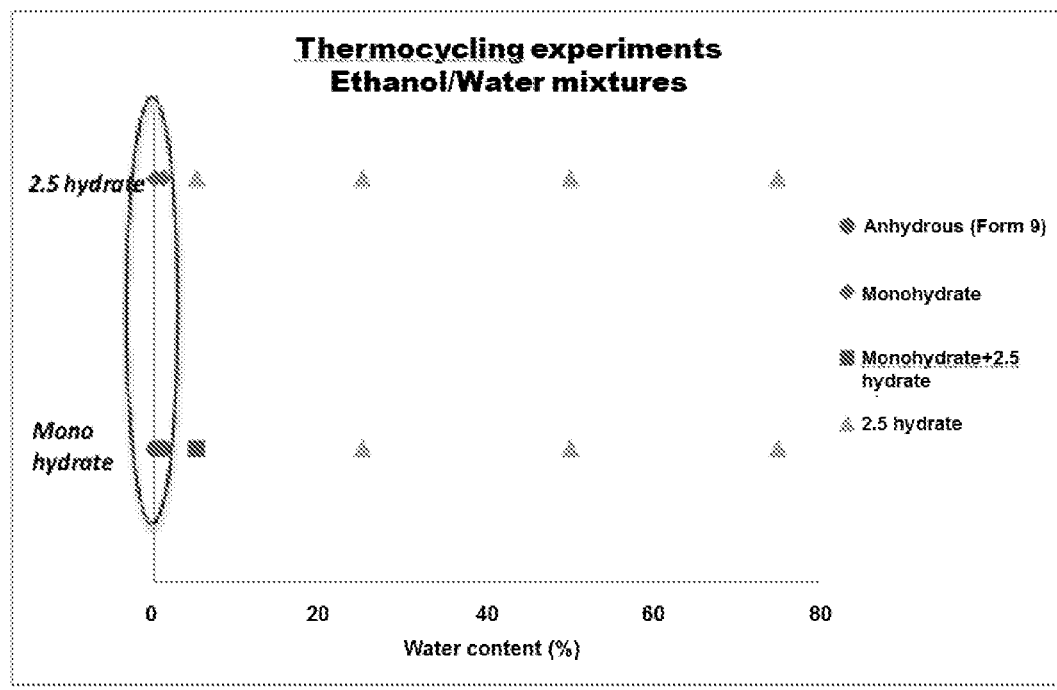
FIG. 28 depicts the solid form results obtained in the thermocycling experiments on 3-[2-butyl-1-(2-diethylamino-ethyl)-1H-benzoimidazol-5-yl]-N-hydroxy-acrylamide dihydrochloride 2.5 hydrate (Form 3) and monohydrate (Form 1) in several ethanol/water mixtures. Form 3 (2.5 hydrate) seems to be the most stable form in a wide range of ethanol/water mixtures. When no water is present in the mixture the monohydrate Form 1 transforms into the anhydrous Form 9 and the 2.5 hydrate (Form 3) into the monohydrate (Form 1) (highlighted with an oval shape).
Figure 29:
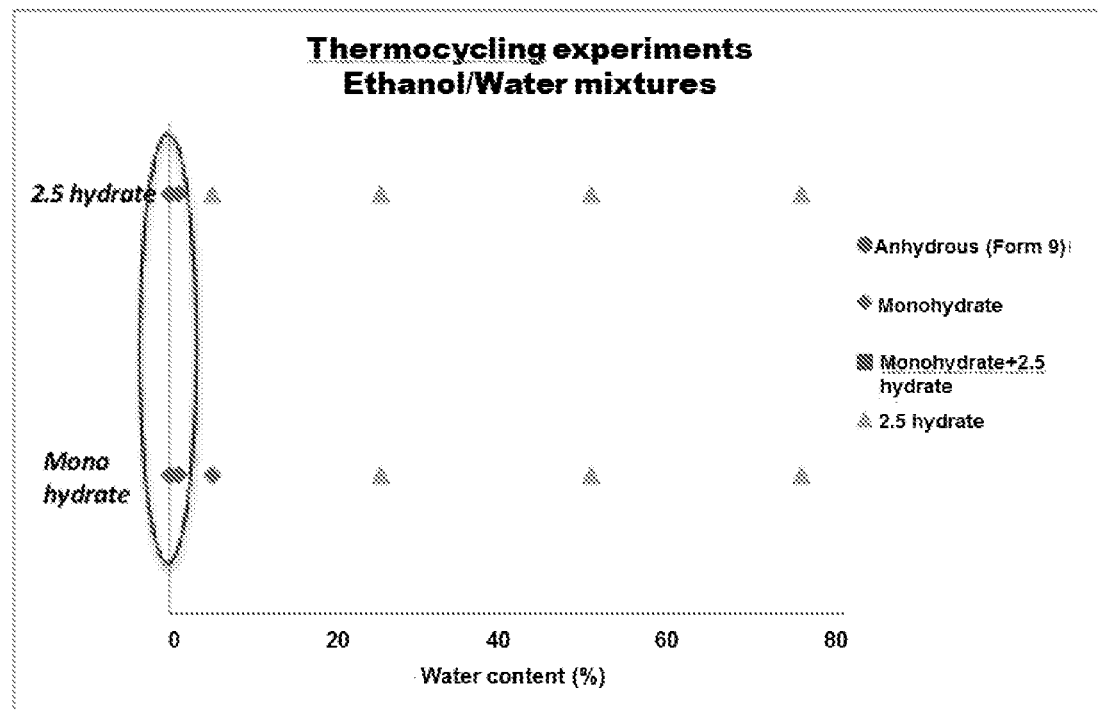
FIG. 29 depicts the solid form results obtained in the thermocycling experiments on 3-[2-butyl-1-(2-diethylamino-ethyl)-1H-benzoimidazol-5-yl]-N-hydroxy-acrylamide dihydrochloride 2.5 hydrate (Form 3) and monohydrate (Form 1) in several methanol/water mixtures. Form 3 (2.5 hydrate) seems to be the most stable form in a wide range of methanol/water mixtures. When no water is present in the mixture Form 3 (2.5 hydrate) converts to the monohydrate Form 1 (highlighted with an oval shape).
Figure 30A:
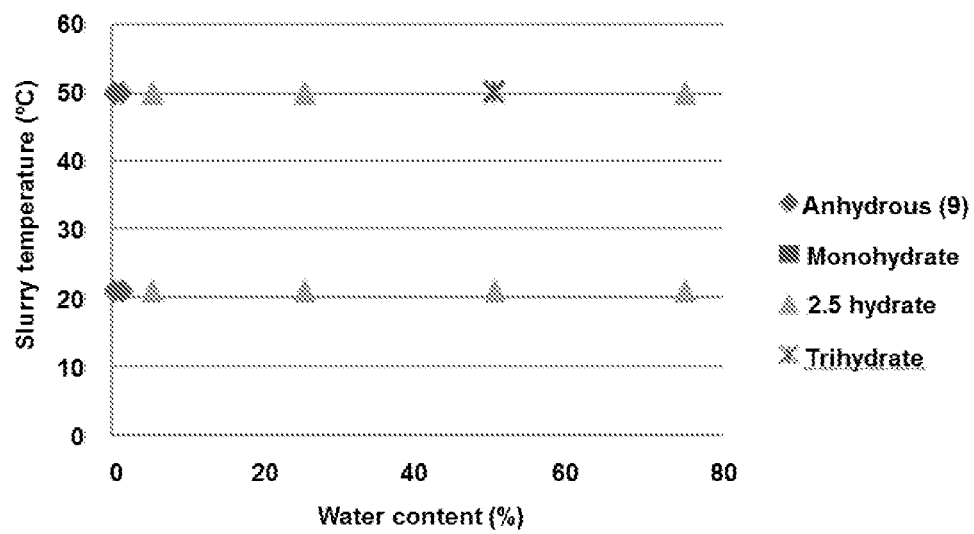
FIG. 30A depicts the results of the slurry conversion experiments on 3-[2-butyl-1-(2-diethylamino-ethyl)-1H-benzoimidazol-5-yl]-N-hydroxy-acrylamide dihydrochloride 2.5 hydrate (Form 3) under ambient conditions in ethanol/water mixtures.
Figure 30B:
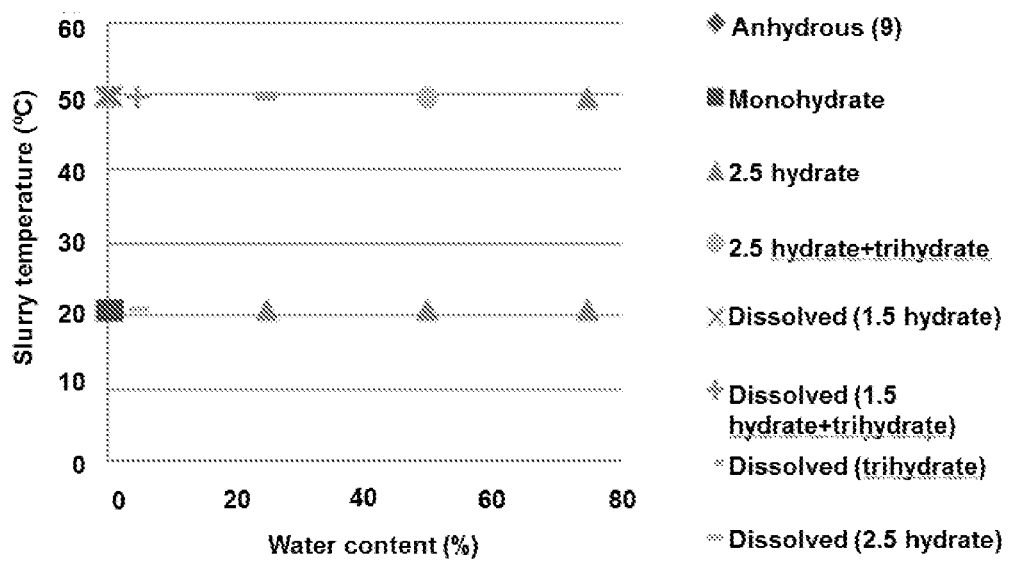
FIG. 30B depicts the results of the slurry conversion experiments on 3-[2-butyl-1-(2-diethylamino-ethyl)-1H-benzoimidazol-5-yl]-N-hydroxy-acrylamide dihydrochloride 2.5 hydrate (Form 3) under ambient conditions in methanol/water mixtures.
Figure 30C:
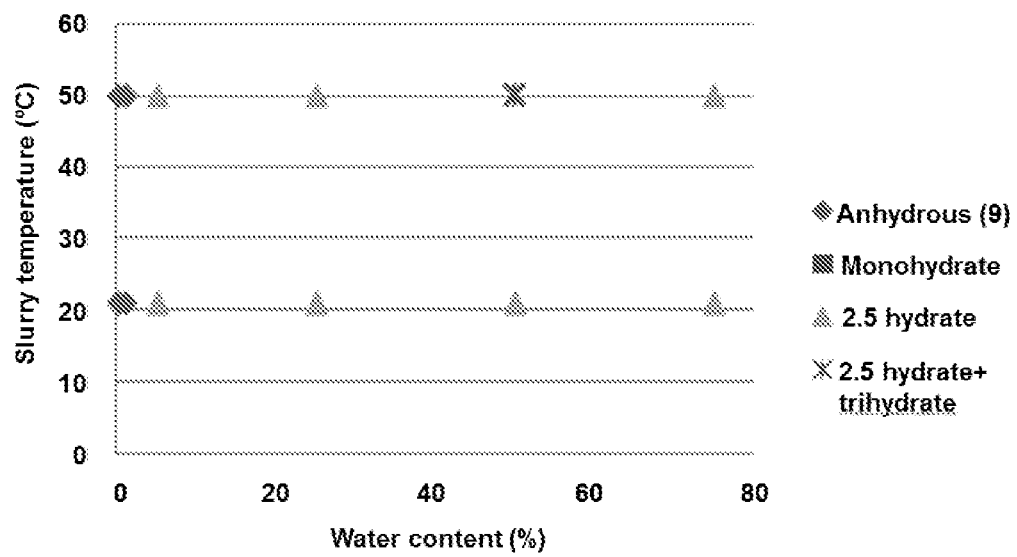
FIG. 30C depicts the results of the slurry conversion experiments on 3-[2-butyl-1-(2-diethylamino-ethyl)-1H-benzoimidazol-5-yl]-N-hydroxy-acrylamide dihydrochloride 2.5 hydrate (Form 3) under vacuum in ethanol/water mixtures.
Figure 30D:
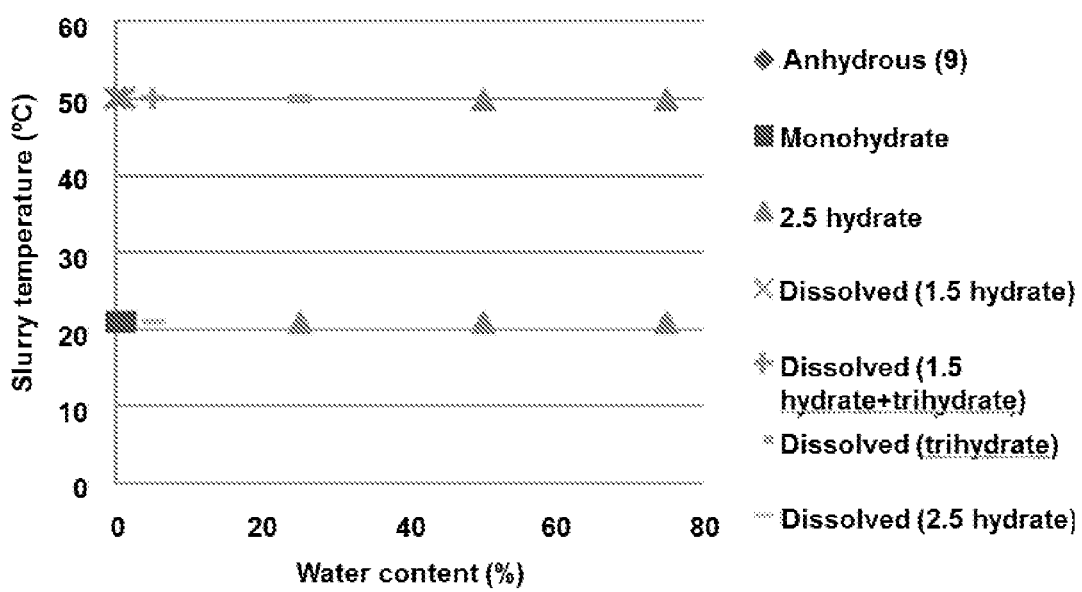
FIG. 30D depicts the results of the slurry conversion experiments on 3-[2-butyl-1-(2-diethylamino-ethyl)-1H-benzoimidazol-5-yl]-N-hydroxy-acrylamide dihydrochloride 2.5 hydrate (Form 3) under vacuum in methanol/water mixtures.

After accelerated aging conditions applied for 2 days all monohydrate Form 1 and anhydrous Form 9 samples had converted to the 2.5 hydrate Form 3. A graphic representation of the results obtained in these thermocycling experiments in different water mixtures is presented in FIG. 28 and FIG. 29.

Long Term Slurry Studies

Long-term slurry conversion experiments were carried out by preparing suspensions of 3-[2-butyl-1-(2-diethyl-amino-ethyl)-1H-benzoimidazol-5-yl]-N-hydroxy-acrylamide dihydrochloride 2.5 hydrate (Form 3) and monohydrate (Form 1) in 12 different solvents and solvent mixtures. Approximately 30 mg of the specific form was dosed in a standard HPLC vial and aliquots of 100 μL of solvent until a suspension was formed. The suspensions were stirred for 2 weeks at room temperature and for 1 week at 50° C. The solids were isolated from the mother liquor and analyzed by HT-XRPD after mild drying under ambient conditions (ambient) and after thorough drying under vacuum (vacuum). All the solids were exposed to accelerated ageing conditions (2 days at 40° C./70% RH) and re-analyzed by HT-XRPD.

In most of the experiments performed in ethanol/water mixtures the 2.5 hydrate Form 3 was obtained. However, in the absence of water at both temperatures, the anhydrous Form 9 was found. At 50° C., the trihydrated form (Form 2) was found in water mixtures containing 50% of water.

The monohydrate Form 1 transformed into the 2.5 hydrate (Form 3) in all ethanol/water and methanol/water mixtures at ambient conditions. When no water was present in the solvent system, conversion to the anhydrous Form 9 was observed. The monohydrate Form 1 was isolated in ethanol/water mixtures containing below 5% of water at 50° C. and in neat methanol at ambient conditions. The trihydrated Form 2 was again found in methanol/water and ethanol/water mixtures containing 50% of water.

The monohydrate Form 1 dissolved in almost all methanol/water mixtures at 50° C. that upon evaporation led to different solid forms, namely trihydrate Form 2, 1.5 hydrate Form 4 or 2.5 hydrate Form 3.

No significant changes were noticed upon drying the solids under vacuum. The trihydrate Form 2 seems to be physically unstable and upon drying converted to the 2.5 hydrate Form 3. After exposure to stress conditions for 2 days, all solid forms converted to the 2.5 hydrate (Form 3).

A graphic representation of the solid form obtained in the different solvent systems is presented in FIG. 30 and FIG. 31.

Desolvation Studies

Using solvent equilibration of hydrates in high boiling point solvents has been reported as a method to obtaining desolvated forms. Suspensions of 3-[2-butyl-1-(2-diethyl-amino-ethyl)-1H-benzoimidazol-5-yl]-N-hydroxy-acrylamide dihydrochloride 2.5 hydrate (Form 3) and monohydrate (Form 1) were equilibrated at 125° C. in four high boiling point solvents for two days. The experiments were started with approximately 50 mg of material and 100 μL of solvent. After equilibration, the solids were isolated from the solutions by centrifugation. The solids were allowed to dry under ambient conditions before HT-XRPD analysis was performed. The wet solids were analyzed by HT-XRPD immediately to avoid hydration under ambient conditions or under vacuum.

Table 13 presents the solid forms as assessed by HT-XRPD from desolvation experiments started with Form 3.

TABLE 13

| Solvent | Solids after Tprofile | Concentration (mg/mL) | Form in Ambient | Form in Ambient AAC* |
|---|---|---|---|---|
| Anisole | Yes | 525 | Mono | 2.5 |
| Cumene | Yes | 519 | Mono | 2.5 + Mono |
| p-Xylene | Yes | 563 | Mono | 2.5 |
| N-Methyl-2-pyrrolidone | Yes | 504 | Mono | 2.5 |

*ACC: Accelerated Aging Conditions

Table 14 presents the solid forms as assessed by HT-XRPD from desolvation experiments started with Form 1.

TABLE 14

| Solvent | Solids after Tprofile | Concentration (mg/mL) | Form in Ambient | Form in Ambient AAC* |
|---|---|---|---|---|
| Anisole | Yes | 245.5 | Mono | 2.5 |
| Cumene | Yes | 254 | Mono | 2.5 |
| p-Xylene | Yes | 265.5 | Mono | 2.5 |
| N-Methyl-2-pyrrolidone | Yes | 248.5 | No solids | N/A |

*ACC: Accelerated Aging Conditions

The desolvation experiments on 3-[2-butyl-1-(2-diethylamino-ethyl)-1H-benzoimidazol-5-yl]-N-hydroxy-acrylamide dihydrochloride 2.5 hydrate (Form 3) led in all cases to the monohydrated Form 1. 3-[2-butyl-1-(2-diethylamino-ethyl)-1H-benzoimidazol-5-yl]-N-hydroxy-acrylamide dihydrochloride monohydrate Form 1 did not change over the equilibration time. After exposure to accelerated aging conditions, the obtained monohydrate Form 1 converted to the 2.5 hydrate Form 3.

Competitive Slurry Studies

Competitive slurry conversion experiments were started with equimolar amounts of 3-[2-butyl-1-(2-diethylamino-ethyl)-1H-benzoimidazol-5-yl]-N-hydroxy-acrylamide dihydrochloride 2.5 hydrate Form 3 and monohydrate Form 1. Approximately 50 mg of each solid form were solid dosed in a standard HPLC vial followed by solvent addition.

The competitive slurry experiments were performed in ethanol/water mixtures and methanol/water mixtures within a water activity range of 0-0.2. Approximately 50 mg of each pracinostat dihydrochloride solid form 2.5 hydrate and monohydrate were solid dosed in 1.8 mL HPLC vials. Aliquots of 100 µL of the different water mixtures were added until about half of the amount of solid was in solution. Subsequently, the vials were stirred for one week at 5° C., 21° C. and 50° C. Upon completion of the equilibration time, the solids were separated from the liquids by centrifugation. The solids were dried under ambient conditions (ambient) and dried under vacuum (vacuum) before HT-XRPD analysis. All solid samples were exposed to accelerated gaining conditions (40° C. and 70% RH) for two days (AAC). The water content in the liquid phase was determined Karl Fischer analysis.

In FIG. 32 and FIG. 33, the solid form designation at the different slurry temperatures vs the determined water content is represented for each solvent system.

The thermodynamic stability study of 3-[2-butyl-1-(2-diethylamino-ethyl)-1H-benzoimidazol-5-yl]-N-hydroxy-acrylamide dihydrochloride solid forms in ethanol/water showed that the monohydrated Form 1 is the thermodynamically most stable form in a very limited range of water activity: At 5° C. when the water content in the solvent system is below 2%; At ambient conditions it seems that the anhydrous (Form 9) and monohydrate (Form 1) are coexisting at the same water content range (2.5% of water); At elevated temperatures when the water content is between 2-4% of water.

The anhydrous Form 9 was the most stable form at ambient conditions in ethanol/water mixtures containing below 2.5% of water. At 50° C., this form appears to be stable in mixtures containing below 1.5% of water in the mixture.

The 2.5 hydrate Form 3 was obtained in ethanol/water mixtures containing above 3% of water at ambient conditions. At temperature below ambient, the water content in the solvent mixture needs to be above 2%.

The methanol/water mixtures led in most of the cases to clear solutions, which after evaporation produced the 2.5 hydrate Form 3. At 5° C., the monohydrated Form 1 seems to be the most stable form in all methanol/water mixtures containing below 6% of water.

Example 6: Analysis of Anhydrous Polymorph Form 9

X-Ray Powder Diffraction of Form 9

HR-XRPD of the obtained 3-[2-butyl-1-(2-diethylamino-ethyl)-1H-benzoimidazol-5-yl]-N-hydroxy-acrylamide dihydrochloride anhydrous Form 9 (obtained in the slurry conversion experiment in ethanol extra dry) was recorded (see FIGS. 37 and 38). The determined cell parameters are presented in Table 15.

TABLE 15

| Identification code | Anhydrous Form 9 |
|---|---|
| Empirical formula | $C_{20}H_{32}N_4O_2^+ \cdot 2Cl^-$ |
| Fw | 431.40 |
| T [K] | 296 (2) |
| λ [Å] | 1.54056 |
| Crystal system | Monoclinic |
| Space group | $P2_1/n$ |
| Unit cell dimensions | |
| a [Å] | 8.9892 (2) |
| b [Å] | 11.3280 (2) |
| c [Å] | 22.1009 (4) |
| β [°] | 102.5527 (8) |
| V [Å$^3$] | 2196.74 (6) |
| Z (Z') | 4 (1) |
| $D_c$ [g/cm$^3$] | 1.304 |
| $D_c$ [g/cm$^3$] | |
| Capillary size [mm$^2$] | 0.3 × 8 |
| 2θ Step size [°] | 0.016 |
| No of steps | 2408 |
| Time per step [s] | 10 |
| 2θ range [°] | 3.5 → 41.5 |
| Rexp | 1.59 |
| $R_{wp}$ | 2.11 |
| $R_p$ | 1.60 |
| GOF | 1.33 |
| $R_{Brag}$ | 0.06 |
| Amorphous Content [%] | Not determined |
| Impurities [%] | ~0.1% |

Thermal Analyses of Form 9

DSC analysis with a heating rate of 10° C./min was performed with polymorph Form 9 according to the methods described herein. One single endotherm was observed at 191.8° C. followed by an exothermic event follows at 204.9° C. attributed to the thermal decomposition of the hydrochloride salt. (See FIG. 39) TGA/SDTA and TGMS analysis of anhydrous Form 9 indicated that there was no significant mass loss prior to the thermal decomposition. (See FIG. 40A and FIG. 40B) This thermal behavior confirmed the anhydrous nature of this form.

Example 7: Analysis of Trihydrate Polymorph Form 2

X-Ray Powder Diffraction of Form 2

HT-XRPD of the obtained 3-[2-butyl-1-(2-diethylamino-ethyl)-1H-benzoimidazol-5-yl]-N-hydroxy-acrylamide dihydrochloride trihydrate Form 2 (obtained in the slurry conversion experiment on the monohydrate Form 1 in methanol/water (75/25) at 50° C.) was recorded. FIG. 41 depicts the overlay of HT-XRPD patterns of Form 2 and Form 3.

Thermal Analyses of Form 2

DSC analysis with a heating rate of 10° C./min was performed with polymorph Form 2 according to the methods described herein. A first broad endotherm was observed at 80.3° C. followed by two small endotherms at 116.9° C. and 146.0° C. An exothermic event followed at 200.7° C., which was attributed to the thermal decomposition of the hydrochloride salt. (See FIG. 42) TGA/SDTA and TGMS analysis of anhydrous Form 2 was performed. The TGA signal indicated a mass loss of 10.5% which based on the MS signal can be attributed to water (10.5% of water corresponds to 2.8 molecules of water per molecule of API). (See FIG. 43A and FIG. 43B) This thermal behavior confirmed the trihydrate nature of this form.

Example 8: Analysis of 1.5 Hydrate Polymorph Form 4

X-Ray Powder Diffraction of Form 4

HT-XRPD of the obtained 3-[2-butyl-1-(2-diethylaminoethyl)-1H-benzoimidazol-5-yl]-N-hydroxy-acrylamide dihydrochloride 1.5 hydrate Form 4 (obtained in the slurry conversion experiment on the 2.5 hydrate Form 3 in ethanol at ambient conditions for 2 hours) was recorded. FIG. 44 depicts the overlay of HT-XRPD patterns of Form 4 and Form 3.

Thermal Analyses of Form 4

DSC analysis with a heating rate of 10° C./min was performed with polymorph Form 4 according to the methods described herein. A first endotherm was observed at 136.3° C. followed by a second endotherm at 156.8° C. An exothermic event followed at 200.0° C., which was attributed to the thermal decomposition of the hydrochloride salt. (See FIG. 45) TGA/SDTA and TGMS analysis of anhydrous Form 4 was performed. The TGA signal indicated a mass loss of 6.1% which based on the MS signal can be attributed to water and ethanol (1.6 molecules of water or 0.6 molecules of ethanol per molecule of API). (See FIG. 46A and FIG. 46B)

Example 9: Analysis of Hemi-ethanol Solvate (0.5 Ethanol) Polymorph Form 7

X-Ray Powder Diffraction of Form 7

HT-XRPD of the obtained 3-[2-butyl-1-(2-diethylaminoethyl)-1H-benzoimidazol-5-yl]-N-hydroxy-acrylamide dihydrochloride hemi-ethanol solvate Form 7 and wet solids Form 8 (obtained in the wet solid after 20 hours slurry of Form 3 in ethanol absolute at ambient conditions after drying the wet solids for 2 hours at 10 mbar) was recorded. FIG. 47 depicts the overlay of HT-XRPD patterns of Form 7, Form 8, and Form 3.

Thermal Analyses of Form 7

TGA/SDTA and TGMS analysis of hemi-ethanol solvate Form 7 was performed. A mass loss of 5.1% was observed in the temperature range 25-180° C. This mass loss corresponds to 0.5 molecules of ethanol per molecule of API. (See FIG. 48A and FIG. 48B)

Example 10: Analysis of Hemihydrate (0.5 Water) Polymorph Form 10

X-Ray Powder Diffraction of Form 10

HT-XRPD of the obtained 3-[2-butyl-1-(2-diethylaminoethyl)-1H-benzoimidazol-5-yl]-N-hydroxy-acrylamide dihydrochloride hemihydrate Form 10 (obtained by freeze drying a water solution) was recorded. FIG. 49 depicts the overlay of HT-XRPD patterns of Form 10 and Form 3.

Thermal Analyses of Form 10

DSC analysis with a heating rate of 10° C./min was performed with polymorph Form 10 according to the methods described herein. A first endotherm was observed at 146.0° C. followed by an exothermic event at 199.9° C., which was attributed to the thermal decomposition of the hydrochloride salt. (See FIG. 50) TGA/SDTA and TGMS analysis of hemihydrate Form 10 was performed. A mass loss of 2.6% was observed in the temperature range 25-160° C. This mass loss corresponds to 0.5 molecules of water per molecule of API. (See FIG. 51A and FIG. 51B)

Example 11: Analytical Techniques

High Throughput X-Ray Powder Diffraction

Plates were mounted on a Bruker General Area Detector Diffraction System (GADDS) equipped with a VANTEC-500 gas area detector corrected for intensity and geometric variations. The calibration of the measurement accuracy (peaks position) was performed using NIST SRM1976 standard (Corundum).

Data collection was carried out at room temperature using monochromatic CuKα radiation in the 2 Å region between 1.5° and 41.5°, which is the most distinctive part of the XRPD pattern. The diffraction pattern of each well was collected in two 2θ ranges ($1.5° \leq 2\Theta \leq 21.5°$ for the first frame, and $19.5° \leq 2\Theta \leq 41.5°$ for the second) with an exposure time of 90 s for each frame. No background subtraction or curve smoothing was applied to the XRPD patterns.

The carrier material used during XRPD analysis was transparent to X-rays and contributed only slightly to the background.

High Resolution X-Ray Powder Diffraction

The powder data were collected on D8 Advance diffractometer using Cu Kα1 radiation (1.54016 Å) with germanium monochromator at room temperature. The data were collected in 2θ alone (detector scan) mode from 4 to 45° (2θ), using a step width of 0.016°, measuring for 3426.5 seconds per step using a solid state LynxEye detector. The sample was measured in 8 mm long glass capillary with 0.5 mm outer diameter. Rietveld calculations were performed used Topas 4-2 suite.

In brief, the solids were finely grounded in a mortar with pestle. Subsequently a boron glass capillary (0.3 mm diameter) was filled with the compound and carefully placed in the diffractometer. Each step was measured for 0.05 seconds.

Cell parameters as well as crystal system were obtained using LSI-Index (Coelho, 2003; Coehlo & Kern, 2005) indexing program. The space group was selected based on reflections condition as well as symmetry of the molecule. In this case because compound is not chiral nor crystal has none non linear optics properties in every case the centrosymmetric space groups were selected. Calculation of crystal density was based on molecular weight reported in the literature as well as from HPLC measurements. The cell parameters, purity as well as instrument parameters were refined using Whole Powder Pattern Decomposition method (Pawley). The following criteria of fit were used:

Yo,m and Yc,m are the observed and calculated data, respectively at data point m, M the number of data points, P the number of parameters, wm the weighting given to data point m which for counting statistics is given by wm=1/σ(Yo,m)2 where σ(Yo,m) is the error in Yo,m, $$R_{exp} = \sqrt{\frac{M-P}{\sum w_m Y_{o,m}^2}} \, ; \, R_{wp} = \sqrt{\frac{\sum w_m(Y_{o,m} - Y_{c,m})^2}{\sum w_m Y_{o,m}^2}} \, ;$$

$$R_P = \sqrt{\frac{\sum |Y_{o,m} - Y_{c,m}|}{\sum Y_{o,m}}}$$

$$GOF = chi^2 = \frac{R_{wp}}{R_{exp}} \sqrt{\frac{\sum w_m(Y_{o,m} - Y_{c,m})^2}{M-P}}$$

Variable Temperature and Humid XRPD

For variable humidity and temperature experiments the ANSYCO HT chamber was used, installed within the D8 Advance system diffractometer (Bruker) designed with Brag-Brentano geometry and equipped with LynxEye solid state detector. The radiation used for collecting the data was CuK$\alpha$1 ($\lambda$=1.54056 Å) monochromatized by germanium crystal. The material was placed on a fixed sample holder that was mounted inside the chamber.

VH-XRPD: The humidity was applied locally and varied from 10 to 85% (dew point). The patterns were collected in the range 4-41°2θ, with a step of 0.01571°2θ (for the VH-XRPD) and measuring time per step of 0.5 sec (for the 2.5 hydrate Form 3 measurement) or 0.85 sec (for the monohydrate Form 1 measurement). Data collection was initiated after 15 min stabilization of humidity at each step. All patterns were taken at 30° C.

VT-XRPD: The temperature variation rate was 10° C./min and the equilibration time, prior to starting the data collection at each temperature, was 8 min. The patterns were collected in the range 4-41°2θ, with a step of 0.01573°2θ and measuring time per step of 1 sec. The data collection time, per temperature, was 40 min.

Thermal Analysis

DSC Analysis: Melting properties were obtained from DSC thermograms, recorded with a heat flux DSC822e instrument (Mettler-Toledo GmbH, Switzerland). The DSC822e was calibrated for temperature and enthalpy with a small piece of indium (melting point at 156.6° C.; $\Delta$Hf=28.45 J. g$^{-1}$). Samples were sealed in standard 40 $\mu$l aluminum pans, pin-holed and heated in the DSC from 25° C. to 300° C., at a heating rate of 10° C. min$^{-1}$. Dry N2 gas, at a flow rate of 50 ml min$^{-1}$ was used to purge the DSC equipment during the measurement.

TGMS Analysis: Mass loss due to solvent or water loss from the crystals was determined by TGA/SDTA. Monitoring the sample weight, during heating in a TGA/SDTA851e instrument (Mettler-Toledo GmbH, Switzerland), which resulted in a weight vs. temperature curve. The TGA/SDTA851e was calibrated with samples of indium and aluminum. Samples were weighed into 100 $\mu$l aluminum crucibles and sealed. The seals were pin-holed and the crucibles heated in the TGA from 25 to 300° C. at a heating rate of 10° C. min$^{-1}$. Dry N2 gas was used for purging. The gases coming from the TGA samples were analyzed by a mass spectrometer Omnistar GSD 301 T2 (Pfeiffer Vacuum GmbH, Germany). The latter is a quadrupole mass spectrometer, which analyzes masses in the range of 0-200 amu.

Karl Fischer Analysis

Water content is determined by means of a direct coulometric Karl Fischer titration with a SI analytics TitroLine 7500 KF trace equipped with TZ 1753 generator electrode with a diaphragm. As a reference HYDRANAL-Water Standard 1.0 Liquid standard with a water content of 1.0 mg/g (0.1%) was used to validate the performance of the system.

Scanning Electron Light Microscopy

Scanning Electron microscopy pictures are taken with a Zeiss Sigma-300 microscope equipped with a field emission source. Which detector was used is stated on the picture (after Signal A). The working distance (WD) and used acceleration voltage (EHT) are given on the picture itself as well.

DVS Analysis

Differences in hygroscopicity (moisture uptake) of the various forms of a solid material provided a measure of their relative stability at increasing relative humidity. Moisture sorption isotherms of small samples were obtained using a DVS-1 system from Surface Measurement Systems (London, UK); this instrument is suitable for use with as little as a few milligrams of sample, with an accuracy of 0.1 $\mu$g. Several humidity profile were applied as described in each individual experiment. Steps consisted of 10% RH. Weight equilibration per step was set with a minimum holding time of 1 hour (10% relative humidity step). At the end of the DVS experiments, the recovered solid material was measured by HT-XRPD.

HPLC Analytical Method

HPLC System:

Agilent 1200; Detector 1: DAD set at 248 nm; Detector 2: HP1100 LC/MSD in Positive Scan mode HPLC Conditions:

Autosampler temp: 15° C.; Column: Waters Sunfire C18 (100×4.6 mm; 3.5 $\mu$m); Column temp: 35° C.; Flowcel: 10 mm path; Gradient: Mobile phase A: 10 mM Ammonium acetate Mobile phase B: Acetonitrile LC/MS grade; Flow: 1.0 ml/min

|  | Time [min]: | Eluent A: | Eluent B: |
|---|---|---|---|
| Gradient: | 0 | 90% | 10% |
| | 1 | 90% | 10% |
| | 6 | 10% | 90% |
| | 9 | 10% | 90% |
| | 10 | 90% | 10% |

Sample:

Concentration: ca. 0.5 mg/ml; Solvent: 10 mM ammonium acetate:acetonitrile (50:50 v/v); Injection volume: 5 $\mu$l The compound integrity is expressed as a peak-area percentage, calculated from the area of each peak in the chromatogram, except the 'injection peak', and the total peak-area, as follows:

$$\text{peak area (\%)} = \frac{\text{peak area}}{\text{total area of all peaks}} \cdot 100\%$$

The peak area percentage of the compound of interest is employed as an indication of the purity of the component in the sample.

What is claimed is:

1. A crystalline polymorph of 3-[2-butyl-1-(2-diethyl-amino-ethyl)-1H-benzoimidazol-5-yl]-N-hydroxy-acrylamide dihydrochloride 2.5 hydrate characterized by a powder X-ray diffraction pattern having peaks at 6.46, 20.26, and 26.68° 2θ±0.1° 2θ.

2. The crystalline polymorph of claim 1, further characterized by a peak at 22.27° 2θ±0.1° 2θ.

3. The crystalline polymorph of claim 1, further characterized by at least two peaks at 9.78, 16.57, or 19.58° 2θ±0.1° 2θ.

4. The crystalline polymorph of claim 1 that exhibits an X-ray powder diffraction pattern substantially similar to, or the same as, the X-ray powder diffraction pattern shown in FIG. 1.

5. A crystalline polymorphic form of 3-[2-butyl-1-(2-diethylamino-ethyl)-1H-benzoimidazol-5-yl]-N-hydroxy-acrylamide dihydrochloride 2.5 hydrate having an X-ray powder diffraction pattern with at least the major peaks shown in FIG. 1.

6. A solid pharmaceutical composition comprising an effective amount of the crystalline polymorph of claim 1 and at least one pharmaceutically acceptable excipient or carrier.

7. A method of inhibiting histone deacetylase in a patient comprising administering to the patient an effective amount of the crystalline polymorph of claim 1.

8. A method of treating cancer in a patient comprising administering to the patient an effective amount of the crystalline polymorph of claim 1.

9. The method of claim 8, wherein the cancer is chemoresistant, refractory or non-responsive to chemotherapy.

10. The method of claim 9, wherein the cancer is resistant to azacitidine, decitabine, lenalidomide, TXA-127, or combinations thereof.

11. The method of claim 8, wherein the cancer is breast cancer, colon cancer, prostate cancer, pancreatic cancer, leukemia, lymphoma, ovarian cancer, neuroblastoma, melanoma, or a hematologic malignancy.

12. The method of claim 11, wherein the cancer is myelodysplastic syndrome (MDS).

13. The method of claim 11, wherein the cancer is acute myeloid leukemia (AML).

* * * * *